United States Patent
Supuran et al.

(10) Patent No.: US 9,463,171 B2
(45) Date of Patent: Oct. 11, 2016

(54) SULFONAMIDE COMPOUNDS FOR INHIBITION OF METASTATIC TUMOR GROWTH

(71) Applicant: Welichem Biotech Inc., Burnaby (CA)

(72) Inventors: Claudiu Supuran, Florence (IT);
Shoukat Dedhar, Richmond (CA);
Paul C. McDonald, Coquitlam (CA);
Fabrizio Carta, Nuoro (IT)

(73) Assignee: Welichem Biotech Inc., Burnaby (CA)

( * ) Notice: Subject to any disclaimer, the term of this patent is extended or adjusted under 35 U.S.C. 154(b) by 758 days.

(21) Appl. No.: 13/737,704

(22) Filed: Jan. 9, 2013

(65) Prior Publication Data

US 2013/0190396 A1  Jul. 25, 2013

Related U.S. Application Data

(63) Continuation-in-part of application No. PCT/CA2011/000727, filed on Jun. 22, 2011.

(60) Provisional application No. 61/363,196, filed on Jul. 9, 2010.

(51) Int. Cl.
| | | |
|---|---|---|
| A61K 31/18 | (2006.01) | |
| A61K 31/63 | (2006.01) | |
| A61K 45/06 | (2006.01) | |
| C07C 311/47 | (2006.01) | |
| A61K 31/277 | (2006.01) | |

(52) U.S. Cl.
CPC ............ *A61K 31/18* (2013.01); *A61K 31/277* (2013.01); *A61K 31/63* (2013.01); *A61K 45/06* (2013.01); *C07C 311/47* (2013.01); *C07C 2101/08* (2013.01); *C07C 2102/08* (2013.01); *C07C 2103/18* (2013.01)

(58) Field of Classification Search
None
See application file for complete search history.

(56) References Cited

U.S. PATENT DOCUMENTS

| | | | |
|---|---|---|---|
| 3,340,144 A | 9/1967 | Martin et al. | |
| 5,401,490 A | 3/1995 | Wiebe et al. | |
| 5,665,675 A | 9/1997 | Nagai et al. | |
| 5,843,404 A | 12/1998 | Koch et al. | |
| 5,919,816 A * | 7/1999 | Hausheer | A61K 31/185 514/100 |
| 7,378,091 B2 | 5/2008 | Gudas et al. | |
| 7,550,424 B2 * | 6/2009 | Supuran | A61K 31/18 435/4 |
| 7,829,065 B2 * | 11/2010 | Supuran | A61K 31/18 424/9.1 |
| 7,833,514 B2 * | 11/2010 | Supuran | A61K 31/18 424/9.1 |
| 7,833,734 B2 * | 11/2010 | Supuran | A61K 31/18 435/4 |
| 7,833,737 B2 * | 11/2010 | Supuran | A61K 31/18 435/7.23 |
| 7,833,738 B2 * | 11/2010 | Supuran | A61K 31/18 435/7.23 |
| 7,833,739 B2 * | 11/2010 | Supuran | A61K 31/18 435/7.23 |
| 8,628,771 B2 * | 1/2014 | Supuran | A61K 31/18 424/130.1 |
| 2009/0175794 A1 | 7/2009 | Zimmerman et al. | |

FOREIGN PATENT DOCUMENTS

| | | |
|---|---|---|
| CA | 2255858 | 12/1997 |
| CA | 2664365 A1 | 4/2008 |
| CN | 101516361 A | 8/2009 |
| EP | 0 741 046 A1 | 11/1996 |
| GB | 976528 | 11/1964 |
| JP | 8-142524 A | 6/1996 |
| WO | 2004/048544 A2 | 6/2004 |
| WO | 2004/048544 A3 | 6/2004 |
| WO | 2005/044194 A2 | 5/2005 |
| WO | 2009/089383 A2 | 7/2009 |
| WO | 2010/138820 A2 | 12/2010 |
| WO | 2010/138820 A3 | 12/2010 |

OTHER PUBLICATIONS

Driessen et al. "Expression of Carbonic Anhydrase IX (CA IX), a Hypoxia-Related Protein, Rather Than Vascular-Endothelial Growth Factor (VEGF), a Pro-Angiogenic Factor, Correlates With an Extremely Poor Prognosis in Esophageal and Gastric Adenocarcinomas", Ann Surg, 2006; 243(3):334-340.*

Dorai et al. "The Role of Carbonic Anhydrase IX Overexpression in Kidney Cancer", European Journal of Cancer, 2005; 41:2935-2947.*

Pastorekova et al. "Cancer-Associated Carbonic Anhydrases and Their Inhibition". Curr Pharm Des. 2008; 14(7):685-698. [Abstract Only].*

Ahlskog et al., "In vivo targeting of tumor-associated carbonic anhydrases using acetazolamide derivatives," *Bioorganic & Medicinal Chemistry Letters 19*: 4851-4856, 2009.

Neri et al., "Interfering with pH regulation in tumours as a therapeutic strategy," *Nature Reviews Drug Discovery 10*: 767-777, Oct. 2011.

Özensoy et al., "Carbonic anhydrase inhibitors: Inhibition of the tumor-associated isozymes IX and XII with a library of aromatic and heteroaromatic sulfonamides," *Bioorganic & Medicinal Chemistry Letters 15*: 4862-4866, 2005.

Pacchiano et al , "Inhibition of β-carbonic anhydrases with ureido-substituted benzenesulfonamides," *Bioorganic & Medicinal Chemistry Letters 21*: 102-105, 2011.

(Continued)

*Primary Examiner* — Leslie A. Royds Draper
(74) *Attorney, Agent, or Firm* — Oyen Wiggs Green & Mutala LLP

(57) ABSTRACT

Therapeutic ureido-sulfonamide compositions having compounds with the formula

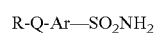

are disclosed, which compounds selectively inhibit CAIX and CAXII, and which are effective to inhibit hypoxic tumor growth, suppress metastases, and impair and deplete cancer stem cells in mammals.

5 Claims, 19 Drawing Sheets

(56) References Cited

OTHER PUBLICATIONS

Pacchiano et al., "Ureido-Substituted Benzenesulfonamides Potently Inhibit Carbonic Anhydrase IX and Show Antimetastatic Activity in a Model of Breast Cancer Metastasis," *Journal of Medicinal Chemistry 54*: 1896-1902, 2011.

Pastorekova et al., "Carbonic anhydrase inhibitors: Inhibition of the tumor-associated isozymes IX and XII with polyfluorinated aromatic/heterocyclic sulfonamides," *Journal of Enzyme Inhibition and Medicinal Chemistry 20*(3): 211-217, Jun. 2005.

Poulsen et al., "Carbonic anhydrase inhibition as a cancer therapy: a review of patent literature, 2007-2009," *Expert Opin. Ther. Patents 20*(6): 795-806, 2010.

Scozzafava et al., "Carbonic Anhydrase Inhibitors: Synthesis of N-Morpholyl-thiocarbonylsulfenylamino Aromatic/Heterocyclic Sulfonamides and their Interaction with Isozymes I, II and IV," *Bioorganic & Medicinal Chemistry Letters 10*: 1117-1120, 2000.

Supuran, "Carbonic anhydrases: novel therapeutic applications for inhibitors and activators," *Nature Reviews Drug Discovery 7*: 168-181, Feb. 2008.

Supuran et al., "Carbon anhydrase inhibitors—Part 49: Synthesis of substituted ureido and thioureido derivatives of aromatic/heterocyclic sulfonamides with increased affinities for isozyme I," *Eur. J. Med. Chem. 33*: 83-93, 1998.

Supuran et al., "Carbonic Anhydrase Inhibitors: Aromatic Sulfonamides and Disulfonamides Act As Efficient Tumor Growth Inhibitors," *J. Enzyme Inhibition 15*: 597-610, 2000.

Supuran et al., "Carbonic Anhydrase Inhibitors: Sulfonamides as Antitumor Agents?," *Bioorganic & Medicinal Chemistry 9*: 703-714, 2001.

Supuran et al., "Carbonic anhydrases as targets for medicinal chemistry," *Bioorganic & Medicinal Chemistry 15*: 4336-4350, 2007.

* cited by examiner

Figure 9
A 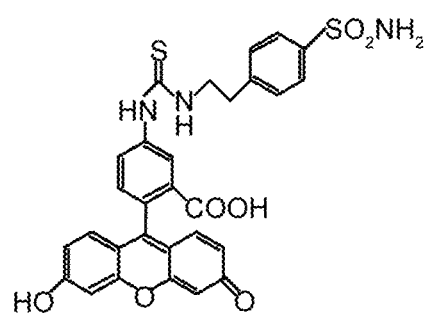
B 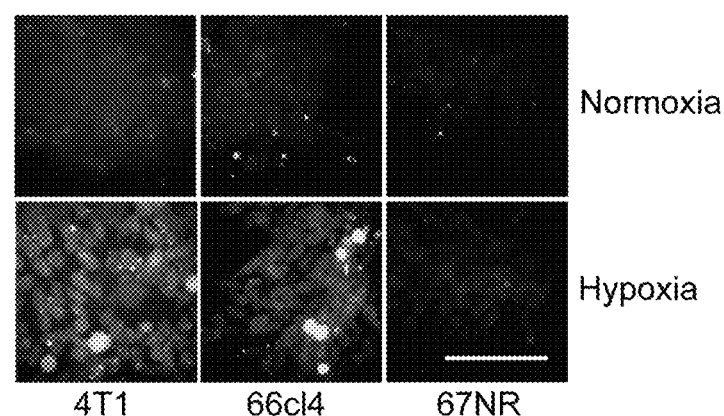
C 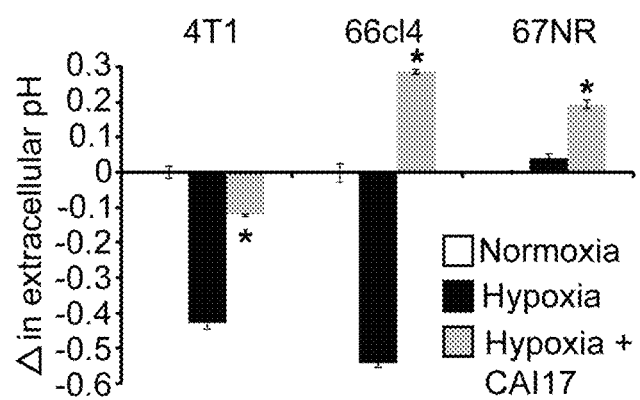

SULFONAMIDE COMPOUNDS FOR INHIBITION OF METASTATIC TUMOR GROWTH

BACKGROUND

1. Field of Invention

The disclosure is in the field of novel sulfonamide compounds, particularly for use as inhibitors of carbonic anhydrase IX and XII, in the treatment of hypoxic and metastatic cancer, and the depletion of cancer stem cells in mammals.

2. Description of Related Art

Sixteen different α-carbonic anhydrase (CA) isoforms have been isolated and characterized in mammals, where they play important physiological roles. Some of them are cytosolic (CAI, CAII, CAIII, CAVII, CAXIII), others are membrane-bound (CAIV, CAIX, CAXII, CAXIV and CAXV), CA VA and CA VB are mitochondrial, and CAVI is secreted in saliva and milk. The mammalian CAs were the first such enzymes isolated and studied in detail (Supuran, C T. Nat. Rev. Drug Discov. 2008, 7, p168, Supuran, C. T.; Scozzafava, A. *Bioorg. Med. Chem.* 2007, 15, 4336) and many of them are established therapeutic targets. The classical CA inhibitors are the primary sulfonamides, $RSO_2NH_2$, which have been in clinical use for more than 50 years as diuretics and antiglaucoma drugs. In fact there are around 30 clinically used drugs (or agents in clinical development) belonging to the sulfonamide or sulfamate class which show CAs inhibitory activity (Supuran, C. (2008) Nature, Vol 7: 168-181) and some of which are established as diuretics and antiglaucoma agents.

It has recently emerged that CA inhibitors have potential as, inter alia, anticancer drugs. However critical barriers to the design of CA inhibitors as therapeutic agents are related to the high number of isoforms in humans (i.e., 16 CAs, of which 13 have catalytic activity), their rather diffuse localization in many tissues/organs, and the lack of isozyme selectivity of the presently available inhibitors of the sulfonamide/sulfamate class. In fact, among derivatives mentioned above, there are no compounds which selectively inhibit CA isoforms with therapeutic value (inhibition data of 1-25 sulfonamide compounds against all human (h) CA isoforms are provided in Supuran, C. (2008) Nature 7: 168-181.

Isozymes CAIX and CAXII are predominantly found in tumor cells and show a restricted expression in normal tissues. A helpful overview of the limitations of current CAI is provided in Poulsen, Expert Opin. Ther. Patents (2010) 20(6):795-806. It is clear from this review that the use of CAIX inhibitors for cancer and metastasis has not been demonstrated effectively, due to the limitations of the compounds available.

Evidence that certain sulfonamide CAIX inhibitors may indeed show antitumor effects, has been only very recently published (Ahlskog, J. K. J.; Dumelin, C. E.; Trussel, S.; Marlind, J.; Neri, D. *Bioorg. Med. Chem. Lett.* 2009, 19, 4851.) Certain compounds have been disclosed, for example in Maresca et al., PCT publication WO2009089383. Selectivity is an issue, however, as inhibition of housekeeping carbonic anhydrases is contraindicated.

SUMMARY OF THE INVENTION

Provided herein are pharmaceutical compositions for treating hypoxic and metastatic cancer, for the impairment or destruction of cancer stem cells, or for the treatment of any cancer characterized by increased expression of CAIX or CAXII.

One embodiment provides a pharmaceutical composition comprising a pharmaceutically acceptable excipient and a compound of Formula (I)

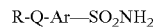

$$R\text{-}Q\text{-}Ar\text{—}SO_2NH_2 \quad \text{Formula (I)}$$

wherein,

R is an aryl, heteroaryl, aralkyl, alkyl or cycloalkyl group, with or without a substituent;

Q is $-L(CH_2)_n-$, wherein n=0, 1 or 2;

L is $-NHC(X)NH-$, $-NHC(S)SNH-$, $-NHC(O)NHC(S)NH-$, or $-SO_2NH-$;

X is O or S; and

Ar is a $C_6$-$C_{10}$ aryl or a heteroaryl that contains at least one heteroatom of oxygen, nitrogen or sulphur.

In certain embodiments, the following compounds are expressly excluded:

4-[(anilinocarbonyl)amino]benzenesulfonamide;
4-{[(Pentafluorophenyl)carbamoyl]amino}benzenesulfonamide;
4-{[(4'-Acetylphenyl)carbamoyl]amino}benzenesulfonamide;
4-{[(4'-Chlorophenyl)carbamoyl]amino}benzenesulfonamide; or
4-{[([4'-(Trifluoromethyl)phenyl]aminocarbonyl)amino]}benzenesulfonamide.

In specific embodiments, the compound of Formula (I) are ureido-sulfonamides. Specifically, Q is $-NHCONH-$, Ar is phenyl, and R is $PhCH_2$, $Ph_2CH$, $4\text{-}FC_6H_4$, $4\text{-}ClC_6H_4$, $4\text{-}BrC_6H_4$, $C_6F_5$, $2\text{-}MeOC_6H_4$, $4\text{-}AcC_6H_4$, $2\text{-i-}PrC_6H_4$, $4\text{-i-}PrC_6H_4$, $4\text{-n-}BuC_6H_4$, $4\text{-n-}BuOC_6H_4$, $4\text{-n-octyl-}C_6H_4$, $4\text{-}NCC_6H_4$, $2\text{-}NCC_6H_4$, $4\text{-}PhOC_6H_4$, $2\text{-}PhC_6H_4$, $3\text{-}O_2NC_6H_4$, $4\text{-}MeO\text{-}2\text{-}MeC_6H_3$, cyclopentyl, indan-5-yl, $3,5\text{-}Me_2C_6H_3$, $4\text{-}CF_3C_6H_4$, or $3,5\text{-}(CF_3)_2C_6H_3$.

Examples of the compounds of Formula (I) include:
4-{[(Benzylamino)carbonyl]amino}benzenesulfonamide (MST-102);
4-{[(Benzhydrylamino)carbonyl]amino}benzenesulfonamide (MST-103);
4-{[(4'-Fluorophenyl)carbamoyl]amino}benzenesulfonamide (MST-104);
4-{[(4'-Bromophenyl)carbamoyl]amino}benzenesulfonamide (MST-105);
4-{[(Pentafluorophenyl)carbamoyl]amino}benzenesulfonamide (MST-107);
4-{[(2'-Methoxyphenyl)carbamoyl]amino}benzenesulfonamide (MST-108);
4-{[(4'-Acetylphenyl)carbamoyl]amino}benzenesulfonamide (MST-109);
4-{[(2'-iso-Propylphenyl)carbamoyl]amino}benzenesulfonamide (MST-110);
4-{[(4'-iso-Propylpheyl)carbamoyl]amino}benzenesulfonamide (MST-111);
4-{[(4'-n-Butylphenyl)carbamoyl]amino}benzenesulfonamide (MST-112);
4-{[(4'-Butoxyphenyl)carbamoyl]amino}benzenesulfonamide (MST-113);
4-{[(4'-n-Octylphenyl)carbamoyl]amino}benzenesulfonamide (MST-114);
4-{[(4'-Cyanophenyl)carbamoyl]amino}benzenesulfonamide (MST-115);
4-{[(2'-Cyanophenyl)carbamoyl]amino}benzenesulfonamide (MST-116);
4-{[(4'-Phenoxyphenyl)carbamoyl]amino}benzenesulfonamide (MST-117);

4-{[(Biphenyl-2'-yl)carbamoyl]amino}benzenesulfonamide (MST-118);
4-{[(3'-Nitrophenyl)carbamoyl]amino}benzenesulfonamide (MST-119);
4-{[(4'-Methoxy-2'-methylphenyl)carbamoyl]amino}benzenesulfonamide (MST-120);
4-[(Cyclopentylcarbamoyl)amino]benzenesulfonamide (MST-122);
4-{[(3',5-Dimethylphenyl)amino]carbonylamino)}benzenesulfonamide (MST-123);
4-{[(4'-Chlorophenyl)carbamoyl]amino}benzenesulfonamide (MST-124);
4-{[(2',3'-Dihydro-1H-inden-5'-ylamino]carbonylamino)}benzenesulfonamide (MST-125);
4-{[([4'-(Trifluoromethyl)phenyl]aminocarbonyl)amino]}benzenesulfonamide (MST-126);
4-{[([3',5'-bis(Trifluoromethyl)phenyl]aminocarbonyl)amino]}benzenesulfonamide (MST-127);
3-(3-(4'-Iodophenyl)ureido)benzenesulfonamide (MST-128);
3-(3-(4'-Fluorophenyl)ureido)benzenesulfonamide (MST-129);
3-(3-(3'-Nitrophenyl)ureido)benzenesulfonamide (MST-130);
3-(3-(4'-Acetylphenyl)ureido)benzenesulfonamide (MST-131);
3-(3-(2'-Isopropylphenyl)ureido)benzenesulfonamide (MST-132);
3-(3-(Perfluorophenyl)ureido)benzenesulfonamide (MST-133);
4-(3-(4'-chloro-2-fluorophenyl)ureido)benzenesulfonamide (MST-134);
4-(3-(4'-bromo-2'-fluorophenyl)ureido)benzenesulfonamide (MST-135);
4-(3-(2'-fluoro-5'-nitrophenyl)ureido)benzenesulfonamide (MST-136);
4-(3-(2',4',5'-trifluorophenyl)ureido)benzenesulfonamide (MST-137);
4-(3-(2'-fluoro-5'-(trifluoromethyl)phenyl)ureido)benzenesulfonamide (MST-138);
4-(3-(2'-fluoro-3'-(trifluoromethyl)phenyl)ureido)benzenesulfonamide (MST-139);
4-(3-(2',3',4'-trifluorophenyl)ureido)benzenesulfonamide (MST-140);
4-(3-(2'-fluorophenyl)ureido)benzenesulfonamide (MST-141);
4-(3-(2',4'-difluorophenyl)ureido)benzenesulfonamide (MST-142);
4-(3-(3'-chlorophenyl)ureido)benzenesulfonamide (MST-143);
4-(3-(2',5'-dichlorophenyl)ureido)benzenesulfonamide (MST-144);
4-(3-(2'-Chloro-5'-nitrophenyl)ureido)benzenesulfonamide (MST-145);
4-(3-(2'-Chloro-4'-(trifluoromethyl)phenyl)ureido)benzenesulfonamide (MST-146);
4-(3-(2',6'-difluorophenyl)ureido)benzenesulfonamide (MST-147); or
4-(3-(perchlorophenyl)ureido)benzenesulfonamide (MST-148).

Further provided are methods of suppressing tumor growth, invasion and/or tumor metastases in a mammal by treating said mammal with the pharmaceutical compositions described herein.

Further provided is a method of reducing breast cancer cells number or mass in a mammal by treating said mammal with the pharmaceutical compositions described herein.

Also provided is a method of depleting cancer stem cells in a mammalian cancer stem cell population using the pharmaceutical compositions described herein.

Also provided is a method of inducing cell death in hypoxic cancer cells using the pharmaceutical compositions described herein.

A mammal so treated according to the present disclosure may be treated with additional chemotherapeutic or other anticancer agents. Any cancer or tumor or cell population treated herein may express CAIX or CAXII over and above the normal level for non-cancerous like-originated tissues.

The tumors treated may be of the breast, lung, pancreatic, renal, prostate, cervical, colorectal cancer, or glioblastoma according to certain embodiments. The use of the compositions to treat a mammal having cancer or a tumor may reduce or eliminate metastases.

The mammal may be human.

There is further provided a compound comprising formula (I)

$$R-Q-Ar-SO_2NH_2$$

wherein,

R is an aryl, heteroaryl, aralkyl, alkyl or cycloalkyl group, with or without a substituent;

Q is -L(CH$_2$)$_n$—, where n=0, 1 or 2;

L is —NHC(X)NH—, —NHC(S)SNH—, —NHC(O)NHC(S)NH—, or —SO$_2$NH—;

X is O or S; and

Ar is a C$_{6-10}$ aryl or a heteroaryl group that contains at least one heteroatom of oxygen, nitrogen or sulphur.

In certain embodiments, the following compounds are expressly excluded:
4-[(anilinocarbonyl)amino]benzenesulfonamide;
4-{[(Pentafluorophenyl)carbamoyl]amino}benzenesulfonamide;
4-{[(4'-Acetylphenyl)carbamoyl]amino}benzenesulfonamide;
4-{[(4'-Chlorophenyl)carbamoyl]amino}benzenesulfonamide;
4-{[([4'-(Trifluoromethyl)phenyl]aminocarbonyl)amino]}benzenesulfonamide;
3-(3-(4'-Iodophenyl)ureido)benzenesulfonamide;
3-(3-(4'-Fluorophenyl)ureido)benzenesulfonamide;
3-(3-(3'-Nitrophenyl)ureido)benzenesulfonamide;
3-(3-(4'-Acetylphenyl)ureido)benzenesulfonamide;
3-(3-(2'-Isopropylphenyl)ureido)benzenesulfonamide; or
3-(3-(Perfluorophenyl)ureido)benzenesulfonamide.

In certain embodiments, Q may be —NHCONH—, Ar is phenyl, and R may be PhCH$_2$, Ph$_2$CH, 4-FC$_6$H$_4$, 4-ClC$_6$H$_4$, 4-BrC$_6$H$_4$, C$_6$F$_5$, 2-MeOC$_6$H$_4$, 4-AcC$_6$H$_4$, 2-i-PrC$_6$H$_4$, 4-i-PrC$_6$H$_4$, 4-n-BuC$_6$H$_4$, 4-n-BuOC$_6$H$_4$, 4-n-octyl-C$_6$H$_4$, 4-NCC$_6$H$_4$, 2-NCC$_6$H$_4$, 4-PhOC$_6$H$_4$, 2-PhC$_6$H$_4$, 3-O$_2$NC$_6$H$_4$, 4-MeO-2-MeC$_6$H$_3$, Cyclopentyl, Indan-5-yl, 3,5-Me$_2$C$_6$H$_3$, 4-CF$_3$C$_6$H$_4$, or 3,5-(CF$_3$)$_2$C$_6$H$_3$.

Preferred compounds include the following:

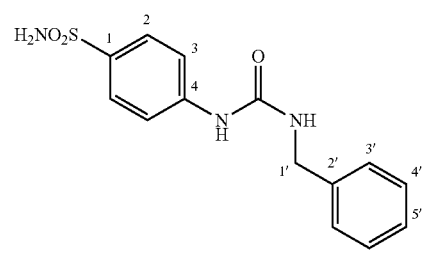

MST-102

MST-103
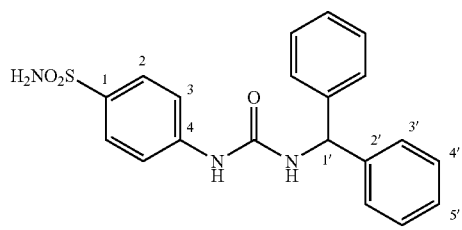
MST-104
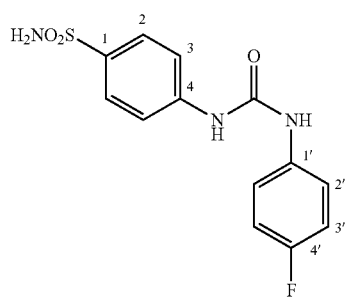
MST-105
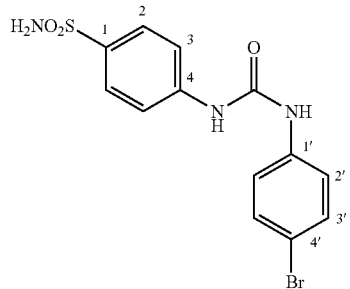
MST-107
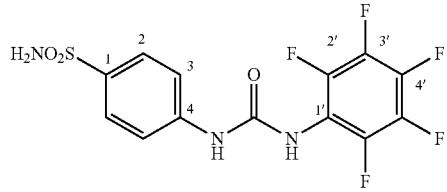
MST-108
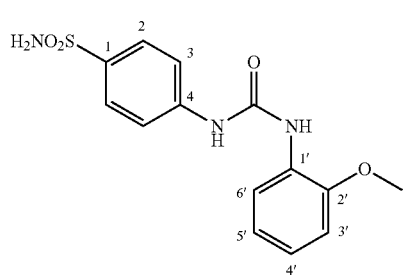
MST-109
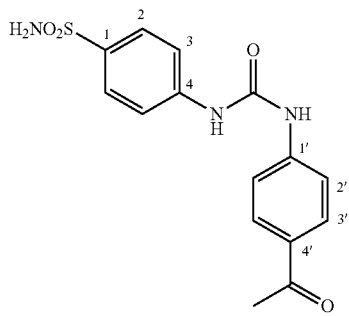
MST-110
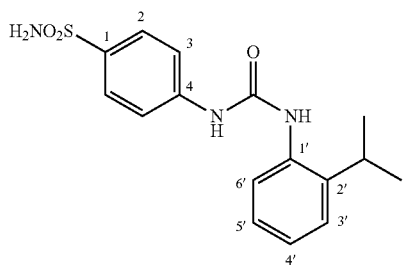
MST-111
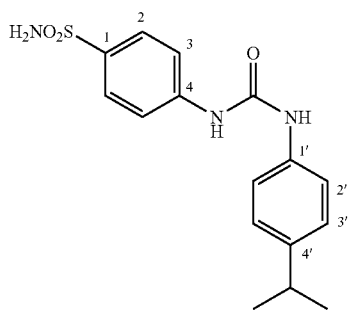
MST-112
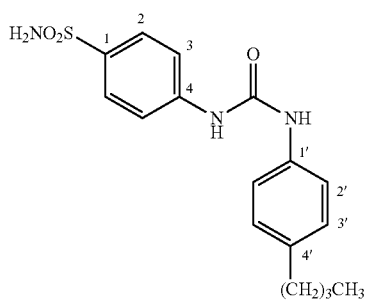
MST-113
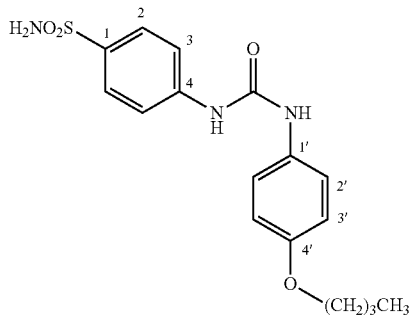

MST-114
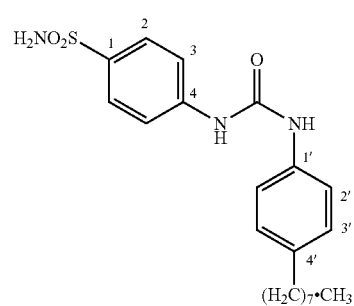
MST-115
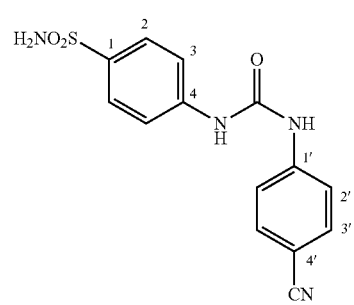
MST-116
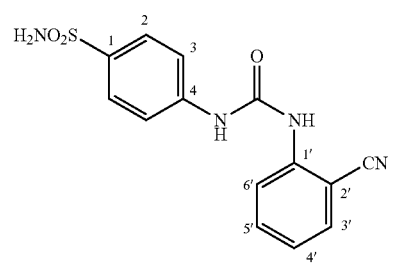
MST-117
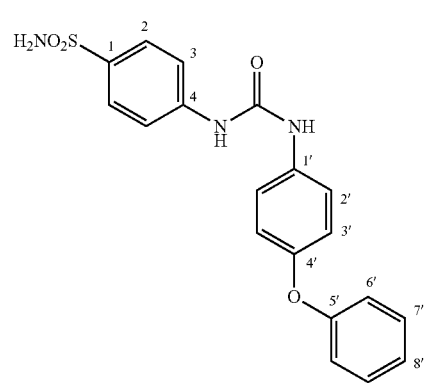
MST-118
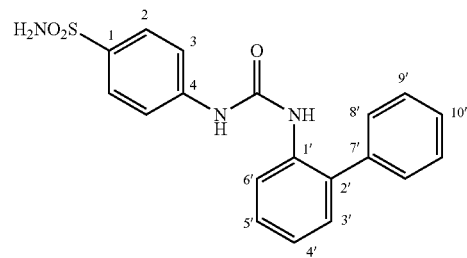
MST-119
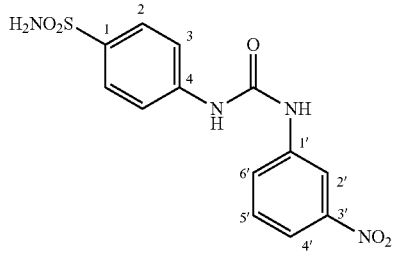
MST-120
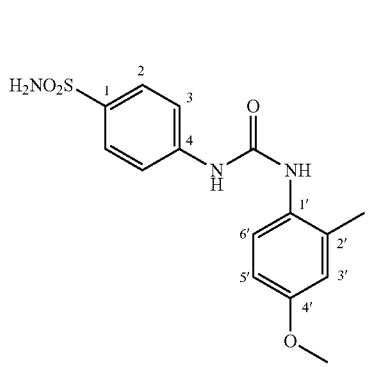
MST-122
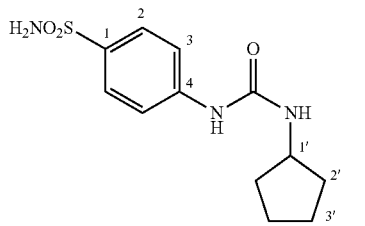
MST-123
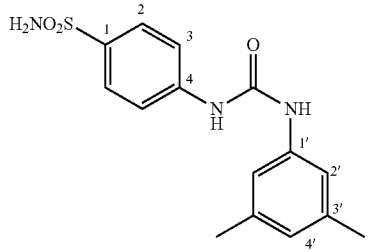
MST-124
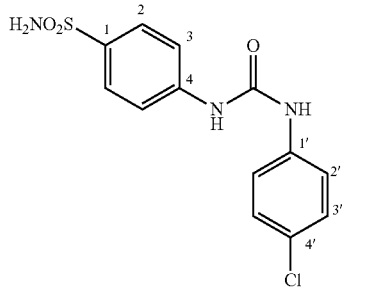

MST-125
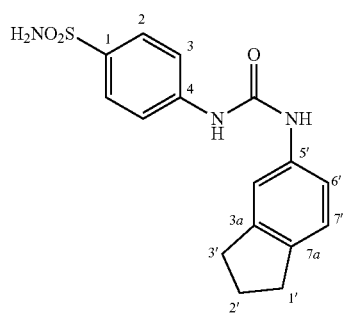
MST-126
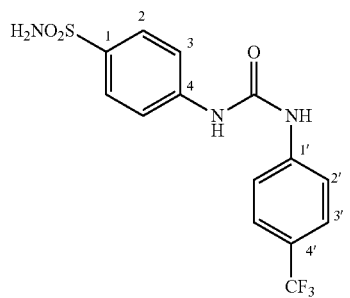
MST-127
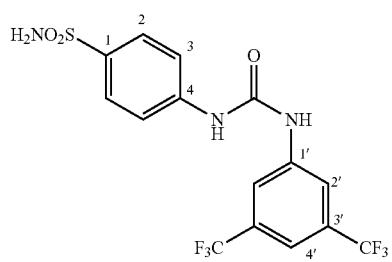
MST-128
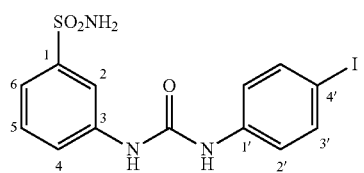
MST-129
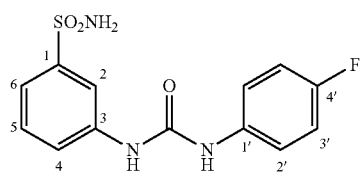
MST-130
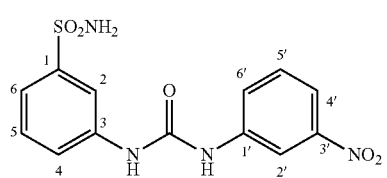
MST-131
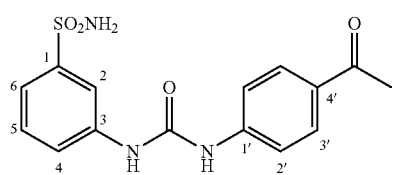
MST-132
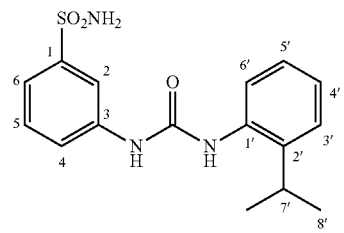
MST-133
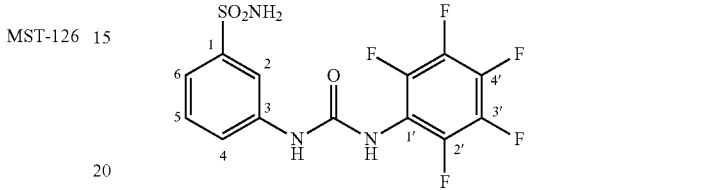
MST-134
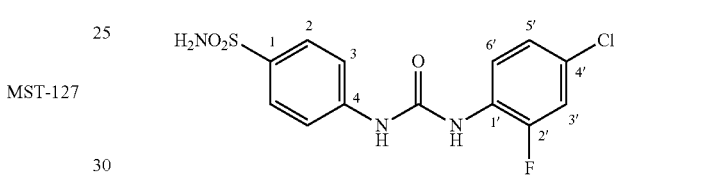
MST-135
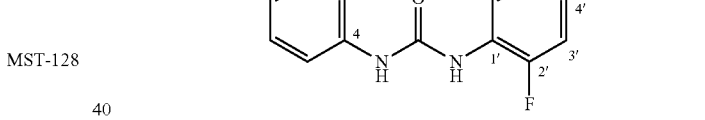
MST-136
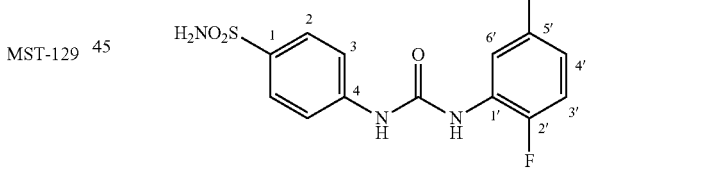
MST-137
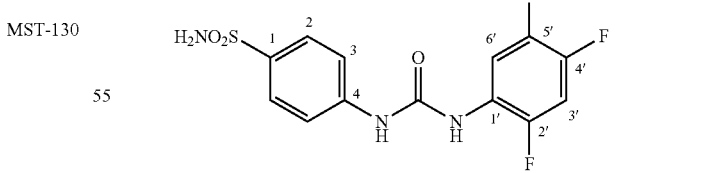
MST-138
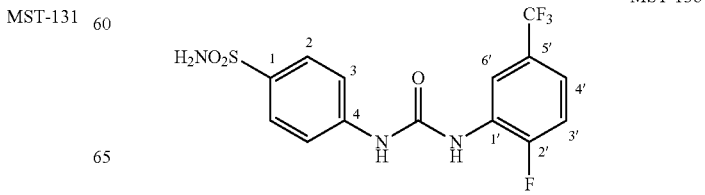

The pharmaceutical compositions described herein are characterized in that they inhibit the activity of tumor-related CAIX and CAXII to a greater degree than they inhibit the activity of CAI and CAII in vitro.

There are further provided compositions and their use to inhibit invasion, and/or induce cell death of human breast cancer cells in hypoxia.

There are further provided compositions and their use to impair maintenance of breast cancer stem cells through the inhibition of CAIX activity.

There are further provided compositions and their use to deplete the cancer stem cell population in human breast cancer by inhibiting CAIX activity.

There is also provided a method of treating metastatic or hypoxic cancer with MST-017, MST-114, MST-119, MST-104, or MST-130.

BRIEF DESCRIPTION OF THE DRAWINGS

FIG. 9 shows (A) the chemical structure of MST-017, or previously identified "CAI-17" (Supuran, C. 2008, Nature. Vol 7: 168-181), (B) Cells were cultured for 72 h in the presence of 10 uM MST-017. Shown are representative images of the FITC-tagged inhibitor bound to the cell lines in the indicated conditions. (C) is a graphing of the change in extracellular pH for cells cultured for 72 h with or without MST-017 (400, 600 and 400 uM for the 4T1, 66cl4 and 67NR cells, respectively). n=3. The mean changes in extracellular pH ±s.e.m. are shown.

DETAILED DESCRIPTION

Figure 1:
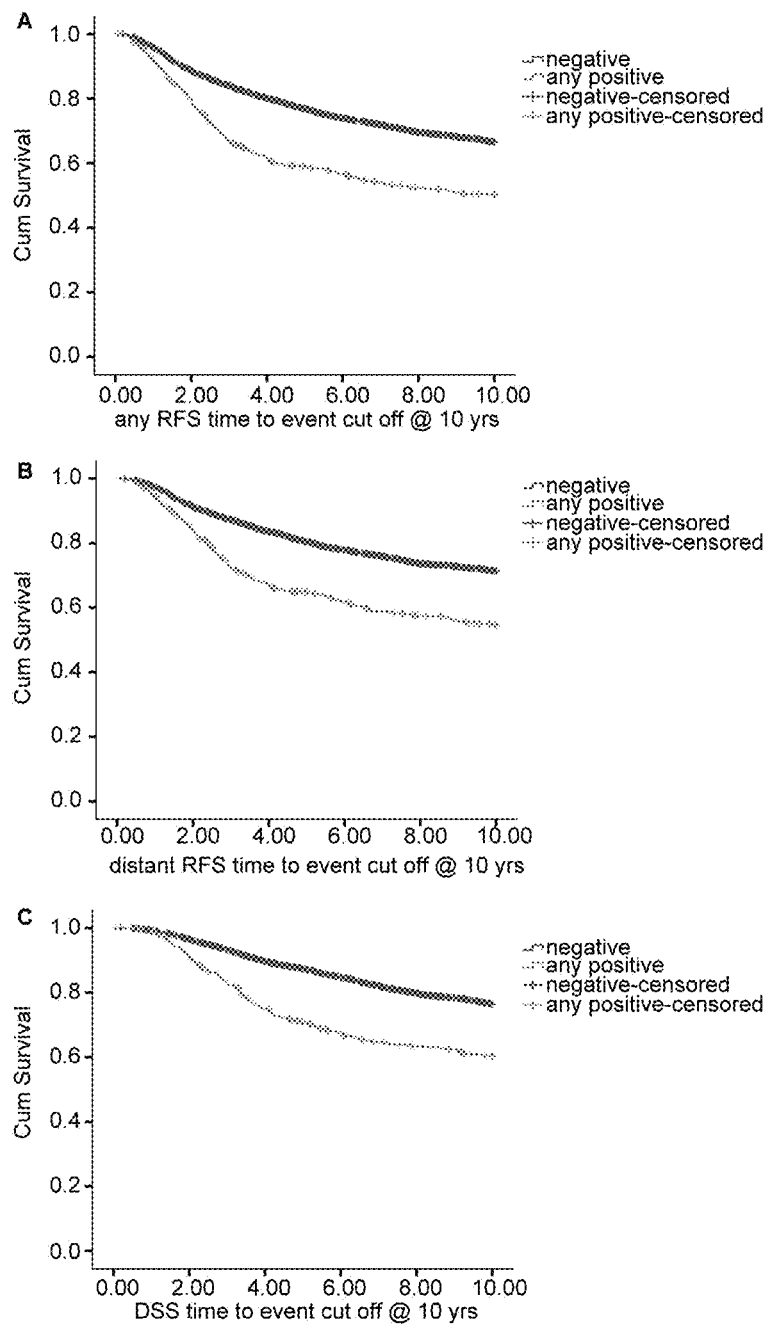
FIG. 1 shows In Kaplan-Meier analyses of CAIX expression association with relapse free survival (A), distant relapse free survival (B) and breast cancer specific survival (C), achieving very high levels of statistical significance ($p<10-17$, $p<10-16$, and $p<10-13$, respectively). The 10 year distant relapse free survival and breast cancer specific survival rates in the CAIX positive versus CAIX negative groups were 57% compared to 73%, and 62% compared to 78%, respectively. In multivariate analyses, including all standard prognostic variables and biological subtypes, CAIX expression remained a strong independent poor prognostic factor with a hazard ratio of 1.4.

Ureido-sulfonamides compositions suitable for the treatment of metastatic cancer are synthesized and utilized as herein described. In certain embodiments, the pharmaceutical composition comprises a pharmaceutically acceptable excipient and a compound of Formula (I)

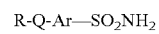

wherein R may be an aryl, heteroaryl, aralkyl alkyl or cycloalkyl group, any of the above groups may be further substituted, namely, they may be with or without a substituent;

Q may be -L(CH$_2$)$_n$—, where n=0, 1 or 2 and L may be —NHC(X)NH—, —NHC(S)SNH—, —NHC(O)NHC(S)NH—, or —SO$_2$NH—, wherein X may be O or S; and Ar may be a C$_6$-C$_{10}$ aryl or a heteroaryl group that contains at least one heteroatom of oxygen, nitrogen or sulphur.

In certain embodiments, Q may be —NHC(O)NH—, Ar may be phenyl and R may be PhCH$_2$, Ph$_2$CH, 4-FC$_6$H$_4$, 4-ClC$_6$H$_4$, 4-BrC$_6$H$_4$, C$_6$F$_5$, 2-MeOC$_6$H$_4$, 4-AcC$_6$H$_4$, 2-i-PrC$_6$H$_4$, 4-i-PrC$_6$H$_4$, 4-n-BuC$_6$H$_4$, 4-n-BuOC$_6$H$_4$, 4-n-octyl-C$_6$H$_4$, 4-NCC$_6$H$_4$, 2-NCC$_6$H$_4$, 4-PhOC$_6$H$_4$, 2-PhC$_6$H$_4$, 3-O$_2$NC$_6$H$_4$, 4-MeO-2-MeC$_6$H$_3$, Cyclopentyl, Indan-5-yl, 3,5-Me$_2$C$_6$H$_3$, 4-CF$_3$C$_6$H$_4$, or 3,5-(CF$_3$)$_2$C$_6$H$_3$.

Representative compounds include:

4-{[(Benzylamino)carbonyl]amino}benzenesulfonamide (MST-102);
4-{[(Benzhydrylamino)carbonyl]amino}benzenesulfonamide (MST-103);
4-{[(4'-Fluorophenyl)carbamoyl]amino}benzenesulfonamide (MST-104);
4-{[(4'-Bromophenyl)carbamoyl]amino}benzenesulfonamide (MST-105);
4-{[(Pentafluorophenyl)carbamoyl]amino}benzenesulfonamide (MST-107);
4-{[(2'-Methoxyphenyl)carbamoyl]amino}benzenesulfonamide (MST-108);
4-{[(4'-Acetylphenyl)carbamoyl]amino}benzenesulfonamide (MST-109);
4-{[(2'-iso-Propylphenyl)carbamoyl]amino}benzenesulfonamide (MST-110);
4-{[(4'-iso-Propylphenyl)carbamoyl]amino}benzenesulfonamide (MST-111);
4-{[(4'-n-Butylphenyl)carbamoyl]amino}benzenesulfonamide (MST-112);
4-{[(4'-Butoxyphenyl)carbamoyl]amino}benzenesulfonamide (MST-113);
4-{[(4'-n-Octylphenyl)carbamoyl]amino}benzenesulfonamide (MST-114);
4-{[(4'-Cyanophenyl)carbamoyl]amino}benzenesulfonamide (MST-115);
4-{[(2'-Cyanophenyl)carbamoyl]amino}benzenesulfonamide (MST-116);
4-{[(4'-Phenoxyphenyl)carbamoyl]amino}benzenesulfonamide (MST-117);
4-{[(Biphenyl-2'-yl)carbamoyl]amino}benzenesulfonamide (MST-118);
4-{[(3'-Nitrophenyl)carbamoyl]amino}benzenesulfonamide (MST-119);
4-{[(4'-Methoxy-2'-methylphenyl)carbamoyl]amino}benzenesulfonamide (MST-120);
4-[(Cyclopentylcarbamoyl)amino]benzenesulfonamide (MST-122);
4-{([(3',5'-Dimethylphenyl)amino]carbonylamino)}benzenesulfonamide (MST-123);
4-{[(4'-Chlorophenyl)carbamoyl]amino}benzenesulfonamide (MST-124);
4-{[(2',3'-Dihydro-1H-inden-5'-ylamino]carbonylamino)}benzenesulfonamide (MST-125);
4-{[([4'-(Trifluoromethyl)phenyl]aminocarbonyl)amino]}benzenesulfonamide (MST-126);
4-{[([3',5'-bis(Trifluoromethyl)phenyl]aminocarbonyl)amino]}benzenesulfonamide (MST-127);
3-(3-(4'-Iodophenyl)ureido)benzenesulfonamide (MST-128);
3-(3-(4'-Fluorophenyl)ureido)benzenesulfonamide (MST-129);
3-(3-(3'-Nitrophenyl)ureido)benzenesulfonamide (MST-130);
3-(3-(4'-Acetylphenyl)ureido)benzenesulfonamide (MST-131);
3-(3-(2'-Isopropylphenyl)ureido)benzenesulfonamide (MST-132);
3-(3-(Perfluorophenyl)ureido)benzenesulfonamide (MST-133);
4-(3-(4'-chloro-2-fluorophenyl)ureido)benzenesulfonamide (MST-134);
4-(3-(4'-bromo-2'-fluorophenyl)ureido)benzenesulfonamide (MST-135);
4-(3-(2'-fluoro-5'-nitrophenyl)ureido)benzenesulfonamide (MST-136);
4-(3-(2',4',5'-trifluorophenyl)ureido)benzenesulfonamide (MST-137);
4-(3-(2'-fluoro-5'-(trifluoromethyl)phenyl)ureido)benzenesulfonamide (MST-138);
4-(3-(2'-fluoro-3'-(trifluoromethyl)phenyl)ureido)benzenesulfonamide (MST-139);
4-(3-(2',3',4'-trifluorophenyl)ureido)benzenesulfonamide (MST-140);
4-(3-(2'-fluorophenyl)ureido)benzenesulfonamide (MST-141);
4-(3-(2',4'-difluorophenyl)ureido)benzenesulfonamide (MST-142);
4-(3-(3'-chlorophenyl)ureido)benzenesulfonamide (MST-143);
4-(3-(2',5'-dichlorophenyl)ureido)benzenesulfonamide (MST-144);
4-(3-(2'-Chloro-5'-nitrophenyl)ureido)benzenesulfonamide (MST-145);
4-(3-(2'-Chloro-4'-(trifluoromethyl)phenyl)ureido)benzenesulfonamide (MST-146);
4-(3-(2',6'-difluorophenyl)ureido)benzenesulfonamide (MST-147); or
4-(3-(perchlorophenyl)ureido)benzenesulfonamide (MST-148).

As used herein, the C$_6$-C$_{10}$ aryl group means phenyl or 1, or 2-naphthyl, and a heteroaryl group means a C$_2$-C$_{12}$ heterocyclic aromatic compound that contains at least one heteroatom of oxygen, nitrogen or sulphur. Furthermore, 1,3,4-thiadiazole is a preferred heterocyclic group.

Further, an alkyl groups means a straight chain or branched, noncyclic, nonaromatic aliphatic hydrocarbon moiety. A cycloalkyl means a cyclic hydrocarbon moiety. An aralkyl means an alkyl moiety substituted with an aryl. Examples of aralkyl includes benzyl (PhCH$_2$—) and diphenylmethyl (Ph$_2$CH—).

The term "substituted" in the context of alkyl, aryl, heteroaryl means that at least one hydrogen atom of the alky, aryl, and heteroaryl moiety is replaced with a substituent, i.e. a further chemical moiety. Suitable substituents include, for example, halogen (F, Cl, Br, I), cyano, alkyl, alkoxy (alkyl-O—), aryloxy (aryl-O—), nitro (—NO$_2$), cycloalkyl, haloalkyl (alkyl substituted by one or more halogens, e.g., trifluoroalkyl), heteroaryl, and the like.

There is further provided compounds of formula (I), wherein the compounds inhibits the activity of tumor-related CAIX and CAXII to a greater degree than it inhibits the activity of CAI and CAII as measured in vitro.

A further embodiment provides a process for the preparation of the compounds of formula (I). One preferred reaction is carried out between a compound of formula R—NCX, wherein R and X are as defined above, and a compound of formula NH$_2$—Ar—SO$_2$NH$_2$ or NH$_2$CSNH—Ar—SO$_2$NH$_2$, wherein Ar as defined above.

Another preferred reaction is the oxidative thiocarbamylation of a compound of formula NH$_2$—Y—SO$_2$NH$_2$ with sodium/potassium N,N-dimethyl-/diethyldithiocarbamate, wherein Y is the group of —(CH$_2$)$_n$Ar—, n=0, 1, 2 and Ar is a C$_6$-C$_{10}$ aromatic or a heteroaromatic group that contains at least one heteroatom of oxygen, nitrogen or sulphur.

Reaction conditions are those known to those skilled in the art, see for example, A. Scozzafava and C. T. Supuran Bioorg. Med. Chem. Lett. 2000, 10, 1117-1120; C. T. Supuran; F. Briganti; S. Tilli; W. R. Chegwidden; A. Scozzafava Bioorg. Med. Chem. 2001, 9, 703-714; C. T. Supuran; A. Scozzafava; B. C. Jurca; M. A. Hies Eur. J. Med. Chem. 1998, 33, 83-93.

The following scheme shows an example of a process that may be used to prepare compounds according to the present disclosure.

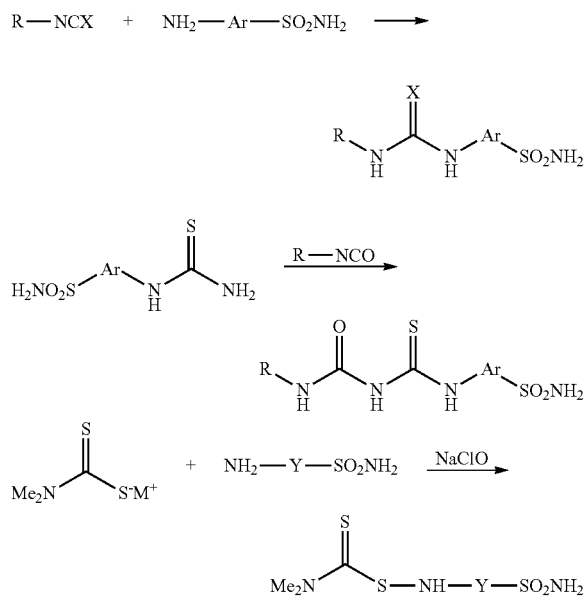

The compounds according to the present disclosure are selective CAIX and CAXII inhibitors. Thus, there is further provided compounds of Formula (I), wherein the compounds inhibit the activity of tumor-related CAIX and CAXII to a greater degree than they inhibits the activity of CAI and CAII as measured in vitro. These compounds are useful in methods to reduce the growth of human breast cancer, to inhibit invasion by breast cancer cells under hypoxic conditions typical in solid tumors, to kill human breast cancer cells in hypoxia, and to deplete cancer stem cell populations.

Cancer stem cells (CSCs) are defined as a subpopulation of cancer cells that have the properties of self renewal potential, the ability to give rise to non-CSC progeny, and greatly enhanced tumor-initiating potential relative to other cancer cells within the tumor (Chaffer and Weinberg, (2011) Science 331:1559-1564; Clevers, (2011) Nat. Med. 17: 313-319; Hanahan and Weinberg, (2011) Cell. 144: 646-674). CSCs are defined experimentally as cells that have the ability to seed new tumors when implanted into an appropriate animal host (Chaffer and Weinberg, 2011; Hanahan and Weinberg, 2011). They are believed to be a component of cancer therapy resistance.

TABLE 1

INHIBITION OF HCAI, HCAII (CYTOSOLIC ISOFORMS) AND HCAIX AND HCAXII (TRANSMEMBRANE, TUMOR-ASSOCIATED ENZYMES) WITH UREIDO SULFONAMIDES. MST-101 TO MST-127.

$$R-\overset{O}{\underset{H}{N}}-\overset{}{\underset{H}{N}}-C_6H_4-SO_2NH_2$$

| Informal Name | R | $K_I$ (nM) Activity | | | |
|---|---|---|---|---|---|
| | | hCAI | hCAII | hCAIX | hCAXII |
| MST-101 | Ph | 760 | 3730 | 575 | 67.3 |
| MST-102 | $PhCH_2$ | 92 | 2200 | 41.4 | 49.5 |
| MST-103 | $Ph_2CH$ | 83 | 3725 | 58.8 | 64.5 |
| MST-104 | $4\text{-}FC_6H_4$ | 5080 | 9640 | 45.1 | 4.5 |
| MST-105 | $4\text{-}BrC_6H_4$ | 1465 | 1290 | 69.3 | 7.9 |
| MST-106 | $4\text{-}IC_6H_4$ | 5500 | 2634 | 24.5 | 4.3 |
| MST-107 | $C_6F_5$ | 2395 | 5055 | 5.4 | 5.1 |
| MST-108 | $2\text{-}MeOC_6H_4$ | 92 | 4070 | 465 | 61.2 |
| MST-109 | $4\text{-}AcC_6H_4$ | 388 | 1060 | 5.4 | 4.6 |
| MST-110 | $2\text{-}i\text{-}PrC_6H_4$ | 9.0 | 3.3 | 0.5 | 4.2 |
| MST-111 | $4\text{-}i\text{-}PrC_6H_4$ | 4330 | 5005 | 541 | 49.7 |
| MST-112 | $4\text{-}n\text{-}BuC_6H_4$ | 5530 | 2485 | 376 | 28.5 |
| MST-113 | $4\text{-}n\text{-}BuOC_6H_4$ | 11.3 | 2.1 | 0.8 | 2.5 |
| MST-114 | $4\text{-}n\text{-}octyl\text{-}C_6H_4$ | 536 | 9600 | 47.1 | 52.8 |
| MST-115 | $4\text{-}NCC_6H_4$ | 57.0 | 64.7 | 6.0 | 6.5 |
| MST-116 | $2\text{-}NCC_6H_4$ | 10.9 | 2.4 | 0.3 | 4.6 |
| MST-117 | $4\text{-}PhOC_6H_4$ | 604 | 85 | 69.1 | 7.1 |
| MST-118 | $2\text{-}PhC_6H_4$ | 1170 | 9.7 | 65.7 | 65.1 |
| MST-119 | $3\text{-}O_2NC_6H_4$ | 23.4 | 15 | 0.9 | 5.7 |
| MST-120 | $4\text{-}MeO\text{-}2\text{-}MeC_6H_3$ | 89.2 | 3310 | 73.3 | 6.0 |
| MST-121 | 9H-fluoren-2-yl | 1700 | 908 | 102 | 55.4 |
| MST-122 | Cyclopentyl | 470 | 2265 | 7.3 | 7.0 |
| MST-123 | $3,5\text{-}Me_2C_6H_3$ | 6530 | 1765 | 6.9 | 6.2 |
| MST-124 | $4\text{-}ClC_6H_4$ | 2150 | 781 | 58 | 5.3 |
| MST-125 | Indan-5-yl | 9.8 | 8.9 | 7.0 | 2.5 |
| MST-126 | $4\text{-}CF_3C_6H_4$ | 9.7 | 1150 | 6.2 | 2.3 |
| MST-127 | $3,5\text{-}(CF_3)_2C_6H_3$ | 3690 | 75 | 53 | 39 |

The compounds disclosed herein are useful for the preparation of medicaments as well as in a method for the treatment of a hypoxic tumor that has CAIX or CAXII highly overexpressed. "Overexpression" means the excessive expression of a gene, usually by producing too much of its effect or product. The medicaments have inhibiting action toward CAIX, and are particularly effective for reversing acidification of a hypoxic tumor and its surrounding environment.

The compounds disclosed herein are also capable of impairing and/or eradicating cancer stem cells. Cancer stem cells are thought to be a basis of resistance by tumors to traditional therapeutic agents or techniques, such as chemotherapeutics or radiation.

In most cancer therapy, multiple agents with complementary modalities of action are typically used as part of a chemotherapy "cocktail." It is anticipated that the compositions disclosed herein may be used in such cocktail that may contain one or more additional antineoplastic agents depending on the nature of the cancer being treated. Other chemotherapeutic agents, such as antimetabolites (i.e., 5-fluorouracil, floxuradine, thioguanine, cytarabine, fludarabine, 6-mercaptopurine, methotrexate, gemcitabine, capacitabine, pentostatin, trimetrexate, or cladribine); DNA cross-linking and alkylating agents (i.e., cisplatin, carboplatin, streptazoin, melphalan, chlorambucil, carmustine, methclorethamine, lomustine, bisulfan, thiotepa, ifofamide, or cyclophosphamide); hormonal agents (i.e., tamoxifen, roloxifen, toremifene, anastrozole, or letrozole); antibiotics (i.e., plicamycin, bleomycin, mitoxantrone, idarubicin, dactinomycin, mitomycin, doxorubicin or daunorubicin); immunomodulators (i.e., interferons, IL-2, or BCG); antimitotic agents (i.e., estramustine, paclitaxel, docetaxel, vinblastine, vincristine, or vinorelbine); topoisomerase inhibitors (i.e., topotecan, irinotecan, etoposide, or teniposide.); and other agents (i.e., hydroxyurea, trastuzumab, altretamine, retuximab, L-asparaginase, or gemtuzumab ozogamicin) may therefor be used in combination with the compositions disclosed herein.

The molecules may be compounded with known pharmaceutical excipients such as salts, water, lipids, and/or simple sugars to arrive at a formulation suitable for injection, topical application, or ingestion.

Pharmaceutical formulation involves developing a preparation of the compound which is both stable and acceptable for human use. Formulations of the compounds will have been tested to ensure that the drug is compatible with any solubilizing, stabilizing, lyophilizing, or hydrating agents.

The design of any formulation involves the characterization of a drug's physical, chemical, and mechanical properties in order to choose what other ingredients should be used in the preparation.

Particle size, polymorphism, pH, and solubility, as all of these can influence bioavailability and hence the activity of a drug. The drug must be combined with inactive additives by a method which ensures that the quantity of drug present is consistent in each dosage unit e.g. each tablet.

It is unlikely that formulation studies will be complete by the time clinical trials commence. This means that simple preparations are developed initially for use in phase I clinical trials. Proof the long-term stability of these formulations is not required, as they will be used (tested) in a matter of days.

By the time phase III clinical trials are reached, the formulation of the drug should have been developed to be close to the preparation that will ultimately be used in the market. Stability studies are carried out to test whether temperature, humidity, oxidation, or photolysis (ultraviolet light or visible light) have any effect, and the preparation is analyzed to see if any degradation products have been formed.

In one embodiment, the compounds are formulated in polyethyleneglycol with ethanol and saline. In one particular embodiment, the formulation consists of 37.5% PEG400, 12.5% ethanol and 50% saline.

As used in this document, tumor may be taken to mean any primary or metastatic cancer, hypoxic tumor tissue, or malignant growth. Any tumor susceptible to hypoxia and/or metastases, particularly breast, lung, renal cancers, cervical, pancreatic, colorectal, glioblastoma, prostate and ovarian cancer may be treated according to embodiments disclosed herein. Methods are available to determine additional suitable cancer types for treatment with the compositions disclosed herein, namely, methods are available and known to one of skill in the art for detecting hypoxic tissues. See, for example, U.S. Pat. Nos. 5,401,490 and 5,843,404 which disclose methods of detecting hypoxia or hypoxic tissues. Any of these techniques or others known to those skilled in the art may be used to identify hypoxic tissues.

Tumors susceptible to treatment will have elevated levels of CAIX or CAXII with respect to normal tissue. Isozymes CAIX and CAXII are predominantly found in tumor cells and show a restricted expression in normal tissues. It has been recently proven that by efficiently hydrating carbon dioxide to protons and bicarbonate, these CAs contribute significantly to the extracellular acidification of solid tumors, whereas their inhibition reverses this phenomenon to a certain extent. CAIX and CAXII are overexpressed in many such tumors in response to the hypoxia inducible factor (HIF) pathway.

As demonstrated in the data, CAIX and CAXII are associated with hypoxia and metastases. Thus a hypoxic and metastatic tumor would not need to be tested to prove elevated levels of CAIX and CAXII to indicate treatment using the compounds disclosed herein because of the data already supporting the supposition. However, U.S. Pat. No. 7,378,091 by Gudas et al. discloses CAIX antibodies useful in detection and diagnosis. Antibodies against CAXII, as well as RNA probes, can be used to assess overexpression of CAXII in biopsied tumor samples.

CA XII is also assessed in Battke et al., (2011) Cancer Immunol Immunother. May; 60(5):649-58.

Tumor growth, persistence and/or spread may be said to be suppressed by compounds disclosed herein, or by their use in treating mammals so afflicted. "Suppression" in this application may mean induction of regression, inhibition of growth, and inhibition of spread, especially as these terms relate to tumors and cancers suffered by mammals, particularly humans.

Typical chemotherapeutic agents including, but not limited to docetaxel, vinca alkaloids, mitoxanthrone, cisplatin, paclitaxel, 5-FU, Herceptin, Avastin, Gleevec may be used in combination with the compounds disclosed herein. Similarly, radiation therapy may be combined with administration schedules including the compounds disclosed herein.

When surgical intervention is performed, the compounds and compositions disclosed herein may be used preoperatively, perioperatively, or post-operatively. Dosage is typically determined by dosing schemes which use patient size and weight to calculate the patient's body surface area, which correlates with blood volume, to determine initial dosing. Starting dosages are generally worked out during clinical testing of therapeutic compounds.

The background and current approaches for the clinical approach to tumor treatment may be found in Takimoto C H, Calvo E. "Principles of Oncologic Pharmacotherapy" in Pazdur R, Wagman L D, Camphausen K A, Hoskins W J (Eds) Cancer Management: A Multidisciplinary Approach. 11 ed. 2008, which is freely available at http://www.cancer-network.com/cancer-management-11/chapter03/article/10165/1402628.

The following examples are used to illustrate aspects disclosed herein, but the embodiments are not intended to be limited by these illustrations.

EXAMPLES

Example 1

Preparations of Specific Embodiments

Compounds MST-101 to MST-127 Inclusive

General Procedure for the Preparation of Compounds of Formula (I)

Methods in chemistry: $^1$H, $^{13}$C and $^{19}$F spectra were recorded using a Bruker Advance 111400 MHz spectrometer. The chemical shifts are reported in parts per million (ppm) and the coupling constants (J) are expressed in Hertz (Hz). Infrared spectra were recorded on a Perkin Elmer Spectrum R XI spectrometer as solids on KBr plates. Melting points (m.p.) were measured in open capillary tubes, unless otherwise stated, using a Buchi Melting Point B-540 melting point apparatus, and are uncorrected. Thin layer chromatography (TLC) was carried out on Merck silica gel 60 $F_{254}$ aluminum backed plates. Elution of the plates was carried out using ethyl acetate—petroleum ether as eluting system. Visualization was achieved with UV light at 254 nm, by dipping into a ninhydrin TLC stain solution and heating with a hot air gun. Flash column chromatography was carried out using silica gel (obtained from Aldrich Chemical Co., Milan, Italy) as the adsorbent. The crude product was introduced into the column as a solution in the same elution solvent system. Solvents and chemicals were used as supplied from Aldrich Chemical Co., Milan, Italy.

4-Aminobenzenesulfonamide (2.9 mmole) was dissolved in acetonitrile (20-30 mL) and then treated with a stoichiometric amount of an isocyanide. The mixture was stirred at r.t. or heated at 50° C. for 2 hours, until completion (TLC monitoring). The heavy precipitate formed was filtered-off, washed with diethyl ether and dried under vacuum.

4-[(anilinocarbonyl)amino]benzenesulfonamide (MST-101)

4-Aminobenzenesulfanilamide (0.50 g; 2.90 mmols) was treated with phenyl isocyanate (0.23 g; 2.90 mmols) and the reaction was stirred at r.t. for 1 day, treated as described in the general procedure previously reported to give MST-101 as a white solid in 43.7% yield. m. p. 233-235° C. (Lie); silica gel TLC $R_f$ 0.63 (ethyl acetate/petroleum ether 33%); $v_{max}$ (KBr) cm$^{-1}$, 3340 (N—H urea), 1656 (C=O urea), 1595 (aromatic); $\delta_H$ (400 MHz, DMSO-d$_6$) 7.00 (1H, tt, J 7.4, 0.8, 4'-H), 7.20 (2H, s, SO$_2$NH$_2$), 7.29 (2H, dd, J 8.2, 0.8, 2×3'-H), 7.47 (2H, dd, J 8.2, 1.2, 2×2'-H), 7.61 (2H, d, J 9.0, 2×3'-H), 7.73 (2H, d, J 9.0, 2×2'-H), 8.82 (1H, s, NH), 9.09 (1H, s, NH); $\delta_C$ (100 MHz, DMSO-d$_6$) 153.2 (C=O urea), 143.8, 140.2, 137.8, 129.8, 127.7, 123.1, 119.4, 118.4.

4-{[(Benzylamino)carbonyl]amino}benzenesulfonamide (MST-102)

4-Aminobenzenesulfanilamide (0.50 g; 2.90 mmols) was treated with benzyl isocyanate (0.39 g; 2.90 mmols) and the reaction was stirred at r.t. for 4 h, treated as described in the general procedure previously reported to give MST-102 as a white solid in 42.3% yield. m.p. 194-196° C.; silica gel TLC $R_f$ 0.58 (ethyl acetate/petroleum ether 33%); $v_{max}$ (KBr) cm$^{-1}$, 3313 (N—H urea), 1674 (C=O urea), 1591 (aromatic); $\delta_H$ (400 MHz, DMSO-d$_6$) 4.35 (2H, d, J 6.0, 1'-H$_2$), 6.81 (1H, t, J 6.0, NH), 7.19 (2H, s, SO$_2$NH$_2$), 7.28 (1H, tt, J 6.8 2.0, 5'-H), 7.35 (4H, m, 2×3'-H, 2×4'-H), 7.59 (2H, d, J 9.0, 2×3'-H), 7.71 (2H, d, J 9.0, 2×2'-H), 9.0 (1H, s, NH); $\delta_C$ (100 MHz, DMSO-d$_6$) 155.8 (C=O urea), 144.5, 141.0, 137.1, 129.3, 128.1, 127.8, 127.7, 117.8, 43.7 (C-1').

4-{[(Benzhydrylamino)carbonyl]amino}benzenesulfonamide (MST-103)

4-Aminobenzenesulfanilamide (0.50 g; 2.90 mmols) was treated with benzhydryl isocyanate (0.61 g; 2.90 mmols) and the reaction was stirred for 2 h, treated as described in the general procedure previously reported to give MST-103 as a white solid in 42.4% yield. m.p. 235-236° C.; silica gel TLC $R_f$ 0.76 (ethyl acetate/petroleum ether 33%); $v_{max}$ (KBr) cm$^{-1}$, 3338 (N—H urea), 1696 (C=O urea), 1592 (aromatic); $\delta_H$ (400 MHz, DMSO-d$_6$) 6.0 (1H, d, J 7.6, NH), 7.19 (2H, s, SO$_2$NH$_2$), 7.29 (2H, tt, J 7.2 1.6, 2×4'-H), 7.38 (9H, m, 1'-H, 4×3'-H, 4×4'-H) 7.56 (2H, d, J 8.8, 2×3'-H), 7.70 (2H, d, J 8.8, 2×2'-H), 8.9 (1H, s, NH); $\delta_C$ (100 MHz, DMSO-d$_6$) 154.9 (C=O urea), 144.2, 143.8, 137.2, 129.5, 127.9, 127.8, 127.7, 117.7, 57.8 (C-1').

4-{[(4'-Fluorophenyl)carbamoyl]amino}benzenesulfonamide (MST-104)

4-Aminobenzenesulfanilamide (0.50 g; 2.90 mmols) was treated with 4-fluorophenyl isocyanate (0.40 g; 2.90 mmols) and the reaction was stirred at r.t. for 2 days, treated as described in the general procedure previously reported to give MST-104 as a white solid in 55.5% yield. m.p. 242-243° C.; silica gel TLC $R_f$ 0.53 (ethyl acetate/petroleum ether 33%); $v_{max}$ (KBr) cm$^{-1}$, 3338 (N—H urea), 1697 (C=O urea), 1593 (aromatic); $\delta_H$ (400 MHz, DMSO-d$_6$) 7.17 (2H, t, J 9.0, 2×2'-H), 7.24 (2H, s, SO$_2$NH$_2$), 7.51 (2H, dd, J 9.0 4.8, 2×3'-H), 7.64 (2H, d, J 8.8, 2×3-H), 7.76 (2H, d, J 8.8, 2×2-H), 8.86 (1H, s, NH), 9.09 (1H, s, NH); $\delta_C$ (100 MHz, DMSO-d$_6$) 158.5 (d, $J_{C-F}$ 237, C-4'), 153.3 (C=O urea), 143.7, 137.8, 136.6 (d, $^4J_{C-F}$ 3, C-1'), 127.7, 121.2 (d, $^3J_{C-F}$ 7, C-2'), 118.4, 116.3 (d, $^2J_{C-F}$ 22, C-3'); $\delta_F$ (376.5 MHz, DMSO-d$_6$) −121.0 (1F, s).

4-({[(4'-Bromophenyl)amino]carbonyl}amino)benzenesulfonamide (MST-105)

4-Amino-benzenesulfanilamide (0.50 g; 2.90 mmols) was treated with 4-bromophenyl isocyanate (0.57 g; 2.90 mmols) and the reaction was stirred at r.t. for 1 day, treated as described in the general procedure previously reported to give MST-105 as a white solid in 43.1% yield. m.p. 269-271° C.; silica gel TLC $R_f$ 0.38 (ethyl acetate/petroleum ether 33%); $v_{max}$ (KBr) cm$^{-1}$, 3328 (N—H urea), 1652 (C=O urea), 1590 (aromatic); $\delta_H$ (400 MHz, DMSO-d$_6$) 7.24 (2H, s, SO$_2$NH$_2$), 7.49 (2H, d, J 9.2, 2×2'-H), 7.51 (2H, d, J 9.2, 2×3'-H), 7.64 (2H, d, J 8.8, 2×3-H), 7.76 (2H, d, J 8.8, 2×2-H), 8.99 (1H, s, NH), 9.15 (1H, s, NH); $\delta_C$ (100 MHz, DMSO-d$_6$) 152.6 (O=O urea), 143.1, 139.3, 137.5, 132.0, 127.3, 120.9, 118.1, 114.1.

4-{[(4'-Iodophenyl)carbamoyl]amino}benzenesulfonamide (MST-106)

4-Aminobenzenesulfanilamide (0.50 g; 2.90 mmols) was treated with 4-iodophenyl isocyanate (0.71 g; 2.90 mmols) and the reaction was stirred at r.t. overnight, treated as described in the general procedure previously reported to give MST-106 as a white solid in 46.5% yield. m.p. 275-277°; silica gel TLC $R_f$ 0.55 (ethyl acetate/petroleum ether 33%) $v_{max}$ (KBr) cm$^{-1}$, 3325 (N—H urea), 1652 (C=O urea), 1586 (aromatic); $\delta_H$ (400 MHz, DMSO-d$_6$) 7.24 (2H, s, SO$_2$NH$_2$), 7.36 (2H, d, J 8.8, 2×2'-H), 7.63 (2H, d, J 6.8, 2×3-H), 7.66 (2H, d, J 6.8, 2×2-H), 7.77 (2H, d, J 8.8, 2×3'-H), 8.97 (1H, s, NH), 9.15 (1H, s, NH); $\delta_C$ (100 MHz, DMSO-d$_6$), 153.2 (C=O urea), 143.7, 140.3, 138.5, 138.1, 127.9, 121.7, 118.6, 86.2 (C-4').

4-{[(Pentafluorophenyl)carbamoyl]amino}benzenesulfonamide (MST-107)

4-Aminobenzenesulfanilamide (0.50 g; 2.90 mmols) was treated with pentafluorophenyl isocyanate (0.60 g; 2.90 mmols) and the reaction was stirred r.t. for 1 day, treated as described in the general procedure previously reported to give MST-107 as a white solid in 97.7% yield. m.p. 251-253° C.; silica gel TLC $R_f$ 0.49 (ethyl acetate/petroleum ether 33%); $v_{max}$ (KBr) cm$^{-1}$, 3329 (N—H urea), 1656 (C=O urea), 1597 (aromatic); $\delta_H$ (400 MHz, DMSO-d$_6$)

7.23 (2H, s, SO$_2$NH$_2$), 7.61 (2H, d, J 8.8, 2×3-H), 7.74 (2H, d, J 8.8, 2×2-H), 8.65 (1H, s, NH), 9.48 (1H, s, NH); δ$_C$ (100 MHz, DMSO-d$_6$) 152.9 (C=O urea), 144.0 (m, J$_{C-F}$ 239, C-2'), 143.3, 139.6 (m, J$_{C-F}$ 248, C-4'), 138.5, 138.2 (m, J$_{C-F}$ 249, C-3'), 127.8, 118.8, 114.7 (ddd, $^2$J$_{C-F}$ 23, $^3$J$_{C-F}$ 14, $^4$J$_{C-F}$ 4, C-1'); O$_F$ (376.5 MHz, DMSO-d$_6$) −146.2 (2F, dd, $^3$J 24, $^4$J 5.1, 2×2'-F), −159.2 (2F, t, $^3$J 23, 2×4'-F), −164.0 (1F, dd, $^3$J 23.3, $^4$J 5.0, 2×3'-F).

4-{[(2'-Methoxyphenyl)amino]carbonyl)}aminobenzenesulfonamide (MST-108)

4-Amino-benzenesulfanilamide (0.50 g; 2.90 mmols) was treated with 2-methoxyphenyl isocyanate (0.43 g; 2.90 mmols) and the reaction was stirred at r.t. overnight, treated as described in the general procedure previously reported to give MST-108 as a white solid in 40.4% yield. m.p. 234-236° C.; silica gel TLC R$_f$ 0.47 (ethyl acetate/petroleum ether 33%); ν$_{max}$ (KBr) cm$^{-1}$, 3362 (N—H urea), 2838 (C—H aliphatic), 1684 (C=O urea), 1592 (aromatic); δ$_H$ (400 MHz, DMSO-d$_6$) 3.92 (3H, s, CH$_3$), 6.94 (1H, ddd, J 8.2 7.4 1.4, 4'-H), 7.01 (1H, ddd, J 8.0 7.4 1.6, 5'-H), 7.07 (1H, dd, J 8.2 1.2, 3'-H), 7.23 (2H, s, SO$_2$NH$_2$), 7.64 (2H, d, J 8.8, 2×2-H), 7.77 (2H, d, J 8.8, 2×3-H), 8.16 (1H, dd, J 8.0 1.6, 6'-H), 8.38 (1H, s, NH), 9.73 (1H, s, NH); δ$_C$ (100 MHz, DMSO-d$_6$) 153.0 (C=O, urea), 148.7, 143.8, 137.7, 129.2, 127.8, 123.2, 121.5, 119.4, 118.1, 111.7, 56.7 (CH$_3$).

4-{([(4'-Acetylphenyl)amino]carbonyl) amino}benzenesulfonamide (MST-109)

4-Aminobenzenesulfanilamide (0.50 g; 2.90 mmols) was treated with 4-acetylphenyl isocyanate (0.46 g; 2.90 mmols) and the reaction was stirred at r.t for 1 day, treated as described in the general procedure previously reported to give MST-109 as a white solid in 46.6% yield. m.p. 258-260° C.; silica gel TLC R$_f$ 0.27 (ethyl acetate/petroleum ether 33%); ν$_{max}$ (KBr) cm$^{-1}$, 3300 (N—H urea), 1659 (C=O urea), 1590 (aromatic); δ$_H$ (400 MHz, DMSO-d$_6$) 2.56 (3H, s, CH$_3$), 7.26 (2H, s, SO$_2$NH$_2$), 7.64 (2H, d, J 8.8, 2×2'-H), 7.67 (2H, d, J 8.8, 2×3-H), 7.79 (2H, d, J 8.8, 2×2-H), 7.96 (2H, d, J 8.8, 2×3'-H), 9.22 (1H, s, NH), 9.25 (1H, s, NH); δ$_C$ (100 MHz, DMSO-d$_6$) 197.3 (C=O), 152.9 (C=O urea), 144.9, 143.4, 138.2, 131.7, 130.6, 127.8, 118.7, 118.4, 27.3 (CH$_3$).

4-{([(2'-Isopropylphenyl)amino]carbonyl) amino}benzenesulfonamide(MST-110)

4-Aminobenzenesulfanilamide (0.50 g; 2.90 mmols) was treated with 2-isopropylphenyl isocyanate (0.47 g; 2.90 mmols) and the reaction was stirred at r.t. for 6 h, treated as described in the general procedure previously reported to give MST-110 as a white solid in 48.7% yield. m.p. 226-227° C.; silica gel TLC R$_f$ 0.65 (ethyl acetate/petroleum ether 33%); ν$_{max}$ (KBr) cm$^{-1}$, 3361 (N—H urea), 2966 (C—H aliphatic), 1676 (C=O urea), 1592 (aromatic); δ$_H$ (400 MHz, DMSO-d$_6$) 1.24 (6H, d, J 6.8, 2×CH$_3$), 3.19 (1H, sept, J 6.8, CH), 7.14 (1H, ddd, J 7.9 7.6 1.6, 4'-H), 7.19 (ddd, J 7.9 6.8 1.2, 5'-H), 7.23 (2H, s, SO$_2$NH$_2$), 7.34 (1H, dd, J 7.6 1.6, 3'-H), 7.65 (2H, d, J 8.8, 2×3-H), 7.68 (1H, dd, J 6.8 1.2, 6'-H), 7.76 (2H, d, J 8.8, 2×2-H), 8.11 (1H, s, NH), 9.37 (1H, s, NH); δ$_C$ (100 MHz, DMSO-d$_6$) 153.8 (C=O urea), 144.0, 140.8, 137.6, 136.0, 127.8, 126.7, 126.3, 125.3, 124.8, 118.2, 27.8 (CH), 24.1 (2×CH$_3$).

4-{([(4'-Isopropylphenyl)amino]carbonyl) amino}benzenesulfonamide(MST-111)

4-Amino-benzenesulfanilamide (0.50 g; 2.90 mmols) was treated with 4-isopropylphenyl isocyanate (0.47 g; 2.90 mmols) and the reaction was stirred at r.t. for 3 h, treated as described in the general procedure previously reported to give MST-111 as a white solid in 58.5% yield. m.p. 226-227° C.; silica gel TLC R$_f$ 0.50 (ethyl acetate/petroleum ether 33%); ν$_{max}$ (KBr) cm$^{-1}$, 3351 (N—H urea), 2964 (C—H aliphatic), 1647 (C=O urea), 1590 (aromatic); δ$_H$ (400 MHz, DMSO-d$_6$) 1.22 (6H, d, J 6.8, 2×CH$_3$), 2.87 (1H, sept, J 6.8, CH), 7.20 (2H, d, J 8.4, 2×3'-H), 7.23 (2H, s, SO$_2$NH$_2$), 7.40 (2H, d, J 8.4, 2×2'-H), 7.64 (2H, d, J 9.0, 2×3-H), 7.76 (2H, d, J 9.0, 2×2-H), 8.72 (1H, s, NH), 9.04 (1H, s, NH); δ$_C$ (100 MHz, DMSO-d$_6$) 153.2 (O=O urea), 143.9, 143.2, 137.9, 137.6, 127.7, 127.5, 119.5, 118.3, 33.7 (CH), 24.9 (CH$_3$).

4-({[(4'-Butylphenyl)amino]carbonyl}amino)benzenesulfonamide (MST-112)

4-Aminobenzenesulfanilamide (0.50 g; 2.90 mmols) was treated with 4-butylphenyl isocyanate (0.51 g; 2.90 mmols) and the reaction was stirred at r.t. for 3 h, treated as described in the general procedure previously reported to give MST-112 as a white solid in 48.6% yield. m.p. 243-245° C.; silica gel TLC R$_f$ 0.54 (ethyl acetate/petroleum ether 33%); ν$_{max}$ (KBr) cm$^{-1}$, 3333 (N—H urea), 2929 (C—H aliphatic), 1653 (C=O urea), 1592 (aromatic); δ$_H$ (400 MHz, DMSO-d$_6$) 0.93 (3H, t, J 7.2, CH$_3$), 1.33 (2H, six, J 7.4, CH$_2$), 1.57 (2H, sept, J 7.4, CH$_2$), 2.56 (2H, t, J 7.6, CH$_2$), 7.14 (2H, d, J 8.6, 2×3'-H), 7.23 (2H, s, SO$_2$NH$_2$), 7.39 (2H, d, J 8.6, 2×2'-H), 7.63 (2H, d, J 9.0, 2×3-H), 7.76 (2H, d, J 9.0, 2×2-H), 8.71 (1H, s, NH), 9.04 (1H, s, NH); δ$_C$ (100 MHz, DMSO-d$_6$) 153.2 (C=O urea), 143.9, 137.8, 137.6, 137.1, 129.5, 127.3, 119.5, 118.3, 35.1 (CH$_2$), 34.2 (CH$_2$), 22.6 (CH$_2$), 14.7 (CH$_3$).

4-{[(4'-Butoxyphenyl)carbamoyl] amino}benzenesulfonamide (MST-113)

4-Aminobenzenesulfanilamide (0.50 g; 2.90 mmols) was treated with 4-butoxyphenyl isocyanate (0.55 g; 2.90 mmols) and the reaction was stirred at r.t. for 1 day, treated as described in the general procedure previously reported to give MST-113 as a white solid in 46.0% yield. m.p. 236-239° C.; silica gel TLC R$_f$ 0.60 (ethyl acetate/petroleum ether 33%); ν$_{max}$ (KBr) cm$^{-1}$, 3361 (N—H urea), 2957 (C—H aliphatic), 1646 (C=O urea), 1592 (aromatic); δ$_H$ (400 MHz DMSO-d$_6$) 0.97 (3H, t, J 7.6, CH$_3$), 1.48 (2H, six, J 7.2, CH$_2$), 1.71 (2H, six, J 6.8, CH$_2$), 3.96 (2H, t, J 6.4, CH$_2$), 6.90 (2H, d, J 9.2, 2×3'-H), 7.22 (2H, s, SO$_2$NH$_2$), 7.38 (2H, d, J 9.2, 2×2'-H), 7.63 (2H, d, J 8.8, 2×3-H), 7.75 (2H, d, J 8.8, 2×2-H), 8.62 (1H, s, NH), 9.02 (1H, s, NH); δ$_C$ (100 MHz, DMSO-d$_6$) 155.1 (C=O urea), 153.3, 144.0, 137.5, 133.1, 127.7, 121.2, 118.2, 115.5, 68.2 (OCH$_2$), 31.7 (CH$_2$), 19.7 (CH$_2$), 14.6 (CH$_3$).

4-{([(4-Octylphenyl)amino]carbonyl) amino}benzenesulfonamide (MST-114)

4-Aminobenzenesulphanilamide (0.50 g; 2.90 mmols) was treated with 4-octylphenyl isocyanate (0.67 g; 2.90 mmols) and the reaction was stirred at r.t. for 1 day, treated as described in the general procedure previously reported to give MST-114 as a white solid in 41.4% yield. m.p. 282-

283° C.; silica gel TLC Rf 0.59 (ethyl acetate/petroleum ether 33%); $v_{max}$ (KBr) cm$^{-1}$, 3332 (N—H urea), 2924 (C—H aliphatic), 1653 (C=O urea), 1592 (aromatic); $\delta_H$ (400 MHz, DMSO-d$_6$) 0.89 (3H, t, J 6.8, CH$_3$), 1.30 (12H, m, CH$_2$), 1.57 (2H, t, J 7.6, CH$_2$), 7.14 (2H, d, J 8.6, 2×3'-H), 7.23 (2H, s, SO$_2$NH$_2$), 7.39 (2H, d, J 8.6, 2×2'-H), 7.63 (2H, d, J 9.0, 2×3-H), 7.76 (2H, d, J 9.0, 2×2-H), 8.72 (1H, s, NH), 9.05 (1H, s, NH); $\delta_C$ (100 MHz, DMSO-d$_6$), 153.2 (C=O urea), 143.9, 137.8, 137.6, 137.1, 129.5, 127.7, 119.5, 118.2, 35.4 (CH$_2$), 32.2 (CH$_2$), 32.0 (CH$_2$), 29.7 (CH$_2$), 29.6 (CH$_2$), 29.5 (CH$_2$), 23.0 (CH$_2$), 14.9 (CH$_3$).

4-{[(4'-Cyanophenyl)carbamoyl]amino}benzenesulfonamide (MST-115)

4-Aminobenzenesulfanilamide (0.50 g; 2.90 mmols) was treated 4-cyanophenyl isocyanate (0.42 g; 2.90 mmols) and the reaction was stirred at r.t. for 1 day, treated as described in the general procedure previously reported to give MST-115 as a white solid in 60.6% yield m.p. 265-267° C.; silica gel TLC R$_f$ 0.37 (ethyl acetate/petroleum ether 33%); $v_{max}$ (KBr) cm$^{-1}$, 3355 (N—H urea), 2221 (C≡N), 1695 (C=O urea), 1594 (aromatic); $\delta_H$ (400 MHz, DMSO-d$_6$) 7.26 (2H, s, SO$_2$NH$_2$), 7.66 (2H, d, J 8.8), 7.68 (2H, d, J 9.2), 7.78 (2H, d, J 8.8, overlapping), 7.79 (2H, d, J 8.8, overlapping), 9.28 (1H, s, NH), 9.35 (1H, s, NH); $\delta_C$ (100 MHz, DMSO-d$_6$) 152.8 (C=O urea), 144.8, 143.2, 138.3, 134.2, 127.8, 120.1, 119.2, 118.8, 104.6 (C≡N).

4-{([(2'-Cyanophenyl)amino]carbonyl)amino}benzenesulfonamide (MST-116)

4-Aminobenzenesulfanilamide (0.50 g; 2.90 mmols) was treated with 2-cyanophenyl isocyanate (0.41 g; 2.90 mmols) and the reaction was stirred for 1 day until a precipitate was formed. The crude obtained was purified by silica gel column chromatography eluting with ethyl acetate/petroleum ether 1/1 to give MST-116 as a white solid. m.p. 256-258° C.; silica gel TLC R$_f$ 0.73 (ethyl acetate/petroleum ether 33%); $v_{max}$ (KBr) cm$^{-1}$, 3310 (N—H urea), 2231 (C≡N), 1696 (C=O urea), 1587 (aromatic); $\delta_H$ (400 MHz, DMSO-d$_6$) 7.26 (1H, ddd, J 7.6 7.2 0.8, 4'-H), 7.27 (2H, s, SO$_2$NH$_2$), 7.67 (2H, d, J 9.0, 2×3-H), 7.70 (1H, ddd, J 8.4 7.2 1.6, 5'-H), 7.80 (2H, d, J 9.0, 2×2-H), 7.82 (1H, dd, 7.6 1.6, 3'-H), 8.1 (1H, dd, J 8.4 0.4, 6'-H), 8.90 (1H, s, NH), 9.78 (1H, s, NH); $\delta_C$ (100 MHz, DMSO-d$_6$) 152.8 (0=0 urea), 143.2, 142.4, 138.4, 135.0, 134.1, 127.8, 124.5, 122.6, 118.7, 117.8, 103.6 (C≡N).

4-({[(4'-Phenoxyphenyl)amino]carbonyl}amino)benzenesulfonamide (MST-117)

4-Aminobenzenesulfanilamide (0.50 g; 2.90 mmols) was treated with 4 phenoxyphenyl isocyanate (0.61 g; 2.90 mmols) and the reaction was stirred at r.t. for 5 h, treated as described in the general procedure previously reported to give MST-117 as a white solid in 46.8% yield. m.p. 236-237° C.; silica gel TLC R$_f$ 0.41 (ethyl acetate/petroleum ether 33%); $v_{max}$ (KBr) cm$^{-1}$, 3328 (N—H urea), 1653 (C=O urea), 1595 (aromatic); $\delta_H$ (400 MHz, DMSO-d$_6$) 7.00 (2H, dd, J 8.8 1.2, 3'-H), 7.03 (2H, d, J 9.0, 6'-H), 7.13 (1H, dt, J 7.5 0.8, 8'-H), 7.24 (2H, s, SO$_2$NH$_2$), 7.40 (2H, dd, J 9.0 7.5, 7'-H), 7.52 (2H, d, J 8.8, 2'-H), 7.65 (2H, d, J 9.2, 3-H), 7.76 (2H, d, J 9.2, 2-H), 8.84 (1H, s, NH), 9.08 (1H, s, NH); $\delta_C$ (100 MHz, DMSO-d$_6$) 158.5 (C=O urea), 153.3, 151.9, 143.8, 137.7, 136.2, 130.9, 127.7, 123.8, 121.2, 120.7, 118.7, 118.4.

4-[(Biphenyl-2'-ylcarbamoyl)amino]benzenesulfonamide (MST-118)

4-Aminobenzenesulfanilamide (0.50 g; 2.90 mmols) was treated with biphenyl-2-yl isocyanate (0.57 g; 2.90 mmols) and the reaction was stirred at r.t. for 1 day, treated as described in the general procedure previously reported to give MST-118 as a white solid in 40.0% yield. m.p. 229-231° C.; silica gel TLC R$_f$ 0.75 (ethyl acetate/petroleum ether 33%); $v_{max}$ (KBr) cm$^{-1}$, 3365 (N—H urea), 1675 (C=O urea), 1584 (aromatic); $\delta_H$ (400 MHz, DMSO-d$_6$) 7.20 (1H, d, J 7.4), 7.22 (2H, s, SO$_2$NH$_2$), 7.27 (1H, dd, J 7.4 1.6), 7.39 (1H, dt, J 8.4 1.6, 10'-H), 7.46 (2H, dt, J 6.8 1.6), 7.54 (1H, d, J 7.6, 6'-H), 7.58 (2H, d, J 9.2, 2×3-H), 7.74 (2H, d, J 9.2, 2×2-H), 7.83 (1H, s, NH), 7.95 (1H, d, J 8.0, 3'-H), 9.41 (1H, s, NH); $\delta_C$ (100 MHz, DMSO-d$_6$) 153.6 (C=O urea), 144.0, 139.5, 137.8, 136.4, 134.2, 131.5, 130.2, 129.9, 128.9, 128.6, 127.9, 124.8, 124.0, 118.3.

4-{[(3'-Nitrophenyl)carbamoyl]amino}benzenesulfonamide (MST-119)

4-Aminobenzenesulfanilamide (0.50 mg; 2.90 mmols) was treated with 3-nitrophenyl isocyanate (0.47 g; 2.90 mmols) and the reaction was stirred at r.t. for 1 day, treated as described in the general procedure previously reported to give MST-119 as a yellow solid in 44.3% yield. m.p. 246-248° C.; silica gel TLC R$_f$ 0.39 (ethyl acetate/petroleum ether 33%); $v_{max}$ (KBr) cm$^{-1}$, 3370 (N—H urea), 1709 (C=O urea), 1592 (aromatic); $\delta_H$ (400 MHz, DMSO-d$_6$) 7.23 (2H, s, SO$_2$NH$_2$), 7.59 (1H, dd, J 8.4 8.0, 5'-H), 7.65 (2H, d, J 9.0, 2×3-H), 7.73 (1H, ddd, J 8.4 2.0, 0.8, 6'-H), 7.76 (2H, d, J 9.0, 2×2-H), 7.86 (1H, ddd, J 8.0 2.4 0.8, 4'-H), 8.58 (1H, appt, J 2.2, 2'-H), 9.25 (1H, s, NH), 9.35 (1H, s, NH); $\delta_C$ (100 MHz, DMSO-d$_6$) 153.2 (0=0 urea), 149.1, 143.3, 141.6, 138.3, 131.1, 127.7, 125.5, 118.8, 117.6, 113.3.

4-{([(4'-Methoxy-2'-methylphenyl)amino]carbonyl)amino}benzenesulfonamide (MST-120)

4-Aminobenzenesulfanilamide (0.50 g; 2.90 mmols) was treated with 4-methoxy-2-methylphenyl isocyanate (0.47 g; 2.90 mmols) and the reaction was stirred at r.t. overnight, treated as described in the general procedure previously reported to give MST-120 as a white solid in 40.1% yield. m.p. 240-241° C.; silica gel TLC R$_f$ 0.35 (ethyl acetate/petroleum ether 33%); $v_{max}$ (KBr) cm$^{-1}$, 3313 (N—H urea), 2835 (C—H aliphatic), 1647 (C=O urea), 1591 (aromatic); $\delta_H$ (400 MHz, DMSO-d$_6$) 2.25 (3H, s, CH$_3$), 3.76 (3H, s, OCH$_3$), 6.78 (1H, dd, J 8.8 2.8, 5'-H), 6.84 (1H, d, J 2.8, 3'-H), 7.22 (2H, s, SO$_2$NH$_2$), 7.55 (1H, d, J 8.8, 6'-H), 7.63 (2H, d, J 8.8, 2×3-H), 7.75 (2H, d, J 8.8, 2×2-H), 7.96 (1H, s, NH), 9.26 (1H, s, NH); $\delta_C$ (100 MHz, DMSO-d$_6$) 156.6 (C=O urea), 153.7, 144.2, 137.4, 132.3, 130.7, 127.8, 125.3, 118.1, 116.4, 112.2, 56.1 (OCH$_3$), 19.0 (CH$_3$).

4-{[(9H-Fluoren-2-ylamino)carbonyl]amino}benzenesulfonamide (MST-121)

To a solution of 4-aminobenzenesulfanilamide (0.50 g; 2.90 mmols) in acetonitrile (20 ml) was added dropwise 9H-fluoren-2-yl isocyanate (0.59 g; 2.90 mmols) dissolved in 10 ml of acetonitrile. The reaction was stirred for 1 h at r.t., treated as described in the general procedure previously reported to give MST-121 as a white solid in 62.0% yield. m.p. 280-285° C.; silica gel TLC R$_f$ 0.52 (ethyl acetate/petroleum ether 33%); $v_{max}$ (KBr) cm$^{-1}$, 3329 (N—H urea), 1648 (C=O urea), 1591 (aromatic); $\delta_H$ (400 MHz, DMSO-$d_6$) 3.94 (2H, s, $CH_2$), 7.24 (2H, s, $SO_2NH_2$), 7.29 (1H, appt, J 7.2, 4'-H), 7.39 (1H, appt, J 7.2, 5'-H), 7.46 (1H, d, J 7.2, 3'-H), 7.58 (1H, d, J 7.2, 6'-H), 7.67 (1H, d, J 8.4, 2×3-H), 7.78 (1H, d, J 8.4, 2×2-H), 7.83 (3H, m, 2'-H, 7'-H, 8'-H), 8.94 (1H, s, NH), 9.14 (1H, s, NH); $\delta_C$ (100 MHz, DMSO-$d_6$) 153.2 (C=O urea), 144.9, 143.8, 143.5, 142.0, 139.3, 137.7, 136.4, 127.8, 127.6, 126.8, 125.9, 121.2, 120.2, 118.4, 118.2, 116.2, 37.4 ($CH_2$).

4-[(Cyclopentylcarbamoyl)amino]benzenesulfonamide (MST-122)

4-Aminobenzenesulfanilamide (0.50 g; 2.90 mmols) was treated with cyclopentyl isocyanate (0.32 g; 2.90 mmols) and the reaction was stirred at 50° C. for 2 h, treated as described in the general procedure previously reported to give MST-122 as a white solid in 68.8% yield. m.p. 224-226° C.; silica gel TLC $R_f$ 0.57 (ethyl acetate/petroleum ether 33%); $v_{max}$ (KBr) $cm^{-1}$, 3328 (N—H urea), 3055 (C—H aliphatic), 1684 (C=O urea), 1591 (aromatic); $\delta_H$ (400 MHz, DMSO-$d_6$) 1.41 (2H, m, 2×3'-$H_{ax}$), 1.58 (2H, m, 2×2'-$H_{ax}$), 1.67 (2H, m, 2×3'-$H_{eq}$), 1.88 (2H, m, 2×3'-$H_{eq}$), 3.98 (1H, six, J 6.8, 1'-H), 6.35 (1H, d, J 6.8, NH), 7.18 (2H, s, $SO_2NH_2$), 7.55 (2H, d, J 8.8, 2×3-H), 7.70 (2H, d, J 8.8, 2×2-H), 8.68 (1H, s, NH); $\delta_C$ (100 MHz, DMSO-$d_6$) 155.3 (C=O urea), 144.6, 136.8, 127.7, 117.6, 51.8 (C-1'), 33.7 (C-2'), 24.1 (C-3').

4-{([(3,5-dimethylphenyl)amino]carbonylamino)}benzenesulfonamide (MST-123)

4-Aminobenzenesulfanilamide (0.50 g; 2.90 mmols) was treated with 3,5-dimethylphenyl isocyanate (0.43 g; 2.90 mmols) and the reaction was stirred at r.t. overnight, treated as described in the general procedure previously reported to give MST-123 as a white solid in 60.6% yield. m.p 235-236° C.; silica gel TLC $R_f$ 0.58 (ethyl acetate/petroleum ether 33%); $v_{max}$ (KBr) $cm^{-1}$, 3343 (N—H urea), 2860 (C—H aliphatic), 1686 (C=O urea), 1595 (aromatic); $\delta_H$ (400 MHz, DMSO-$d_6$) 2.27 (6H, s, 2×$CH_3$), 6.68 (1H, s, 4'-H), 7.12 (2H, s, 2'-H), 7.23 (2H, s, $SO_2NH_2$), 7.64 (2H, d, J 8.8, 2×3-H), 7.76 (2H, d, J 8.8, 2×2-H), 8.67 (1H, s, NH), 9.06 (1H, s, NH); $\delta_C$ (100 MHz, DMSO-$d_6$) 153.1 (C=O, urea), 143.8, 140.1, 138.7, 137.7, 127.7, 124.7, 118.3, 117.1, 22.0 (2×$CH_3$).

4-{([(4'-chlorophenyl)amino]carbonylamino)}benzenesulfonamide (MST-124)

4-Aminobenzenesulfanilamide (0.50 g; 2.90 mmols) was treated with 4-chlorophenyl isocyanate (0.44 g; 2.90 mmols) and the reaction was stirred at r.t. overnight, treated as described in the general procedure previously reported to give MST-124 as a white solid in 89.4% yield. m.p 239-240° C.; silica gel TLC $R_f$ 0.44 (ethyl acetate/petroleum ether 33%); $v_{max}$ (KBr) $cm^{-1}$, 3327 (N—H urea), 1652 (C=O urea), 1592 (aromatic); $\delta_H$ (400 MHz, DMSO-$d_6$) 7.24 (2H, s, $SO_2NH_2$), 7.38 (2H, d, J 8.8, 2×2'-H), 7.53 (2H, d, J 8.8, 2×3'-H), 7.64 (2H, d, J 8.8, 2×3-H), 7.76 (2H, d, J 8.8, 2×2-H), 8.97 (1H, s, NH), 9.13 (1H, s, NH); $\delta_C$ (100 MHz, DMSO-$d_6$) 153.1 (C=O, urea), 143.6, 139.2, 137.9, 129.6, 127.7, 126.6, 120.9, 118.5.

4-{[(2,3-dihydro-1H-inden-5-ylamino]carbonylamino)}benzenesulfonamide (MST-125)

4-Aminobenzenesulfanilamide (0.50 g; 2.90 mmols) was treated with 5-indanylisocyanate (0.46 g; 2.90 mmols) and the reaction was stirred at r.t. overnight, treated as described in the general procedure previously reported to give MST-125 as a white solid in 60.6% yield. m.p 233-235° C.; silica gel TLC $R_f$ 0.61 (ethyl acetate/petroleum ether 33%); $v_{max}$ (KBr) $cm^{-1}$, 3333 (N—H urea), 2844 (C—H aliphatic), 1653 (C=O urea), 1592 (aromatic); $\delta_H$ (400 MHz, DMSO-$d_6$) 2.04 (2H, appqt, J 7.4, 2'-H), 2.85 (4H, appqt, J 7.4, 2×1'-H, 2×3'-H), 7.16 (1H, appd, J 8.2, 6'-H), 7.19 (1H, appdd, J 8.2 1.6, 7'-H), 7.25 (2H, s, $SO_2NH_2$), 7.42 (1H, s, 4'-H), 7.63 (2H, d, J 8.8, 2×3-H), 7.75 (2H, d, J 8.8, 2×2-H), 8.70 (1H, s, NH), 9.06 (1H, s, NH); $\delta_C$ (100 MHz, DMSO-$d_6$) 153.2 (C=O, urea), 145.2, 143.9, 138.4, 137.6, 127.8, 125.2, 118.3, 117.7, 115.7, one carbon overlapping signal, 33.48, 32.64, 26.15 (3×$CH_2$).

4-{[([4-(trifluoromethyl)phenyl]amino}carbonyl)amino]benzenesulfonamide (MST-126)

4-Aminobenzenesulfanilamide (0.50 g; 2.90 mmols) was treated with 4-trifluoromethyl-phenylisocyanate (0.54 g; 2.90 mmols) and the reaction was stirred at r.t. overnight, treated as described in the general procedure previously reported to give MST-126 as a white solid in 96.1% yield. m.p 281-283° C.; silica gel TLC $R_f$ 0.49 (ethyl acetate/petroleum ether 33%); $v_{max}$ (KBr) $cm^{-1}$, 3334 (N—H urea), 1657 (C=O urea), 1592 (aromatic); $\delta_H$ (400 MHz, DMSO-$d_6$) 7.27 (2H, s, $SO_2NH_2$), 7.66 (2H, d, J 8.8, 2×3-H), 7.72 (4H, m, 2×2'-H, 2×3'-H) 7.78 (2H, d, J 8.8, 2×2-H), 9.24 (1H, s, NH), 9.26 (1H, s, NH); $\delta_C$ (100 MHz, DMSO-$d_6$) 153.0 (C=O, urea), 144.0 (m, C-1'), 143.4 (C-4), 138.2 (C-1), 127.7 (2×C-2), 127.0 (q, $^3J_{C-F}$ 3.8, C-3'), 125.4 (q, $J_{C-F}$ 269, $CF_3$), 123.0 (q, $^2J_{C-F}$ 32, C-4'), 119.0 (2×C-2'), 118.7 (2×C-3); $\delta_F$ (376.5 MHz, DMSO-$d_6$) −60.1 (3F, s).

4-{[([3,5-bis(trifluoromethyl)phenyl]aminocarbonyl)amino]}benzenesulfonamide (MST-127)

4-Aminobenzenesulfanilamide (0.50 g; 2.90 mmols) was treated with 3,5-bis(trifluoromethyl)phenylisocyanate (0.74 g; 2.90 mmols) and the reaction was stirred at r.t. overnight, treated as described in the general procedure previously reported to give MST-127 as a white solid in 81.4% yield. m.p 228-229° C.; silica gel TLC $R_f$ 0.62 (ethyl acetate/petroleum ether 33%); $v_{max}$ (KBr) $cm^{-1}$, 3374 (N—H urea), 1653 (C=O urea), 1596 (aromatic); $\delta_H$ (400 MHz, DMSO-$d_6$) H), 7.27 (2H, s, $SO_2NH_2$), 7.69 (2H, d, J 9.0, 3-H), 7.71 (1H, s, 4'-H), 7.79 (2H, d, J 9.0, 2-H), 8.16 (2H, s, 2×2'-H), 9.43 (1H, s, NH), 9.54 (1H, s, NH); $\delta_C$ (100 MHz, DMSO-$d_6$) 153.2 (C=O, urea), 143.1, 142.5, 138.5, 131.7 (q, $^2J_{C-F}$ 32, 2×C-3'), 127.7 (2×C-2), 124.2 (q, $J_{C-F}$ 272, 2×$CF_3$), 119.2 (m, 2×C-2'), 119.1 (2×C-3), 115.7 (m, C-4'); $O_F$ (376.5 MHz, DMSO-$d_6$) −61.7 (6F, s).

Ureidosubstituted Compounds (MST-128-133)
Materials And Methods

Anhydrous solvents and all reagents were purchased from Sigma-Aldrich, Alfa Aesar and TCI. All reactions involving air- or moisture-sensitive compounds were performed under a nitrogen atmosphere using dried glassware and syringes techniques to transfer solutions. Infrared (IR) spectra were recorded as KBr plates and are expressed in $nhyd^{-1}$). Nuclear magnetic resonance ($^1$H-NMR, $^{13}$C-NMR, DEPT, HSQC, HMBC) spectra were recorded using a Bruker Advance III 400 MHz spectrometer in MeOH-d4 or in DMSO-$d_6$. The chemical shifts are reported in parts per million (ppm) and the coupling constants (J) are expressed in Hertz (Hz). Splitting patterns are designated as follows: s, singlet; d, doublet; sept, septet; t, triplet; q, quadruplet; m, multiplet; brs, broad singlet; dd, double of doubles, appt, aparent triplet, appq, aparent quartet. The assignment of exchangeable protons (OH and NH) was confirmed by the addition of $D_2O$. Analytical thin-layer chromatography (TLC) was carried out on Merck silica gel F-254 plates. Flash chromatography purifications were performed on Merck Silica gel 60 (230-400 mesh ASTM) as the stationary phase and ethylacetate/n-hexane or MeOH/DCM were used as eluents. Melting points (mp) were carried out in open capillary tubes and are uncorrected.

3-(3-(4'-Iodophenyl)ureido)benzenesulfonamide (MST-128)

3-(3-(4'-Iodophenyl)ureido)benzenesulfonamide (A): m.p. 256-258° C.; $v_{max}$ (KBr) cm$^{-1}$, 3165, 3265, 1643, 1589; $\delta_H$ (400 MHz, DMSO-d$_6$) 7.34-7.66 (9H, m, Ar—H, SO$_2$NH$_2$, exchange with D$_2$O), 8.10 (1H, d, J, 2.1, 2-H), 8.79 (1H, s, NH, exchange with D$_2$O), 9.08 (1H, s, NH, exchange with D$_2$O); $\delta_C$ (100 MHz, DMSO-d$_6$) 153.1 (C=O), 145.6, 140.9, 140.3, 138.3, 130.3, 122.1, 121.6, 119.9, 116.1, 85.9; Elem. Anal. Calc. [C, 37.42; H, 2.90; N, 10.07]. Found [C, 37.06; H, 2.79; N, 9.82]; m/z (ESI$^+$) 418 (M+Na)$^+$.

3-(3-(4'-Fluorophenyl)ureido)benzenesulfonamide (MST-129)

3-(3-(4'-Fluorophenyl)ureido)benzenesulfonamide (B): m.p. 233-235° C.; $v_{max}$ (KBr) cm$^{-1}$, 3377, 3352, 1685, 1557; $\delta_H$ (400 MHz, DMSO-d$_6$) 7.17 (1H, dd, J 8.8, Ar—H), 7.45 (2H, s, SO$_2$NH$_2$, exchange with D$_2$O), 7.47-7.60 (5H, m, Ar—H), 8.10 (1H, d, J, 2.1, 2-H), 8.78 (1H, s, NH, exchange with D$_2$O), 9.04 (1H, s, NH, exchange with D$_2$O); $\delta_C$ (100 MHz, DMSO-d$_6$) 158.4 (d, J$_{C-F}$ 237, C-4'), 153.4 (C=O), 145.6, 141.1, 136.6, 130.3, 122.0, 121.2, 119.8, 116.3, 116.1; O$_F$ (376 MHz, DMSO-d$_6$) −121.14; Elem. Anal. Calc. [C, 50.48; H, 3.91; N, 13.58]. Found [C, 49.98; H, 3.79; N, 13.49]; m/z (ESI$^+$) 311 (M+Na)$^+$.

3-(3-(3'-Nitrophenyl)ureido)benzenesulfonamide (MST-130)

3-(3-(3'-Nitrophenyl)ureido)benzenesulfonamide (C): m.p. 252-255° C.; $v_{max}$ (KBr) cm$^{-1}$, 3380, 3350, 1689, 1550; $\delta_H$ (400 MHz, DMSO-d$_6$) 7.41 (2H, s, SO$_2$NH$_2$, exchange with D$_2$O), 7.48-7.64 (4H, m, Ar—H), 7.77 (1H, dd, J 7.2, 2.1, Ar—H), 7.87 (1H, dd, J 7.2, 2.1, Ar—H), 8.14 (1H, d, J, 2.1, 2-H), 8.63 (1H, d, J, 2.1, 2'-H), 9.23 (1H, s, NH, exchange with D$_2$O), 9.31 (1H, s, NH, exchange with D$_2$O); $\delta_C$ (100 MHz, DMSO-d$_6$) 153.3 (C=O), 149.1, 145.7, 141.7, 140.6, 131.0, 130.3, 125.4, 122.4, 120.2, 117.4, 116.4, 113.2; Elem. Anal. Calc. [C, 46.43; H, 3.60; N, 16.66]. Found [C, 46.91; H, 3.55; N, 16.94]; m/z (ESI$^+$) 337 (M+Na)$^+$.

3-(3-(4'-Acetylphenyl)ureido)benzenesulfonamide (MST-131)

3-(3-(4'-Acetylphenyl)ureido)benzenesulfonamide (D): m.p. 267-269° C.; $v_{max}$ (KBr) cm$^{-1}$, 3402, 3351, 2014, 1933, 1912, 1593; $\delta_H$ (400 MHz, DMSO-d$_6$) 2.56 (3H, s, CH$_3$), 7.41 (2H, s, SO$_2$NH$_2$, exchange with D$_2$O), 7.48-7.55 (3H, m, 4-H, 5-H, 6-H), 7.60 (2H, d, J 7.2, 2×2'-H), 7.97 (2H, d, J 7.2, 2×3'-H), 8.13 (1H, t, J 2.0, 2-H), 9.18 (1H, s, NH, exchange with D$_2$O), 9.19 (1H, s, NH, exchange with D$_2$O); $\delta_C$ (100 MHz, DMSO-d$_6$) 197.2 (CH$_3$C=O), 153.0 (C=O), 145.7, 145.0, 140.7, 131.6, 130.5, 130.4, 122.2, 120.2, 118.2, 116.2, 27.2; Elem. Anal. Calc. [C, 54.04; H, 4.54; N, 12.60]. Found [C, 54.31; H, 4.47; N, 12.96]; m/z (ESI$^+$) 334 (M+Na)$^+$.

3-(3-(2'-Isopropylphenyl)ureido)benzenesulfonamide (MST-132)

3-(3-(2'-Isopropylphenyl)ureido)benzenesulfonamide (E): m.p. 175-176° C.; $v_{max}$ (KBr) cm$^{-1}$, 3328, 3300, 1690, 1556; $\delta_H$ (400 MHz, DMSO-d$_6$) 1.23 (6H, d, J 6.2, 2×8'-H$_3$), 3.19 (1H, sept, J 6.2, 7'-H), 7.14 (2H, m, Ar—H), 7.35 (1H, d, J 7.2, Ar—H), 7.37 (2H, s, SO$_2$NH$_2$, exchange with D$_2$O), 7.59-7.70 (4H, m, Ar—H), 8.00 (1H, s, NH, exchange with D$_2$O), 8.10 (1H, t, J 2.0, 2-H), 9.30 (1H, s, NH, exchange with D$_2$O); $\delta_C$ (100 MHz, DMSO-d$_6$) 153.9 (C=O), 145.6, 141.3, 140.7, 136.1, 130.3, 126.7, 126.2, 125.2, 124.7, 121.7, 119.5, 115.8, 27.8, 24.0; Elem. Anal. Calc. [C, 57.64; H, 5.74; N, 12.60]. Found [C, 58.14; H, 5.73; N, 12.70]; m/z (ESI$^+$) 334 (M+Na)$^+$.

3-(3-(Perfluorophenyl)ureido)benzenesulfonamide (MST-133)

3-(3-(Perfluorophenyl)ureido)benzenesulfonamide (F): m.p. 224-227° C.; $V_{max}$ (KBr) cm$^{-1}$, 3390, 3287, 1785, 1560; $\delta_H$ (400 MHz, DMSO-d$_6$) 7.38 (2H, s, SO$_2$NH$_2$, exchange with D$_2$O), 7.50 (2H, m, Ar—H), 7.63 (1H, d, J 7.2, Ar—H), 8.09 (1H, s, 2-H), 8.63 (1H, s, ArNHCONH, exchange with D$_2$O), 9.47 ((1H, s, ArNHCONH, exchange with D$_2$O); $\delta_C$ (100 MHz, DMSO-d$_6$) 152.9 (C=O), 145.6, 144.1 (d, J$^1_{C-F}$ 245), 140.7, 139.6 (d, J$^1_{C-F}$ 253), 138.2 (d, J$^1_{C-F}$ 245), 130.4, 122.3, 120.4, 116.4, 114.7 (t, J$_{C-F}$ 12); O$_F$ (376 MHz, DMSO-d$_6$) −146.3 (2F, dd, J 19.2 4.8, 2×2'-F), −159.2 (1F, t, J 22.9, 4'-F), −164.0 (2F, dt, J 22.6 4.8, 2×3'-F); Elem. Anal. Calc. [C, 40.95; H, 2.11; N, 11.02]. Found [C, 40.68; H, 1.74; N, 11.00]; m/z (ESI$^+$) 382 (M+Na)$^+$.

TABLE 2

CA INHIBITION DATA WITH META-UREIDOSUBSTITUTED SULFONAMIDES MST-128 TO-133.

| Compound | Ki (nM) | | | |
| --- | --- | --- | --- | --- |
| | hCA I | hCA II | hCA IX | hCA XII |
| MST-128 | 426 | 67 | 13.1 | 4.5 |
| MST-129 | 414 | 59 | 10.2 | 5.8 |
| MST-130 | 614 | 41 | 7.9 | 8.2 |
| MST-131 | 762 | 74 | 15.1 | 12.8 |
| MST-132 | 593 | 38 | 18.5 | 13.7 |
| MST-133 | 69 | 5.4 | 4.2 | 4.8 |

Synthesis of Ureidosulfonamides Corresponding to MST-134-148

4-(3-(4'-chloro-2-fluorophenyl)ureido)benzenesulfonamide MST-134

4-(3-(4'-Chloro-2-fluorophenyl)ureido)benzenesulfonamide: $v_{max}$ (KBr) cm$^{-1}$, 3166, 3270, 1640, 1592; $\delta_H$ (400 MHz, DMSO-d$_6$) 7.26-7.30 (3H, brs, SO$_2$NH$_2$, exchange with D$_2$O, 5'/6'-H), 7.52 (1H, dd, J, 8.2, 2.1, 5'/6'-H), 7.64 (2H, d, J 8.2, 2×2'/3'-H), 7.78 (2H, d, J 8.2, 2×2'/3'-H), 8.19 (1H, dd, J 9.0, 8.2 3'-H), 8.79 (1H, s, NH, exchange with D$_2$O), 9.47 (1H, s, NH, exchange with D$_2$O); $\delta_C$ (100 MHz, DMSO-d$_6$) 152.8 (d, J$^1_{C-F}$ 245, C-2'), 152.7 (C=O), 143.2, 138.2, 127.8, 127.4, (d, J$_{C-F}$ 10), 126.7 (d, J$_{C-F}$ 10), 125.6, 122.5, 118.4, 116.6 (d, J$_{C-F}$ 23); δ$_F$ (376 MHz, DMSO-d$_6$) –126.38.

4-(3-(4'-bromo-2'-fluorophenyl)ureido)benzenesulfonamide MST-135

4-(3-(4'-Bromo-2'-fluorophenyl)ureido)benzenesulfonamide: v$_{max}$ (KBr) cm$^{-1}$, 3166, 3270, 1640, 1592; δ$_H$ (400 MHz, DMSO-d$_6$) 7.27 (2H, s, SO$_2$NH$_2$, exchange with D$_2$O), 7.40 (1H, d, J, 9.2 5'/6'-H), 7.64 (3H, m, 2×2/3-H, 5'/6'-H), 7.78 (2H, d, J 9.2, 2×2/3-H), 8.16 (1H, t, J 8.8 3'-H), 8.79 (1H, s, NH, exchange with D$_2$O), 9.48 (1H, s, NH, exchange with D$_2$O); δ$_C$ (100 MHz, DMSO-d$_6$) 152.8 (d, J$^1_{C-F}$ 245, C-2'), 152.7 (C=O), 143.2, 138.2, 128.5, 127.9, 127.7 (d, J$_{C-F}$ 6), 122.8, 119.2 (d, J$_{C-F}$ 22), 118.4, 114.0 (d, J$_{C-F}$ 9); O$_F$ (376 MHz, DMSO-d$_6$) –126.38.

4-(3-(2'-fluoro-5-nitrophenyl)ureido)benzenesulfonamide MST-136

4-(3-(2'-Fluoro-5'-nitrophenyl)ureido)benzenesulfonamide: v$_{max}$ (KBr) cm$^{-1}$, 3166, 3270, 1640, 1592; δ$_H$ (400 MHz, DMSO-d$_6$) 7.28 (2H, s, SO$_2$NH$_2$, exchange with D$_2$O), 7.60 (1H, dd, J, 9.2 6.8, 6'-H), 7.70 (2H, d, J 9.2, 2×2/3-H), 7.80 (2H, d, J 9.2, 2×2/3-H), 7.96 (1H, m, 4'-H), 9.13 (1H, s, NH, exchange with D$_2$O), 9.18 (1H, m, 6'-H), 9.57 (1H, s, NH, exchange with D$_2$O); δ$_C$ (100 MHz, DMSO-d$_6$) 156.0 (d, J$^1_{C-F}$ 251, C-2'), 154.8 (C=O), 144.9, 142.9, 138.6, 129.3 (d, J$_{C-F}$ 12), 127.9, 119.0 (d, J$_{C-F}$ 9), 118.7, 117.0 (d, J$_{C-F}$ 22), 115.7; δ$_F$ (376 MHz, DMSO-d$_6$) –119.43

4-(3-(2',4',5'-trifluorophenyl)ureido)benzenesulfonamide MST-137

4-(3-(2',4',5'-Trifluorophenyl)ureido)benzenesulfonamide: v$_{max}$ (KBr) cm$^{-1}$, 3166, 3270, 1640, 1592; δ$_H$ (400 MHz, DMSO-d$_6$) 7.27 (2H, s, SO$_2$NH$_2$, exchange with D$_2$O), 7.68 (3H, m, 2×2/3-H, 3'-H), 7.78 (2H, d, J 9.2, 2×2/3-H), 8.22 (1H, m, 6'-H), 8.58 (1H, s, NH, exchange with D$_2$O), 9.47 (1H, s, NH, exchange with D$_2$O); δ$_C$ (100 MHz, DMSO-d$_6$) 152.7 (C=O), 148.2 (dd, J$^1_{C-F}$ 240, 12.2), 146.4 (d, J$^1_{C-F}$ 237, 15.8), 144.4 (dd, J$^1_{C-F}$ 250, 12.0), 143.3, 138.3, 127.8, 125.0 (m), 118.5, 109.5 (dd, J$_{C-F}$ 24.5, 2.9), 106.4 (dd, J$_{C-F}$ 25.6, 22.0); δ$_F$ (376 MHz, DMSO-d$_6$) –130.64 (d, J$_{F-F}$ 13.9), –141.75 (m), –143.06 (d, J$_{F-F}$ 24.4).

4-(3-(2'-fluoro-5'-(trifluoromethyl)phenyl)ureido) benzenesulfonamide MST-138

4-(3-(2'-Fluoro-5'-(trifluoromethyl)phenyl)ureido)benzenesulfonamide: v$_{max}$ (KBr) cm$^{-1}$, 3166, 3270, 1640, 1592; δ$_H$ (400 MHz, DMSO-d$_6$) 7.28 (2H, s, SO$_2$NH$_2$, exchange with D$_2$O), 7.47 (1H, m, 4'-H), 7.55 (1H, dd, J 10.8 8.8, 3'-H), 7.67 (2H, d, J 8.8, 2×2/3-H), 7.79 (2H, d, J 8.8, 2×2/3-H), 8.63 (1H, m, 6'-H), 9.03 (1H, s, NH, exchange with D$_2$O), 9.56 (1H, s, NH, exchange with D$_2$O); δ$_C$ (100 MHz, DMSO-d$_6$) 154.0 (d, J$^1_{C-F}$ 247, C-2'), 152.8 (C=O), 143.0, 138.5, 129.30 (d, J$_{C-F}$ 11.3), 127.9, 126.2 (dd, J$_{C-F}$ 31.8, 3.3), 123.5, 120.7 (m), 118.6, 117.7, 117.0 (d, J$_{C-F}$ 20.5); O$_F$ (376 MHz, DMSO-d$_6$) –60.7 (3F, C—F$_3$), –123.8 (1F, 2'-F).

4-(3-(2'-fluoro-3'-(trifluoromethyl)phenyl)ureido) benzenesulfonamide MST-139

4-(3-(2'-fluoro-3'-(trifluoromethyl)phenyl)ureido)benzenesulfonamide: v$_{max}$ (KBr) cm$^{-1}$, 3166, 3270, 1640, 1592; δ$_H$ (400 MHz, DMSO-d$_6$) 7.27 (2H, s, SO$_2$NH$_2$, exchange with D$_2$O), 7.43 (2H, m, 5'-H, 6'-H), 7.65 (2H, d, J 8.8, 2×2/3-H), 7.79 (2H, d, J 8.8, 2×2/3-H), 8.46 (1H, m, 4'-H), 8.96 (1H, s, NH, exchange with D$_2$O), 9.53 (1H, s, NH, exchange with D$_2$O); δ$_C$ (100 MHz, DMSO-d$_6$) 152.7 (C=O), 150.0 ((d, J$^1_{C-F}$ 250, C-2'), 143.1, 138.3, 129.4 ((d, J$_{C-F}$ 9), 127.8, 125.9 (d, J$_{C-F}$ 43.9), 124.9, 122.2, 120.4, 118.7, 117.5 (dd, J$_{C-F}$ 32.1, 3.2); O$_F$ (376 MHz, DMSO-d$_6$) –59.8 (3F, d, J$_{F-F}$ 13.2, C—F$_3$), –132.2 (1F, q, J 13.2, 2'-F).

4-(3-(2',3',4'-trifluorophenyl)ureido)benzenesulfonamide MST-140

4-(3-(2',3',4'-Trifluorophenyl)ureido)benzenesulfonamide: v$_{max}$ (KBr) cm$^{-1}$, 3166, 3270, 1640, 1592; δ$_H$ (400 MHz, DMSO-d$_6$) 7.27 (2H, s, SO$_2$NH$_2$, exchange with D$_2$O), 7.34 (2H, m, 5'/6'-H), 7.65 (2H, d, J 8.8, 2×2/3-H), 7.77 (2H, d, J 8.8, 2×2/3-H), 7.88 (1H, m, 5'/6'-H), 8.82 (1H, s, NH, exchange with D$_2$O), 9.45 (1H, s, NH, exchange with D$_2$O); δ$_C$ (100 MHz, DMSO-d$_6$) 152.9 (C=O), 146.6 (d, J$^1_{C-F}$ 237), 143.2, 141.8 (d, J$^1_{C-F}$ 240), 139.6 (d, J$^1_{C-F}$ 242), 138.3, 127.8, 126.0 (m), 118.5, 116.7 (m), 112.6 (dd, J$_{C-F}$ 18, 4); δ$_F$ (376 MHz, DMSO-d$_6$) –143.1 (1F, d, J$_{F-F}$ 21.7, 2'/4'-F), –148.4 (1F, d, J$_{F-F}$ 21.7, 2'/4'-F), –161.1 (1F, t, J$_{F-F}$ 21.7, 3'-F).

4-(3-(2'-fluorophenyl)ureido)benzenesulfonamide MST-141

4-(3-(2'-Fluorophenyl)ureido)benzenesulfonamide: v$_{max}$ (KBr) cm$^{-1}$, 3166, 3270, 1640, 1592; δ$_H$ (400 MHz, DMSO-d$_6$) 7.07 (1H, m, 3'-H), 7.20 (1H, m, 4'-H), 7.26 (3H, brs, SO$_2$NH$_2$, exchange with D$_2$O, 5'-H), 7.64 (2H, d, J 8.8, 2×2/3-H), 7.80 (2H, d, J 8.8, 2×2/3-H), 8.20 (1H, m, 6'-H) 8.70 (1H, s, NH, exchange with D$_2$O), 9.46 (1H, s, NH, exchange with D$_2$O); δ$_C$ (100 MHz, DMSO-d$_6$) 153.1 (d, J$^1_{C-F}$ 240), 152.9 (C=O), 143.4, 138.1, 128.1, 127.8, 125.4, 123.8, 121.7, 118.3, 116.6 (d, J$_{C-F}$ 19); δ$_F$ (376 MHz, DMSO-d$_6$) –129.59.

4-(3-(2',4'-difluorophenyl)ureido)benzenesulfonamide MST-142

4-(3-(2',4'-Difluorophenyl)ureido)benzenesulfonamide: v$_{max}$ (KBr) cm$^{-1}$, 3166, 3270, 1640, 1592; δ$_H$ (400 MHz, DMSO-d$_6$) 7.08 (1H, m, 3'/5'-H), 7.25 (2H, s, SO$_2$NH$_2$, exchange with D$_2$O), 7.36 (1H, m, 3'/5'-H), 7.64 (2H, d, J 8.8, 2×2/3-H), 7.78 (2H, d, J 8.8, 2×2/3-H), 8.11 (1H, m, 6'-H), 8.64 (1H, s, NH, exchange with D$_2$O), 9.41 (1H, s, NH, exchange with D$_2$O); δ$_C$ (100 MHz, DMSO-d$_6$) 158.1 (dd, J$_{C-F}$ 243, 13), 153.4 (dd, J$_{C-F}$ 244, 12), 153.0 (C=O), 143.4, 138.1, 128.1, 127.8, 124.5 (d, J$_{C-F}$ 9), 123.2 (d, J$_{C-F}$ 8), 118.4, 112.0 (d, J$_{C-F}$ 21), 104.8 (t, J$_{C-F}$ 25); O$_F$ (376 MHz, DMSO-d$_6$) –117.52, –124.3.

4-(3-(3'-chlorophenyl)ureido)benzenesulfonamide MST-143

4-(3-(3'-chlorophenyl)ureido)benzenesulfonamide: v$_{max}$ (KBr) cm$^{-1}$, 3166, 3270, 1640, 1592; δ$_H$ (400 MHz, DMSO-d$_6$) 7.07 (1H, d, J 8.8, 4'-H), 7.25 (2H, s, SO$_2$NH$_2$, exchange with D$_2$O), 7.33 (2H, m, 5'-H, 6'-H), 7.64 (2H, d, J 8.8, 2×2/3-H), 7.77 (3H, m, J 8.8, 2×2/3-H, 2'-H), 9.04 (1H, s, NH, exchange with D$_2$O), 9.17 (1H, s, NH, exchange with D$_2$O); $\delta_C$ (100 MHz, DMSO-d$_6$) 153.1 (C=O), 143.5, 141.8, 138.0, 134.1, 131.3, 127.7, 122.7, 118.7, 118.6, 117.8.

4-(3-(2',5'-dichlorophenyl)ureido)benzenesulfonamide MST-144

4-(3-(2',5'-Dichlorophenyl)ureido)benzenesulfonamide: $v_{max}$ (KBr) cm$^{-1}$, 3166, 3270, 1640, 1592; $\delta_H$ (400 MHz, DMSO-d$_6$) 7.15 (1H, dd, J 8.8 2.8, 4'-H), 7.28 (2H, s, SO$_2$NH$_2$, exchange with D$_2$O), 7.55 (1H, dd, J 8.8 2.8, 3'-H), 7.64 (2H, d, J 8.8, 2×2/3-H), 7.79 (2H, d, J 8.8, 2×2/3-H), 8.35 (1H, d, J 2.8, 6'-H), 8.60 (1H, s, NH, exchange with D$_2$O), 9.90 (1H, s, NH, exchange with D$_2$O); $\delta_C$ (100 MHz, DMSO-d$_6$) 152.7 (C=O), 143.1, 138.4, 137.8, 132.9, 131.5, 127.9, 124.0, 121.3, 121.1, 118.7.

4-(3-(2'-Chloro-5-nitrophenyl)ureido)benzenesulfonamide MST-145

4-(3-(2'-Chloro-5'-nitrophenyl)ureido)benzenesulfonamide: $v_{max}$ (KBr) cm$^{-1}$, 3164, 3271, 1641, 1592; $\delta_H$ (400 MHz, DMSO-d$_6$) 7.29 (2H, s, SO$_2$NH$_2$, exchange with D$_2$O), 7.70 (2H, d, J 8.8, 2×2/3-H), 7.82 (3H, m, 2×2/3-H, 3'-H), 7.93 (1H, dd, J 8.9 2.2, 4'-H), 8.84 (1H, s, NH, exchange with D$_2$O), 9.20 (1H, d, J 2.2, 6'-H), 9.99 (1H, s, NH, exchange with D$_2$O); $\delta_C$ (100 MHz, DMSO-d$_6$) 152.7 (C=O), 147.5. 142.9, 138.6, 137.7, 131.3, 128.9, 127.9, 118.8, 118.5, 115.6.

4-(3-(2'-Chloro-4'-(trifluoromethyl)phenyl)ureido)benzenesulfonamide MST-146

4-(3-(2'-Chloro-4'-(trifluoromethyl)phenyl)ureido)benzenesulfonamide: $v_{max}$ (KBr) cm$^{-1}$, 3169, 1639, 1560; $\delta_H$ (400 MHz, DMSO-d$_6$) 7.29 (2H, s, SO$_2$NH$_2$, exchange with D$_2$O), 7.69 (2H, d, J 8.8, 2×2/3-H), 7.74 (1H, dd, J 8.8 4.0, 5'-H), 7.80 (2H, d, J 8.8, 2×2/3-H), 7.92 (1H, dd, J 4.0, 3'-H), 8.50 (1H, d, J 8.8, 6'-H), 8.76 (1H, s, NH, exchange with D$_2$O), 10.0 (1H, s, NH, exchange with D$_2$O); $\delta_C$ (100 MHz, DMSO-d$_6$) 152.5, 143.0, 140.4, 138.5, 128.7, 127.9, 127.2 (m), 125.8 (m), 124.0 (d, J$_{C-F}$ 33.0), 13.2, 122.7, 121.4; $\delta_F$ (376 MHz, DMSO-d$_6$) −60.42.

4-(3-(2',6'-difluorophenyl)ureido)benzenesulfonamide MST-147

4-(3-(2',6'-Difluorophenyl)ureido)benzenesulfonamide: $v_{max}$ (KBr) cm$^{-1}$, 3164, 3270, 1641, 1590; $\delta_H$ (400 MHz, DMSO-d$_6$) 7.33 (4H, m, SO$_2$NH$_2$, exchange with D$_2$O, 2×5'-H), 7.37 (1H, m, 4'-H), 7.64 (2H, d, J 8.8, 2×2/3-H), 7.76 (2H, d, J 8.8, 2×2/3-H), 8.30 (1H, s, NH, exchange with D$_2$O), 9.38 (1H, s, NH, exchange with D$_2$O); $\delta_C$ (100 MHz, DMSO-d$_6$) 158 (d, J$^1_{C-F}$ 247, C-2', C-6'), 153.27 (C=O), 143.7, 138.0, 128.3 (m), 127.7, 118.5, 115.9 (t, J$_{C-F}$ 16, C-4'), 112.6 (d, J$_{C-F}$ 23, 2×C-3'); $\delta_F$ (376 MHz, DMSO-d$_6$) −118.73.

4-(3-(perchlorophenyl)ureido)benzenesulfonamide MST-148

4-(3-(perchlorophenyl)ureido)benzenesulfonamide: $v_{max}$ (KBr) cm$^{-1}$, 3168, 3275, 1641, 1590; $\delta_H$ (400 MHz, DMSO-d$_6$) 7.24 (2H, m, SO$_2$NH$_2$, exchange with D$_2$O), 7.64 (2H, d, J 8.8, 2×2/3-H), 7.75 (2H, d, J 8.8, 2×2/3-H), 8.29 (1H, s, NH, exchange with D$_2$O), 9.38 (1H, s, NH, exchange with D$_2$O); $\delta_C$ (100 MHz, DMSO-d$_6$) 153.2 (C=O), 142.0, 139.2, 130.1 (overlapping signals), 127.4, 125.5.

TABLE 3

CA INHIBITION DATA WITH UREIDOSUBSTITUTED SULFONAMIDES MST-134-148

| Compound | Ki (nM) | | | |
|---|---|---|---|---|
| | hCA I | hCA II | hCA IX | hCA XII |
| MST-134 | 436 | 162 | 5.1 | 7.9 |
| MST-135 | 373 | 418 | 6.3 | 7.4 |
| MST-136 | 519 | 276 | 7.3 | 7.6 |
| MST-137 | 569 | 215 | 7.6 | 6.2 |
| MST-138 | 363 | 170 | 7.4 | 10.1 |
| MST-139 | 395 | 196 | 8.7 | 8.5 |
| MST-140 | 484 | 335 | 9.6 | 6.4 |
| MST-141 | 550 | 33.0 | 7.7 | 7.3 |
| MST-142 | 275 | 60.6 | 3.7 | 7.1 |
| MST-143 | 158 | 10.0 | 8.4 | 8.5 |
| MST-144 | 747 | 58.2 | 8.9 | 6.8 |
| MST-145 | 307 | 0.94 | 8.2 | 6.1 |
| MST-146 | 192 | 0.97 | 8.4 | 8.2 |
| MST-149 | 158 | 0.93 | 6.1 | 8.3 |
| MST-150 | 538 | 362 | 6.3 | 7.6 |

For the remaining examples, the following methods and additional information will be a useful reference.

Cell Culture and Hypoxic Exposure

The acquisition, generation and culture of the luciferase expressing mouse breast cancer cell lines 4T1, 66cl4 and 67NR, and the human breast cancer cell lines MDA-231 and MDA-231 LM2-4 have been described previously (Lou et al, (2008) Dev Dyn 237:2755-2768; Lou et al, (2011) Cancer Res, 71:3364-3376. For culture in hypoxia, cells were maintained in 1% O2 and 5% CO2 balanced with N2 at 37° C. in a humidified incubator in a sealed anaerobic workstation.

Generation of Stable Cells shRNAmir vectors targeting mouse CAIX and a non-silencing sequence (Open Biosystems) were transfected into 90% confluent cells using LipofectAMINEPLUS™ (Invitrogen Life Technologies) according to the manufacturer's instructions. Due to the previous utilization of puromycin, transfected cells were selected using hygromycin. Stable shCAIX clones were derived by limited dilution cloning. For (re-)introduction of CAIX into cells, human CAIX (gift from Dr. Jacques Pouyssegur, University of Nice) was transfected into 4T1 cells following the same procedure and Zeocin was used for selection.

Measurement of Extracellular pH

Changes in solution pH were assessed using procedures published previously (29, 42, 43). In brief, cells were plated at appropriate density (1×104 cells/cm2 for 4T1 cells and its transfected derivatives, 2×104 cells/cm2 for 66cl4 cells, 1×104 cells/cm2 for 67NR cells and its transfected derivatives) in 60 mm dishes and allowed to recover overnight. A standard volume of 3 ml of fresh media/dish was then added and cells were incubated in normoxia (air+5% CO2) or hypoxia (1% O$_2$ and 5% CO2 balanced with nitrogen) for 72 h. Care was taken to ensure that cultures grown in normoxia and hypoxia were at similar confluence and contained similar cell numbers at the time of medium collection. Collected spent media was maintained at 37° C. and pH was measured immediately using a digital pH meter. Cell counts were performed to ensure that cell numbers for a given cell line were comparable in both environmental conditions. Cells were harvested on ice for qRT-PCR and Western blot analysis.

Pharmacological Inhibitors

The chemical properties of the sulfonamide, MST-017, have been described previously under the name CAI 17 (Supuran, C. 2008, Nature. Vol 7: 168-181). Ureido sulfonamides are new. For in vitro studies, the compounds were dissolved in DMSO, stored at −80° C. and diluted into culture medium just prior to application. Subconfluent cells were incubated with MST-017 for 72 hours in normoxia or hypoxia, washed 3× in PBS and imaged using a Zeiss Axioplan™ epifluorescence microscope. For in vivo studies, the MST-017 inhibitor was administered by i.p. injection (first two doses were administered i.v.) at 75 mg/kg and 150 mg/kg 3× per week for 2 weeks. Dosing concentrations and schedules for the other inhibitors are indicated in the appropriate examples below. The compounds were solubilized in PEG400/ethanol/saline prior to injection. Vehicle components were held constant as inhibitor concentrations were varied.

Analysis of mRNA and Protein Expression

Quantitative Real-Time PCR (qRT-PCR) was conducted in 384-well plates on an Applied Biosystems instrument using a Roche Universal Probe Library (UPL) according to the manufacturer's instructions. Briefly, 1 μg of total RNA from either subconfluent cells or snap frozen tissue was used to make cDNA. 10 μl of qRT-PCR mixture containing 100 nM UPL probe, 200 nM of each primer (Invitrogen) and TaqMan™ PCR master mix (Applied Biosystems) was loaded into each well for 40 cycles of PCR (44). Relative gene expression quantification data were acquired and analyzed using an ABI Prism 7900HT Sequence Detection System and the standard 2-ΔΔct method using β-actin as the housekeeping gene. For immunoblotting, cells or flash frozen tumor tissue were lysed in 1% Triton X-100 buffer (50 mM Hepes, pH=7.5, 150 mM NaCl, 10% glycerol, 1 mM EGTA and 2 mM EDTA), supplemented with the appropriate inhibitors. Equal amounts of protein were loaded on SDA-PAGE gels. To enhance the detection of HIF-1α before degradation, cells at equal densities were directly lysed in 4×SDS loading buffer in hypoxia. Western blots were performed using mouse CAIX (1:500), HIF-1α (1:250), human CAIX (1:1000) (all from R&D Systems) and β-actin (1:10,000, Sigma) antibodies.

Mouse Tumor Models

All animal studies and procedures were done in accordance with protocols approved by the Institution Animal Care Committee at the BC Cancer Research Centre and the University of British Columbia (Vancouver, BC, Canada).

Syngeneic Orthotopic Tumors and Spontaneous Metastasis

4T1 cells ($1 \times 10^6$) or 67NR cells ($2 \times 10^6$) were orthotopically implanted into the fourth mammary fat pad of 7-9 week-old female BALB/c mice as described previously (Lou et al, (2011) Cancer Res 71:3364-3376; Lou et al, (2008) Dev Dyn 237:2755-2768). Injection of cell numbers of this magnitude is standard for propagation of these tumors, and is well below that used in other models of tumor growth (Erler, J T. Bennewith, K L, Icolau, M. Nature 440: 1222-1226). Primary tumor growth rates were calculated from caliper measurements using the modified ellipsoid formula $(L \times W^2)/2$. Tumor formation and metastasis progression was monitored and quantified using bioluminescent imaging as previously described (Ebos et al., (2009) Cancer Cell 15:232-239; Lou et al., (2008) Dev Dyn 237:2755-2768).

Experimental Metastasis Assays

For studies involving genetic depletion of CAIX, 4T1 or 67NR cells ($5 \times 10^5$) were injected directly into the tail vein of 7-9 week-old female BALB/c mice. Mice were imaged once per week to follow the growth of metastases. Mice were euthanized 20 days post-injection and lungs were resected for further analysis. Tumor burden in the lung was quantified by manually counting nodules visible on the lung surface. For studies using sulphonamide inhibitors, 4T1 cells ($1-5 \times 10^5$) were injected as described above (Pacchiano et al, (2011) J Med Chem 54:1896-1902).

Human Xenograft Tumors

For studies involving CAIX depletion, $1 \times 10^7$ MDA-MB-231 cells suspended in a 50% Matrigel/PBS solution were implanted subcutaneously in 6-8 week-old female NOD.CB17-prkdc$^{scid}$/J mice. For primary breast tumor xenografts using the MDA-MB-231 LM2-4$^{Luc+}$ variant (Ebos et al, (2009) Cancer Cell 15:232-239), $2 \times 10^6$ cells were implanted orthotopically in mice as described above. Therapy was initiated when the tumors reached 200 mm$^3$. For both models, tumor growth was monitored by caliper measurement.

3D Matrigel Invasion Assay

A 3D "on-top" matrigel culture assay was performed as described previously (Lee et al, (2007) Nat Methods 4:359-365). Briefly, MDA-231 LM2-4 Luc+ cells ($1.5 \times 10^4$ cells/cm$^2$) were resuspended in 100 μl/well growth media containing 2× the final concentration of inhibitor and plated into 8-well chamber slides precoated with matrigel. Cells were allowed to attach for 45 minutes with side-to-side agitation every 10-15 minutes to prevent clumping of cells in the center of the well. An additional 100 μl/well media containing 10% matrigel was added to the cells and cultures were incubated in hypoxia for 4 days. Images were acquired and cultures were fixed for TUNEL using the "whole culture fixation" methodology outlined in Lee et al, (2007) Nat Methods 4:359-365).

Tumorsphere Culture

4T1 cells were grown as monolayers with twice weekly sub-cultivation in DMEM (Gibco) containing 5% fetal bovine serum (FBS) (Sigma). Subsequently, shNS and shCAIX 4T1 were cultured as tumorspheres in mammocult media (StemCell Technologies, Vancouver, B.C., Canada) as per the manufacturer's instructions.

(Tumorspheres are 3-dimensional structures (often spherical in shape) composed of adherent cancer cells that form when tumor cells are cultured in vitro under specific growth conditions (Fillmore and Kuperwasser, (2008) Breast Cancer Res. 10: R25). Tumorspheres generally grow in suspension culture and are considered the in vitro surrogate to in vivo tumors.)

Flow Cytometric Analyses

4T1 tumorspheres were incubated with trypsin, washed once in HF buffer (HBSS containing 2% Fetal Bovine Serum), then stained with anti-CD24-APC and anti-CD44-PECy7 using 0.3 μl of antibody per 106 cells in 100 ul HF, and incubated on ice for 10 min. Following incubation, cells were washed once with HF buffer and resuspended in 300 ul HF buffer containing 4',6-diamidino-2-phenylindole (DAPI; final concentration, 1 μg/ml). Cells were separated on an Aria cell sorter (BD Biosciences, San Jose, Calif., USA). Live cells were gated on the basis of forward and side scatter, and single cells were gated on the basis of forward scatter and pulse width. Gates were determined by analysis of unstained cells, isotype specific controls, and single stains. The CD44+CD24−/low or CD44+CD24+ cells were not assessed for purity due to the low numbers of cells obtained. The cell counter of the flow cytometers was used to determine cell numbers. Cells were collected into DMEM media or HF buffer.

Immunohistochemistry

Two hours before tumor excision mice were injected i.p. with a saline solution containing 1500 mg/kg BrdUrd (Sigma) and 60 mg/kg Pimonidazole (Chemicon), and i.v. 5 min before with DiOC7(3) (70 µl, 0.6 mg/ml; Molecular Probes). Serial tumor cryosections (10 µm) were cut with a Cryostar™ HM560 (Microm International), air dried for 24 h, and imaged for DiOC7(3) tissue fluorescence to visualize blood flow. Sections were fixed in 50% (v/v) acetone/methanol for 10 min at room temperature. The staining was performed using anti-PECAM/CD31 antibody (1:2000 clone, 2H8, BD Pharmingen) and Alexa 647 anti-hamster secondary (1:200, Invitrogen) for vasculature, polyclonal rabbit-anti-pimonidazole (1:2000, Hydroxyprobe Inc.) and Alexa 488 anti-rabbit secondary (1:200, Molecular Probes) for hypoxia, TUNEL (Roche Diagnostics) with a TMR red tagged dUTP for apoptosis. After fluorescence imaging slides were transferred to distilled water for 10 min followed by 1 h treatment with 2 M HCl and 5 min neutralization with 0.1 M sodium borate. DNA incorporated BrdUrd was detected using monoclonal rat anti-BrdUrd (1:500, clone BU1/75, Sigma) and anti-mouse peroxidase conjugate antibody (1:200, Sigma) and a metal enhanced DAB substrate (1:10, Pierce). haematoxylin counterstained slides were dehydrated and mounted using Permount (Fisher Scientific) before imaging. Image acquisition and analysis was done as previously described (Kyle, A H., Huxham, L A., Yeoman, D M., et al 2007. Clin Cancer Res 13:2804-2810). Paraffin embedded tumor sections were also stained for CAIX (1:100 for primary tumors, 1:50 for lung metastases, Santa Cruz Biotechnology) and HIF-1α (1:100, R&D Systems) as previously described (Luo et al.). 26 For the lymphangiogenesis studies, frozen tissue sections were fixed with 2% PFA for 20 min, and stained with rabbit anti-LYVE-1 (1:100, R&D Systems) and rat anti-CD31 (1:100, BD Pharmigen) dissolved in PBS containing 10% bovine serum albumin and 2% goat serum for 1 h at room temperature in a humidified container. Alexa 488 anti-rabbit and Alexa 546 anti-rat antibodies were used as secondary antibodies for 1 h followed by Vectashield mounting medium (Vector Laboratories) containing DAPI nuclear counter stain for mounting.

Cell Proliferation Assay

Cell growth was measured using an MTT cell proliferation kit (Roche Applied Science) according to the manufacturer's instructions. In brief, cells were plated in 96-well plates at a density of 5×103 cells/cm2 and allowed to recover overnight. Parallel samples were then incubated in normoxia and hypoxia for 48 to 72 h prior to performing the assay.

Apoptosis Assay

TUNEL labeling (Roche Applied Science) was employed for analysis of apoptosis mostly according to the manufacturer's instructions. Briefly, subconfluent cells grown on coverslips were incubated for 48 h under normoxia or hypoxia in 1% serum, air-dried, fixed in 4% paraformaldehyde for 60 min and permeabilized for 10 min in PBS and 0.1% Triton-X-100 at room temperature. Cell layers were then incubated with the TUNEL reagents for 60 min at 37° C., washed in PBS and counterstained with a 1:10,000 dilution of H33342.

Historical Clinical Analysis

A tissue microarray of 4,444 patients with a new diagnosis of invasive breast cancer in the province of British Columbia from 1986 to 1992 was created from tumor specimens submitted to a central estrogen receptor laboratory. The methods used to create the TMAs have been described (Cheang, M D., Chia, S K., Vodu, D et al. 2009. J Natl Cancer Inst 101:736-750). The TMA cohort representing were approximately 70% of all breast cancer cases diagnosed during this time were all referred to the British Columbia Cancer Agency. 3,630 cases had adequate tumor and staining results for assessment of all biomarkers. Immunohistochemistry for ER, PR, HER2, CK 5/6, EGFR and Ki67 was performed concurrently on serial sections and scored as described previously (Cheang M D et al.). CAIX expression was assessed using a murine monoclonal antibody (M75; 1:50) (Choi, S W., Kim, J Y., Park, J Y. 2008 Hum Pathol 39:1317-1322). Scoring of CAIX expression was either 0: no staining or 1: any staining and performed independently and blindly by 2 pathologists. Prior approval of the study was obtained from the Ethics Committee of the University of British Columbia.

Statistical Analysis

Results were subjected to statistical analysis using the Data Analysis ToolPack™ in Excel software. Two-tailed p values were calculated using student's t-test. Data were considered significant for $p<0.05$. Statistical analysis for the clinical outcomes was performed using SPSS 13.0 (Chicago, Ill.), S-Plus 6.2 (Seattle, Wash.) and R 2.1.1 (http://www.r-project.org). In univariate analysis, BCSS (date of diagnosis of primary breast cancer to date of death with breast cancer as the primary or underlying cause) and RFS (date of diagnosis of primary breast cancer to the date of a local, regional or distant recurrence) and distant RFS (date of diagnosis of primary breast cancer to the date of a distant recurrence) were estimated by Kaplan-Meier curves. Log-rank test was used to estimate the survival differences. For multivariate analysis, a Cox proportional hazards model was used to estimate the adjusted hazard ratios and significance. To assess the violations of proportional hazard models, smoothed plots of weighted Schoenfeld residuals were used.

Example 2

CAIX is a Prognostic Marker in a Large Cohort of Breast Cancer Patients

Although previous studies have reported that CAIX expression in several types of cancer, including breast cancer, correlates with poor patient prognosis as previously described, the sample sizes have been relatively small and adjuvant treatments not uniform. To validate CAIX as an important prognostic marker in a large sample population subjected to standardized treatment, we analyzed the expression of CAIX in a primary breast tumor tissue microarray (TMA) containing 3992 patient samples with a median follow-up of 10.5 years.

The methods used to create the TMAs have been described (Cheang, M D., Chia, S K., Vodu, D et al. 2009. J Natl Cancer Inst 101:736-750). The TMA cohort representing were approximately 70% of all breast cancer cases diagnosed during this time were all referred to the British Columbia Cancer Agency. CAIX expression was assessed using a murine monoclonal antibody (M75; 1:50) (Choi, S W., Kim, J Y, Park, J Y. 2008 Hum Pathol 39:1317-1322). Scoring of CAIX expression was either 0: no staining or 1: any staining and performed independently and blindly by two pathologists. Prior approval of the study was obtained from the Ethics Committee of the University of British Columbia.

Statistical Analysis

Results were subjected to statistical analysis using the Data Analysis ToolPack™ in Excel software. Two-tailed p values were calculated using student's t-test. Data were considered significant for $p<0.05$. Statistical analysis for the clinical outcomes was performed using SPSS 13.0 (Chicago, Ill.), S-Plus 6.2 (Seattle, Wash.) and R 2.1.1 (http://www.r-project.org). In univariate analysis, BCSS (date of diagnosis of primary breast cancer to date of death with breast cancer as the primary or underlying cause) and RFS (date of diagnosis of primary breast cancer to the date of a local, regional or distant recurrence) and distant RFS (date of diagnosis of primary breast cancer to the date of a distant recurrence) were estimated by Kaplan-Meier curves. Log-rank test was used to estimate the survival differences. For multivariate analysis, a Cox proportional hazards model was used to estimate the adjusted hazard ratios and significance. To assess the violations of proportional hazard models, smoothed plots of weighted Schoenfeld residuals were used.

CAIX expression was seen in 15.6% of assessable tumors and CAIX was differentially expressed among the biological subtypes, with the highest correlation in the basal breast cancers (51%) and the lowest proportion in the luminal A subtype (8%) (Table 5 below).

In Kaplan-Meier analyses, CAIX expression was significantly associated with worse relapse free survival (FIG. 1A), distant relapse free survival (FIG. 1B) and breast cancer specific survival (FIG. 1C), achieving very high levels of statistical significance ($p<10-17$, $p<10-16$, and $p<10-13$, respectively). The 10 year distant relapse free survival and breast cancer specific survival rates in the CAIX positive versus CAIX negative groups were 57% compared to 73%, and 62% compared to 78%, respectively. In multivariate analyses, including all standard prognostic variables and biological subtypes, CAIX expression remained a strong independent poor prognostic factor with a hazard ratio of 1.4. These data confirm and extend the results of previous studies that have shown that CAIX is a prognostic marker in a large number of breast cancer patients.

This example provides evidence that the compounds disclosed herein will be therapeutic for any cancers susceptible to metastases, or those overexpressing CAIX, a target shown in a large patient databank to be associated with decreased survival in patients.

TABLE 4

CAIX EXPRESSION ACCORDING TO BIOLOGICAL SUBTYPE

| Breast Cancer Subtype | Total N | N CAIX +ve | % CAIX +ve |
|---|---|---|---|
| LumA (ER or PR +, HER2−, ki67 −) | 1437 | 120 | 8% |
| LumB (ER or PR +, Her2−, ki67 +) | 815 | 88 | 11% |
| Lum/HER2+ (Her2 +, ER or PR +) | 213 | 36 | 17% |
| Her2+ (Her2+, ER−, PR−) | 239 | 80 | 33% |
| Basal (ER−, PR−, Her2−, CK56 or EGFR +) | 327 | 168 | 51% |

Above, LumA is luminal A; LumB is luminal B; ER is estrogen receptor; PR is progesterone receptor; EGFR is epithelial growth factor receptor; and "+ve" is positive.

Example 3

Metastatic 4T1 Tumors are Characterized by Hypdxia and CAIX Expression

Figure 2:
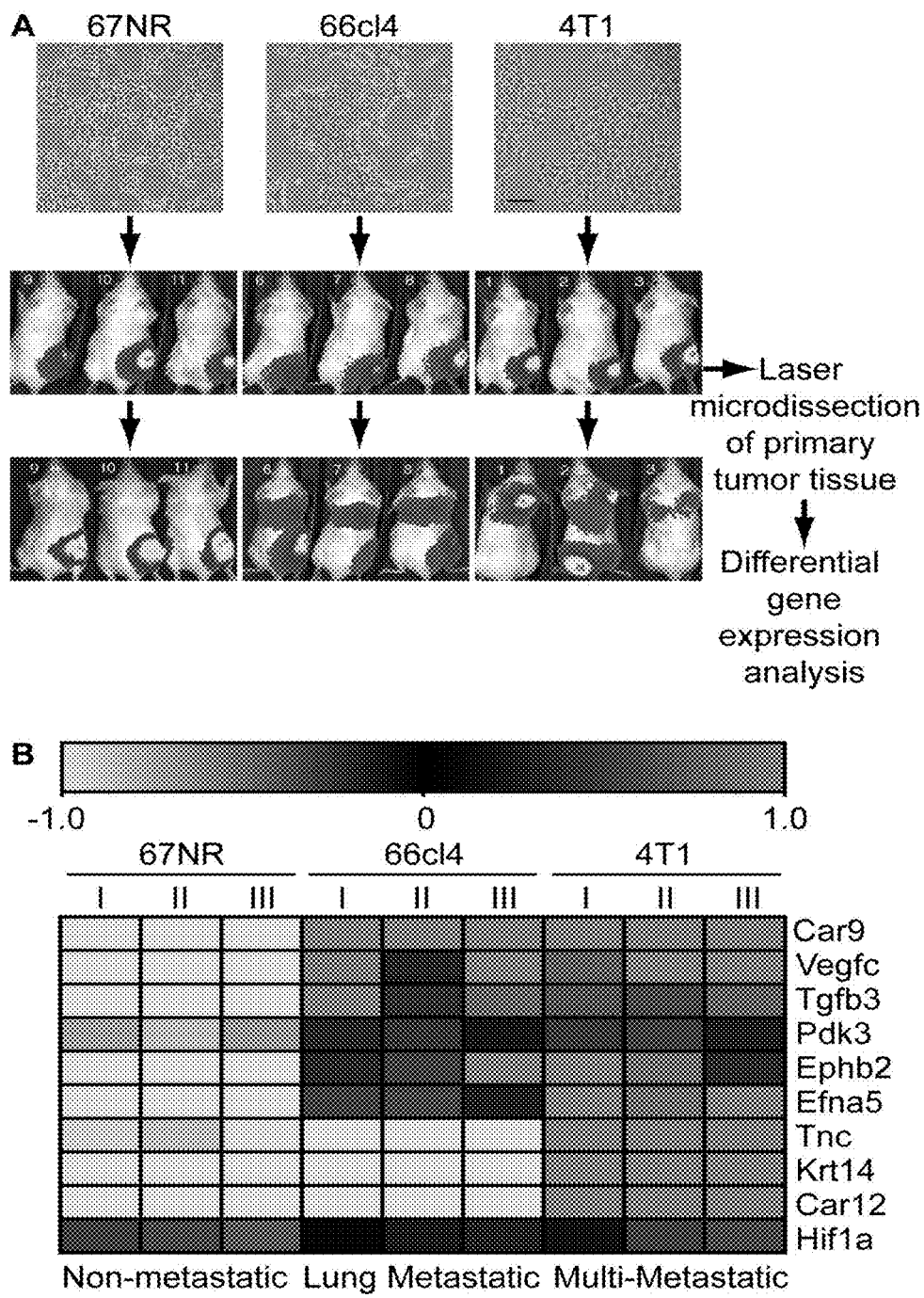
FIG. 2 shows (A) cell cultures for three cell lines 67NR, 66cl4 and 4T1 together with mouse models demonstrating bioluminescent labeling of the tumor cells in vivo and (B) hypoxia-induced gene expression table for the three tumor types (high expression, dark; low expression, light).

FIG. 2 shows cell cultures, mouse models with bioluminescent labeling, and a hypoxia-induced gene expression table for three tumor cell lines. Briefly, metastatic (4T1, 66cl4) and non-metastatic (67NR) mouse mammary tumor cell lines stably expressing luciferase were inoculated into the mammary fat pad of mice. Tumor formation and metastatic progression were monitored by bioluminescent imaging. Primary tumor cells were isolated by laser microdissection and differential gene expression analysis was performed on isolated tumor cells. (B) Tumor tissue from three mice from each cell model was analyzed for expression of hypoxia-induced genes (high expression, dark; low expression, light).

Figure 3:
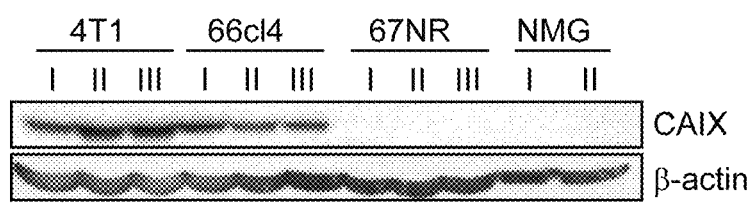
FIG. 3 shows a Western blot showing CAIX over-expression in the primary tumors. NMG=normal mammary gland. Beta-actin served as a loading control.

Non-metastatic 67NR tumors exhibited high vascular density, were largely devoid of hypoxia, and had low numbers of apoptotic cells. In contrast, primary tumors derived from the metastatic cell lines, especially the 4T1 cell line, were poorly vascularized, and had large areas of hypoxia and necrosis with high numbers of apoptotic cells (FIG. 2). Among the hypoxia-inducible genes identified in these tumors, the expression of CAIX, in particular, was elevated in both metastatic variants (FIGS. 2 and 2). We observed robust levels of CAIX protein localized to the plasma membrane in the metastatic tumors, whereas CAIX expression was absent from the non-metastatic 67NR tumors. A Western blot showing CAIX overexpression in the primary tumors is reproduced in FIG. 3. NMG=normal mammary gland. Beta-actin served as a loading control.

These data indicate that hypoxia-induced CAIX expression may be critical for increasing the metastatic potential of primary breast tumors.

Example 4

Validation of the 4T1 Model with Respect to CAIX Expression, pH Regulation and Cell Survival in Hypdxia For these experiments, 4T1 cells were cultured for 48 h in normoxia or hypoxia and the levels of CAIX expression were analyzed using qRT-PCR and Western blots with beta-actin acting as a control. Data are expressed as mean±s.e.m. n=3, $P<0.005$, *$P<10^{-3}$. In a second step, 4T1 cells expressing non-silencing shRNA (shNS) or shRNA targeting CAIX (shCAIX) were incubated for 72 h. Two independent clones (C2, C5) expressing shCAIX were analyzed. Data are expressed as means±s.e.m. n=3. ***$P<0.0005$, compared to cells cultured in normoxia. CAIX gene expression in the 4T1 cells was silenced by stably expressing constructs targeting mouse CAIX and cultured the cells in hypoxia to determine the efficacy of the shRNA to inhibit hypoxia-induced expression of CAIX.

Figure 4:
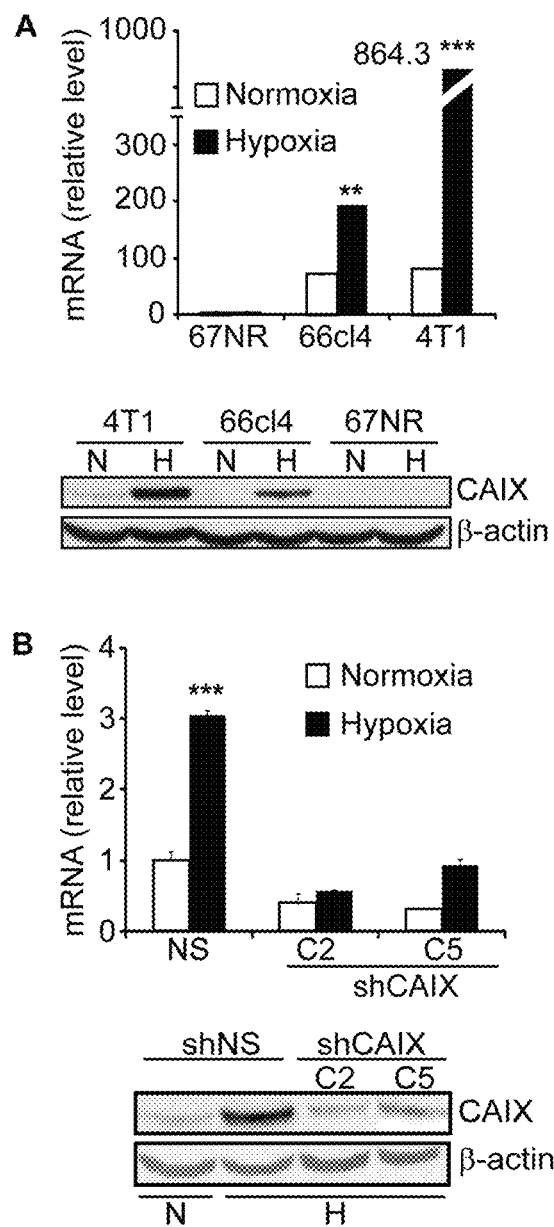
FIG. 4 shows (A) graph of the data relating to CAIX expression in metastatic (4T1, 66cl4) and non-metastatic (67NR) cells incubated for 72 h as measured by qRT-PCR (graph) and Western blot of lysates (gel). Data are expressed as mean±s.e.m. n=3, $P<0.005$, *$P<10^{-3}$. Beta-actin is shown as a loading control. (B) 4T1 cells expressing non-silencing shRNA (shNS) or shRNA targeting CAIX (shCAIX) incubated for 72 h. Two independent clones (C2, C5) expressing shCAIX were analyzed. Bottom panel, lysates were assessed by Western blot for CAIX expression. Beta-actin served as a loading control.

Thus, metastatic cell lines, especially the 4T1 cell line, induced CAIX expression in response to hypoxia (FIG. 4A). In contrast, culture in hypoxia did not induce CAIX expression in the non-metastatic cell line 67NR. 4T1 Cells expressing a non-silencing control shRNA (shNS) dramatically upregulated the expression of CAIX in hypoxia (FIG. 4B), whereas hypoxia-induced CAIX expression was markedly attenuated in two independent clones (C2, C5) expressing shRNA targeting CAIX (shCAIX; FIG. 4B).

CAIX is functionally linked to the control of tumor pH through its regulation of the intracellular and extracellular pH. Hypoxia-induced extracellular acidosis is a measure of the biological activity of CAIX. Acidification of the extracellular medium in hypoxia is blocked in the shCAIX-expressing 4T1 clones relative to the parental and shNS expressing 4T1 cells, suggesting that silencing CAIX gene expression induces functional inhibition of pH regulation in the metastatic 4T1 cells.

Figure 5:
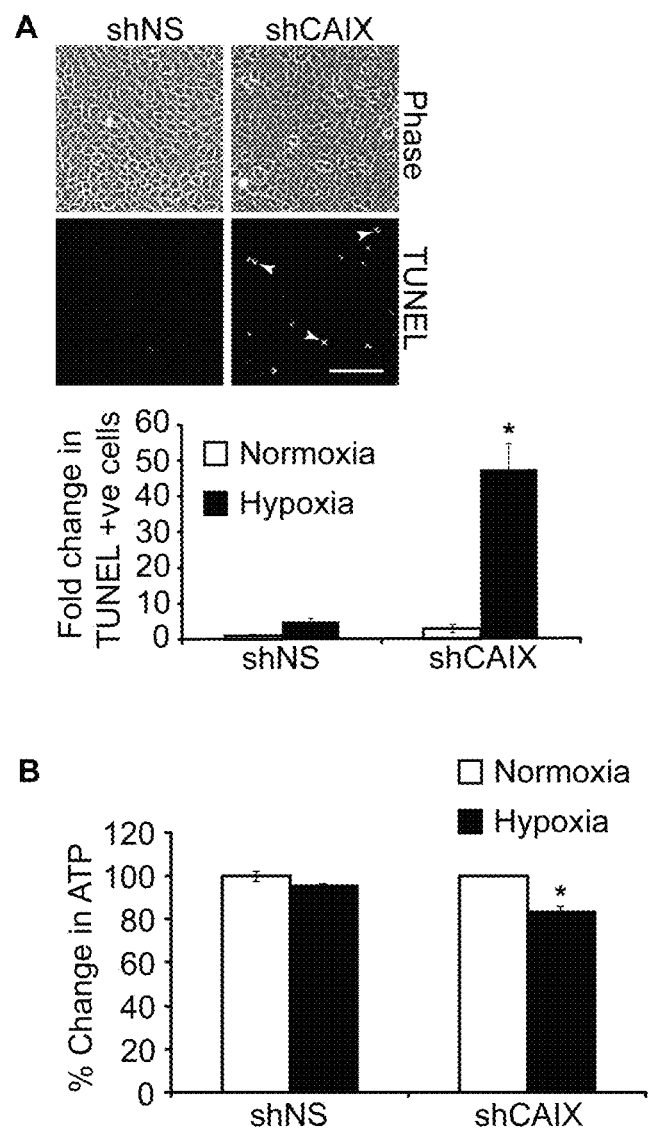
FIG. 5 includes representative images of TUNEL-positive cells (arrows) of (A) TOP 4T1 cells expressing shCAIX and cultured for 48 h in hypoxia and the amount of cell death was compared to 4T1 cells expressing shNS. Top panel, representative images of TUNEL-positive cells (arrows). Scale bar=100 um. (A) Bottom panel, graph showing quantification of the TUNEL-positive cells by counting 5 random fields/cell line at 20× magnification. Data are expressed as fold change in TUNEL-positive cells, compared to control cells cultured in normoxia. n=5. (B) 4T1 cells expressing shNS or shCAIX were cultured in the indicated conditions for 72 hrs and intracellular levels of ATP were determined on total cell lysates. *P<0.01, compared to levels of ATP in normoxia.

4T1 cells depleted of CAIX showed increased cell death compared to non-silencing control cells when cultured in hypoxia (FIG. 5). This suggests that CAIX is important for the survival of metastatic breast cancer cells in hypoxic environments.

Example 5

In Vivo Demonstration

Figure 6:
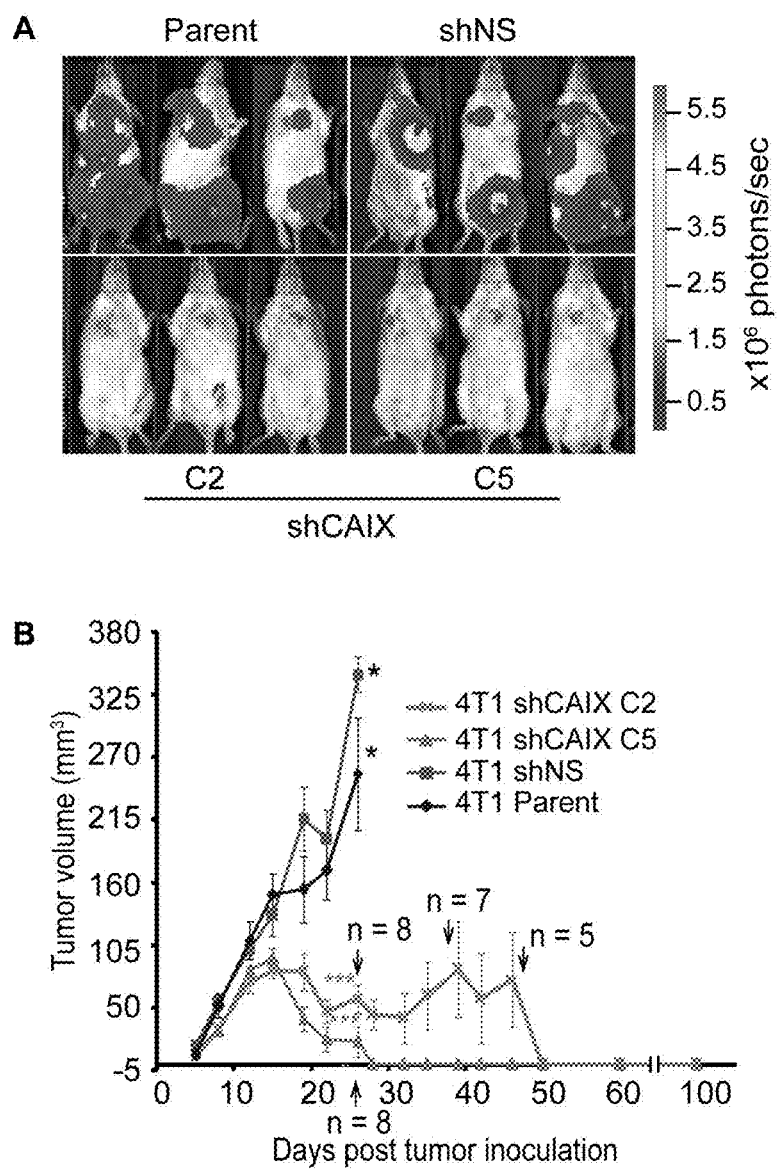
FIG. 6 shows (A) representative bioluminescent images of spontaneous metastasis using the 4T1 tumor model. Heat maps (light, least intense; darker, most intense;) are shown overlaid on gray-scale body images. (B) Same view, but with 4T1 cells expressing shNS or shCAIX and parental 4T1 cells inoculated into the mammary gland of 10 BALB/c mice. * denotes completion of primary tumor excision from the control groups.

Stable depletion of CAIX in the 4T1 mouse breast tumor model inhibits primary tumor growth and metastasis as shown in FIG. 6. Specifically, representative bioluminescent images of spontaneous metastasis using the 4T1 tumor model are used to demonstrate this finding. Pseudo-color heat maps (light, least intense, dark, most intense) are shown overlaid on murine body images. For these studies, 4T1 cells expressing shNS or shCAIX and parental 4T1 cells were inoculated into the mammary gland of BALB/c mice. Animals were monitored for tumor growth. n=10 for each group. Results are expressed as means±s.e.m. * denotes completion of primary tumor excision from the control groups. ***$P<10^{-11}$ with a two-sided Student's t-test, compared to the shNS group.

The results show that 4T1 cells readily form tumors that grow steadily over 30 days while tumors established from CAIX-depleted cells regressed significantly after initial tumor growth (FIG. 6A). The regression of the tumors appeared to be stable, as there are only two mice with primary tumor recurrence appearing towards the end of the study (FIG. 6B). Thus, elimination of CAIX expression has a dramatic effect on the overall survival of the mice. While the animals bearing tumors that express CAIX have to be sacrificed due to progressive metastatic disease, the survival rate of animals inoculated with CAIX-depleted 4T1 cells remained at 100%.

CAIX expression is down regulated in the tumors derived from CAIX-depleted 4T1 cells. There is no difference in the expression levels of CAXII between the shCAIX 4T1 tumors and the control tumors, suggesting that tumor growth suppression in this model occurs in the presence of CAXII, and that CAIX is the critical enzyme for survival and growth of hypoxic breast tumors.

Example 6

Breast Tumor Models

Stable depletion of CAIX in the 4T1 mouse breast tumor model inhibits primary tumor growth and metastasis. In FIG. 6(A) spontaneous metastasis using the 4T1 tumor model are visualized using bioluminescence heat maps (lighter, least intense, darker, most intense) overlaid on gray-scale body images. (B) 4T1 cells expressing shNS or shCAIX and parental 4T1 cells were inoculated into the mammary gland of BALB/c mice. Ten animals in each group were monitored for tumor growth. Arrows denote changes in the number of animals, and revised values are indicated. The results are expressed as means±s.e.m. A "*" denotes completion of primary tumor excision from the control groups. ***$P<10^{-11}$ with a two-sided Student's t-test, compared to the shNS group.

Figure 7:
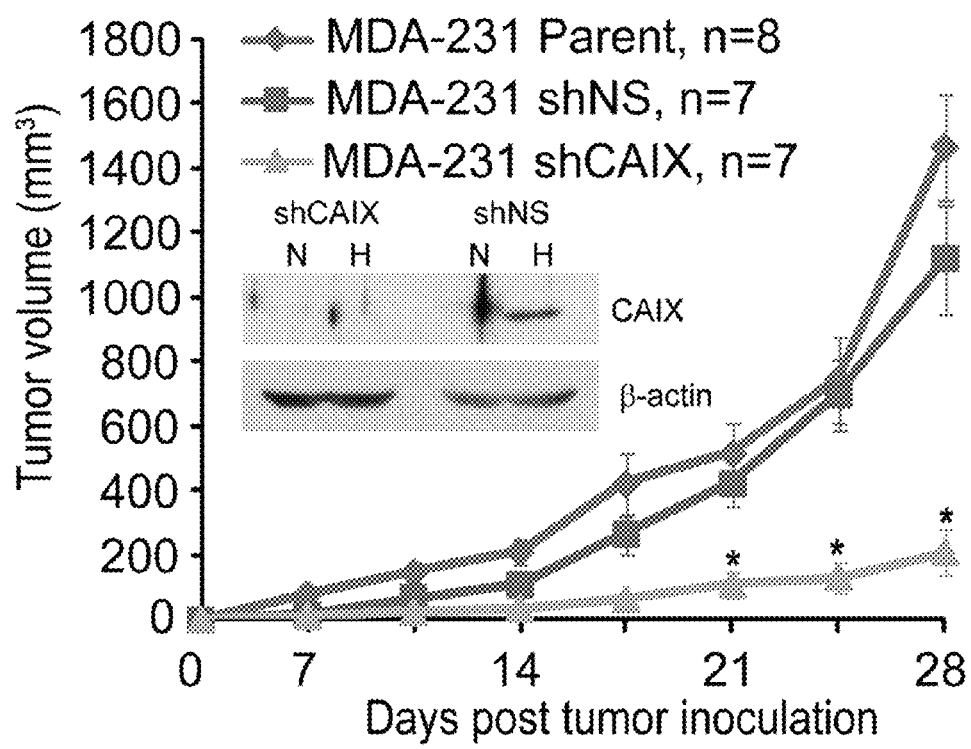
FIG. 7 illustrates reduced primary tumor growth by human breast cancer cells depleted of CAIX expression. MDA-MB-231 cells expressing shNS or shCAIX and parental MDA-MB-231 cells were subcutaneously inoculated into flank of NOD.CB17-prkdc$^{scid}$/J mice and animals were monitored for tumor growth. n=7 for each group. Inset: MDA-MB-231 cells expressing shRNAmir targeting human CAIX (shCAIX) or a non-silencing control sequence (shNS) were cultured in normoxia or hypoxia for 72 h and analyzed for hypoxia-induced CAIX expression Western blot is shown. β-actin served as a loading control.

CAIX depletion in human breast cancer MDA-MB-231 cell line with CAIX shRNA shows significant inhibition of hypoxia-induced CAIX expression in these cells relative to parental and non-silencing control cells (FIG. 7). Moreover, depletion of CAIX dramatically attenuates tumor growth of MDA-MB-231 xenografts.

FIG. 7 illustrates the evidence that stable depletion of CAIX in a human breast tumor model inhibits primary tumor growth. MDA-MB-231 cells expressing shNS or shCAIX and parental MDA-MB-231 cells were subcutaneously inoculated into flank of NOD.CB17-prkdc$^{scid}$/J mice and animals were monitored for tumor growth (n=7 for each group). *$P<0.01$ with a two-sided Student's t-test, compared to shNS control tumors. In the FIG. 7 inset, MDA-MB-231 cells expressing shRNAmir targeting human CAIX (shCAIX) or a non-silencing control sequence (shNS) were cultured in normoxia or hypoxia for 72 h and analyzed for hypoxia-induced CAIX expression. Western blot is shown. β-actin served as a loading control.

Example 7

Metastases Model

Figure 8:
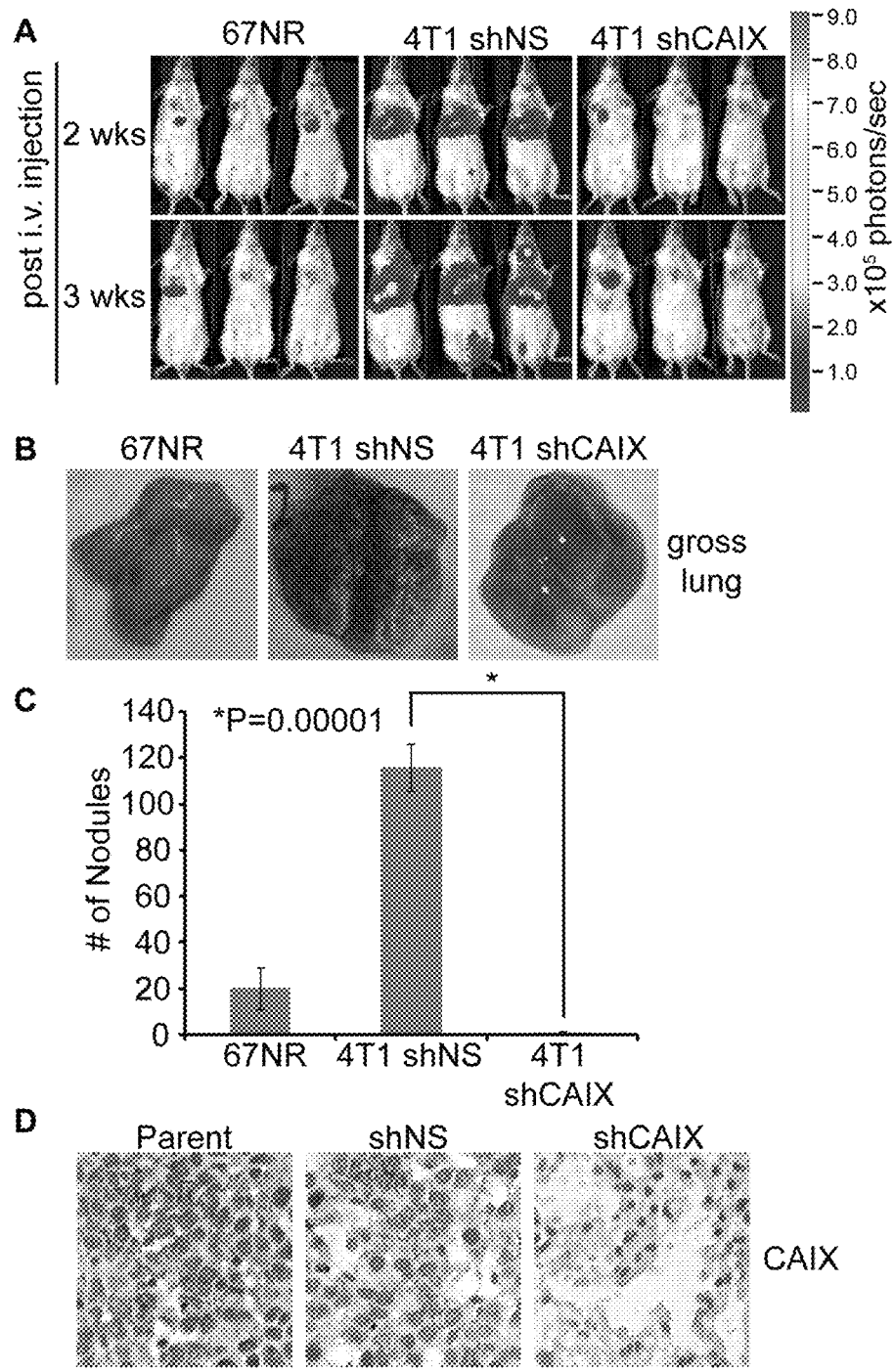
FIG. 8 shows that the depletion of CAIX inhibits of formation of lung metastases in an experimental metastasis model. Panel (A) shows representative bioluminescent images of experimental metastasis by CAIX-expressing 4T1 cells. Panel (B) shows the presence of metastatic nodules in gross images of mouse lungs from the 4T1 shNS group. Panel (C) shows quantification of the number of visible nodules in the different tumor groups. Panel (D) shows immunohistochemical staining of CAIX in 4TI cell-derived lung metastases.

Cell line 4T1 injected intravenously form robust lung metastases and subject mice had to be euthanized within 3 weeks post injection due to metastatic progression, but no metastases were observed in mice that had been inoculated with the CAIX-depleted cells (FIG. 8A). Tumor cells depleted of CAIX showed almost no visible metastasis to the lungs and remain completely healthy (FIG. 8B). Negative control 67NR cells, which are not spontaneously metastatic, show little evidence of metastasis after three weeks post-injection, despite the fact that the cells concentrated in the lungs at 24 hours post-injection.

Examination of lungs from animals injected with cells expressing CAIX exhibited large numbers of lung surface nodules, while the lungs from mice injected with cells depleted of CAIX were essentially normal (FIG. 8C). Stable depletion of CAIX inhibits establishment of lung metastases in the 4T1 model.

Membrane-localized CAIX expression was evident in histologic sections of lungs from control animals, but not from mice bearing CAIX-depleted cells (FIG. 8D).

Example 8

Selectivity of MST-017 (CAI 17)

Cells were cultured for 72 h in the presence of 10 μM MST-017. Shown in FIG. 9 are representative images of the FITC-tagged inhibitor bound to the cell lines in the indicated conditions. (C) Cells were cultured for 72 h with or without MST-017 (400, 600 and 400 μM for the 4T1, 66cl4 and 67NR cells, respectively). n=3. The mean changes in extracellular pH ±s.e.m. are shown. For each cell line, changes in the extracellular pH in hypoxia were assessed relative to the baseline extracellular pH measured in parallel cultures grown in normoxia. *$P<0.001$ with a two-sided Student's t-test, compared to cells cultured without inhibitor.

The extracellular pH decreased dramatically in hypoxia in the 66cl4 and the 4T1 metastatic cell lines which express CAIX, but remained unchanged in the 67NR cultures which do not express CAIX. Treatment of the cells with MST-017 reversed acidification of the extracellular medium under hypoxia in the 66cl4 and 4T1 cell cultures (FIG. 9C).

Example 9

In Vivo Tumor Inhibition Using Sulfonamide Compound MST-017

Targeting CAIX activity with a specific small molecule inhibitor attenuates the growth of 4T1 primary tumors (FIG.

Figure 10:
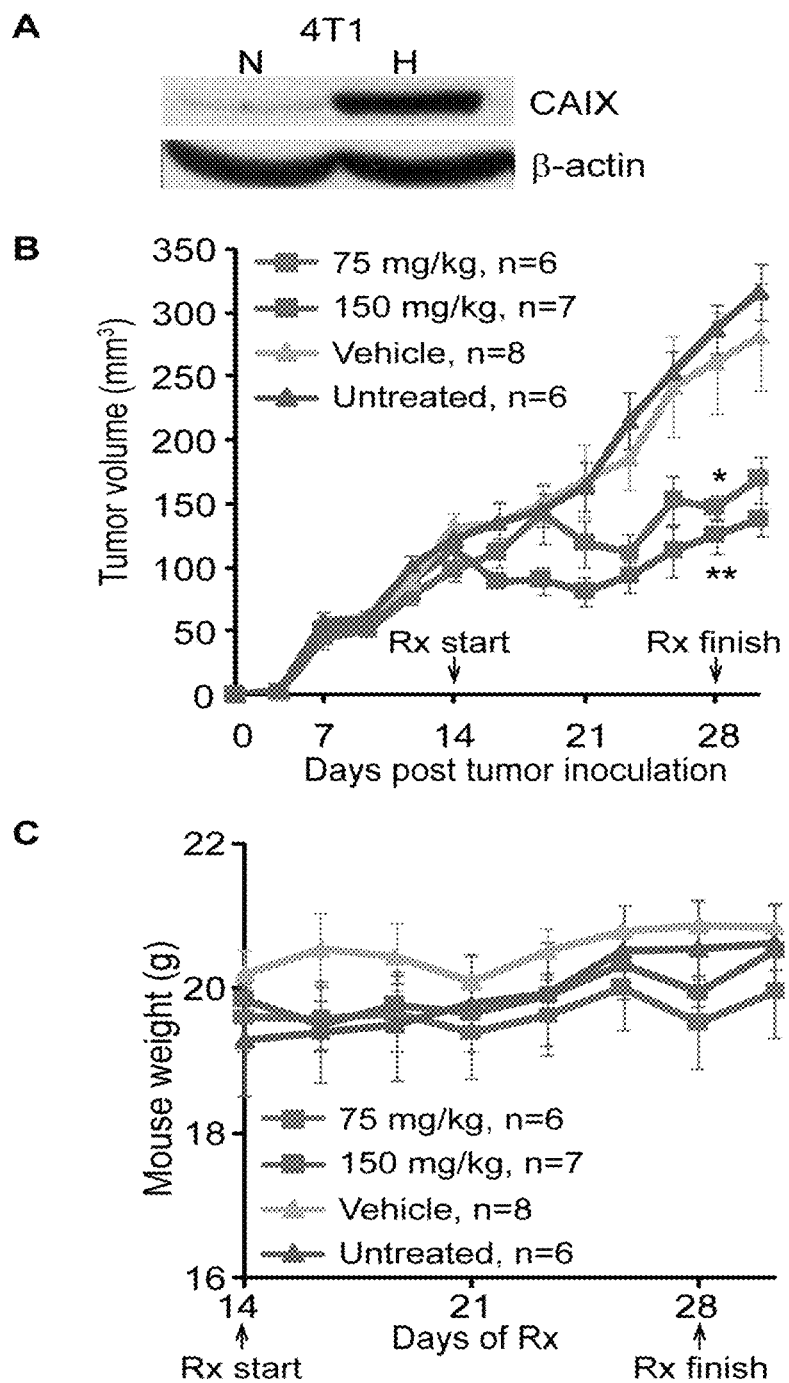
FIG. 10 shows data showing the in vivo efficacy of MST-017 to attenuate the growth of 4T1 primary tumors. (A) 4T1 cells levels of CAIX expression were analyzed by Western blot. (B) Left panel, tumor growth was monitored by caliper-based measurement. Treatment initiation and termination are indicated by arrows. Vehicle-treated and untreated animals served as controls. (C) The weights of treated animals were monitored as a measure of general inhibitor toxicity. Mice were weighed just prior to each dose of the CAIX inhibitor.

10). In FIG. 10(A), 4T1 Cells were cultured in normoxia or hypoxia and levels of CAIX expression were analyzed by Western blot.

Animals were inoculated orthotopically with 4T1 cells. Tumors were allowed to establish for 14 days. Mice were injected with the indicated doses of MST-017 3× per week for 2 weeks. Left panel, tumor growth was monitored by caliper-based measurement. Treatment initiation and termination are indicated by arrows (FIG. 10B). Vehicle-treated and untreated animals served as controls. *P<0.02, **P<0.01 using a 2-sided Student's t-test, compared to vehicle controls.

The weights of treated animals were monitored as a measure of general inhibitor toxicity. Mice were weighed just prior to each dose of the CAIX inhibitor. No significant differences in the weights among the various treatment and control arms were noted (FIG. 10O).

Thus, treatment of mice harboring established 4T1 tumors with MST-017 showed significant inhibition of tumor growth in treated mice compared to vehicle controls. The inhibitor concentrations and the dosing schedule were well-tolerated, as no significant weight reduction was noted in the treated mice.

Figure 11:
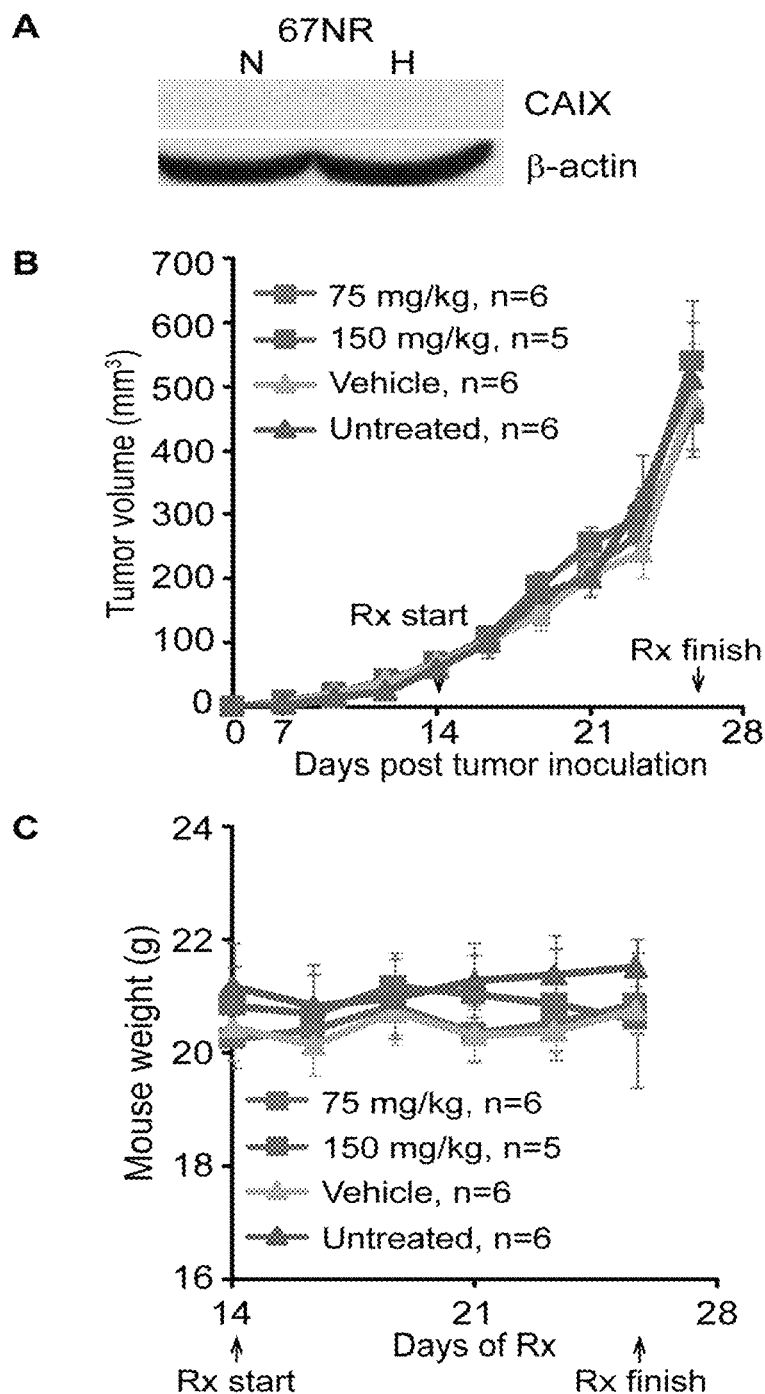
FIG. 11 shows the differences in 67NR tumor growth for animals treated as graphed and by Western blot of CAIX. For (A), 67NR Cells were cultured in normoxia or hypoxia and levels of CAIX expression were analyzed by Western blot. For (B), animals were inoculated with 67NR cells and treated as for FIG. 10. The frame (C) graph shows data showing that no significant differences in the weights among the various treatment and control arms were noted.

Treated mice harboring established 67NR-derived tumors with identical concentrations of MST-017 showed no significant effect of the inhibitor relative to the vehicle control (FIG. 11) and no significant weight reduction was observed.

Example 10

In Vivo Metastases Inhibition with Novel Sulfonamides MST-104 and MST-119

Figure 12:
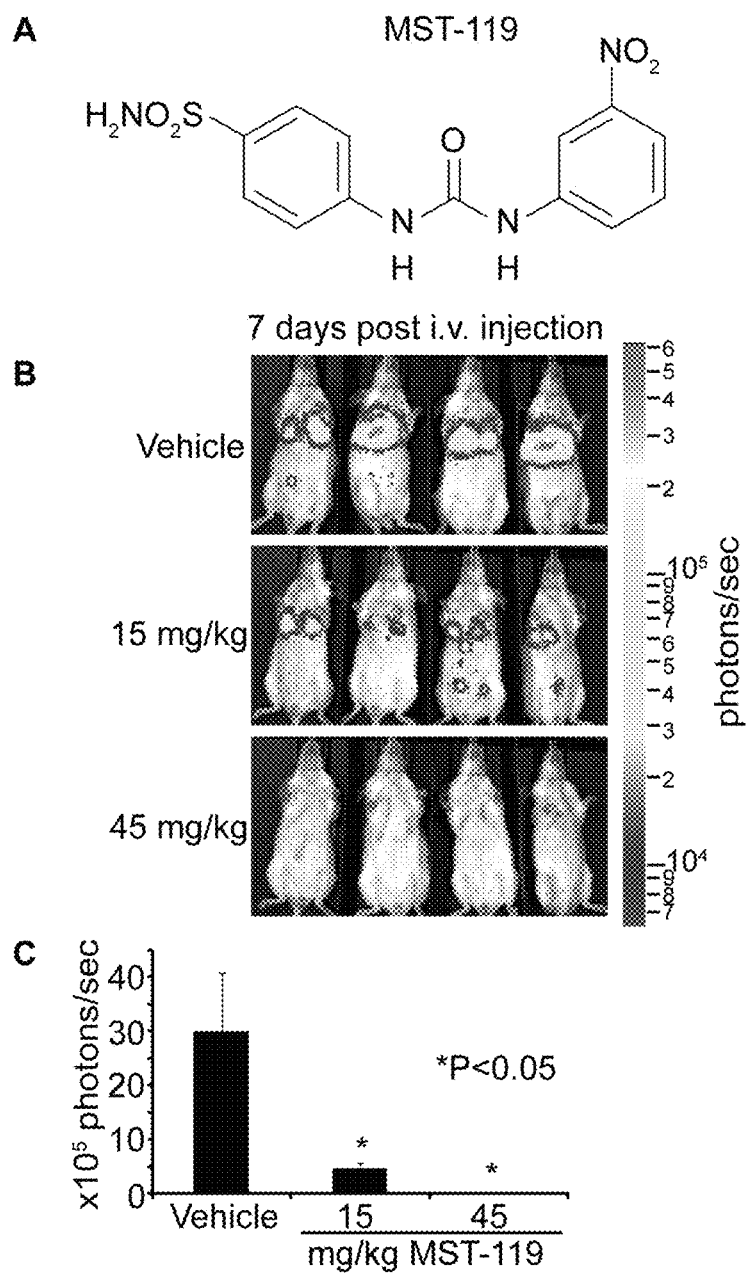
FIG. 12 shows (A) the chemical structure of CAIX inhibitor MST-119, and (B) representative bioluminescent images of metastases established following intravenous injection 4T1 cells and treatment with MST-119. Frame (C) illustrates the results of quantification of tumor-derived bioluminescence.

Novel CAIX inhibitor MST-119 reduces the formation of metastases by 4T1 mammary tumor cells. The chemical structure of CAIX inhibitor MST-119 is shown in FIG. 12A. Representative bioluminescent images of metastases established following intravenous injection of 4T1 cells and treatment with MST-119 is shown in 12B. Animals were treated 24 hours post inoculation of cells. Three doses were administered by i.p. injection over 6 days and the mice were imaged 24 hours following the third dose of inhibitor. MST-119 was delivered in a vehicle comprised of 37.5% PEG400, 12.5% ethanol and 50% saline. Quantification of tumor-derived bioluminescence is shown in 12C. Regions of interest were positioned around metastatic foci and total flux (photons/sec) at the mouse surface was calculated. Data are reported as the mean±s.e.m. N=4 per group. *P<0.05.

Figure 13:
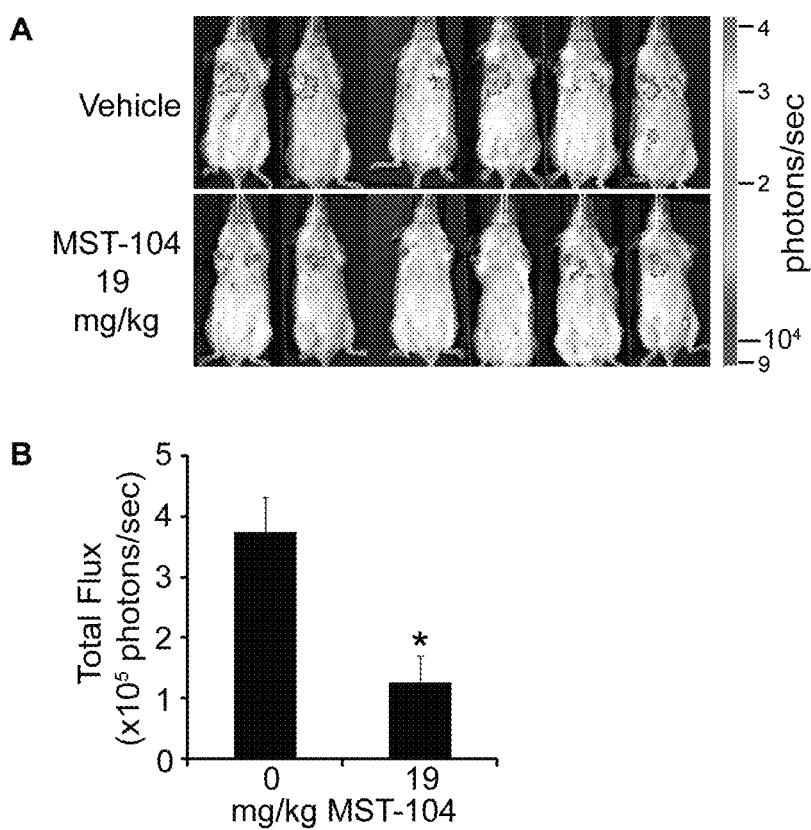
FIG. 13 shows (A) representative bioluminescent images of metastases established following intravenous injection of 4T1 cells and treatment with MST-104. Frame (B) illustrates the results of quantification of tumor-derived bioluminescence.

Novel CAIX inhibitor MST-104 reduces formation of metastases by 4T1 mammary tumor cells (FIG. 13). 4T1 cells were injected directly into the tail vein of BALB/c mice. Daily treatment for 5 days with vehicle or MST-104 was initiated 24 hours post inoculation of cells and mice were imaged 24 hours following the final dose. Vehicle and inhibitor were administered by i.p. injection. Shown are representative images of tumor-cell derived bioluminescence in control and inhibitor-treated animals. (B) The graph shows quantification of tumor-derived bioluminescence. n=6 per group. *P<0.01. Quantification of the bioluminescent signal revealed a statistically significant decrease in the formation of metastases in the treated mice. These data provide further illustration of the inhibition of formation of lung metastases by breast cancer cells in response to targeted inhibition of CAIX using novel sulfonamides.

Example 11

Inhibition of Human Primary Breast Tumor Growth with Novel Sulfonamides

Novel CAIX inhibitor MST-104 reduces the growth of human primary breast cancer xenografts. Metastatic MDA-MB-231 LM2-4$^{Luc+}$ cells were implanted orthotopically into NOD/SCID mice. When tumors reached an average of 200 mm$^3$, animals received the indicated doses of MST-104 daily by i.p. administration and tumor growth was quantified using caliper measurements. The initiation and termination of inhibitor treatment is indicated. n=8/group. *P<0.03, **P<0.001. Inset, Western blot showing CAIX expression by the LM2-4$^{Luc+}$ cells cultured in normoxia (N) and hypoxia (H).

Figure 14:
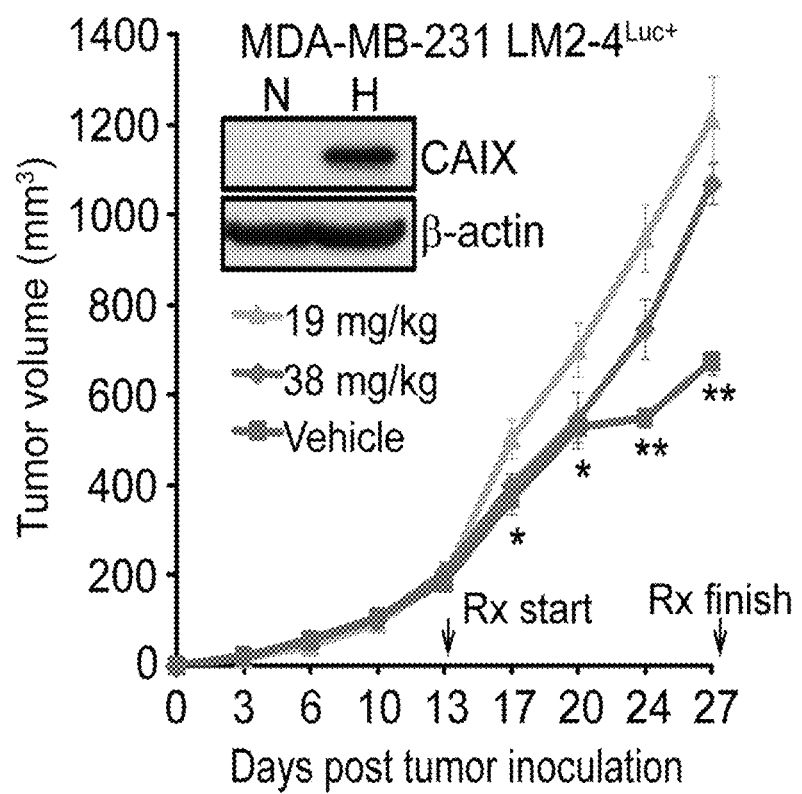
FIG. 14 shows dose-dependent inhibition of growth of human breast tumors implanted orthotopically in the mammary gland and treated with CAIX inhibitor MST-104. Tumor growth was monitored over time. The inset panel shows that these cells up-regulate expression of CAIX when grown in hypoxia.

To evaluate the effect of pharmacologic inhibition of CAIX activity in vivo, we treated mice harboring established MDA-231 LM2-4 tumors (Ebos et al., 2009) with MST-104. These cells were observed to induce robustly CAIX in hypoxia (FIG. 14, inset). We observed significant, dose-dependent inhibition of tumor growth in mice treated with the inhibitor, compared to vehicle controls (FIG. 14). These data show the ability of sulfonamide-based CAIX inhibitors to specifically target CAIX-expressing human breast tumors.

Example 12

Figure 15:
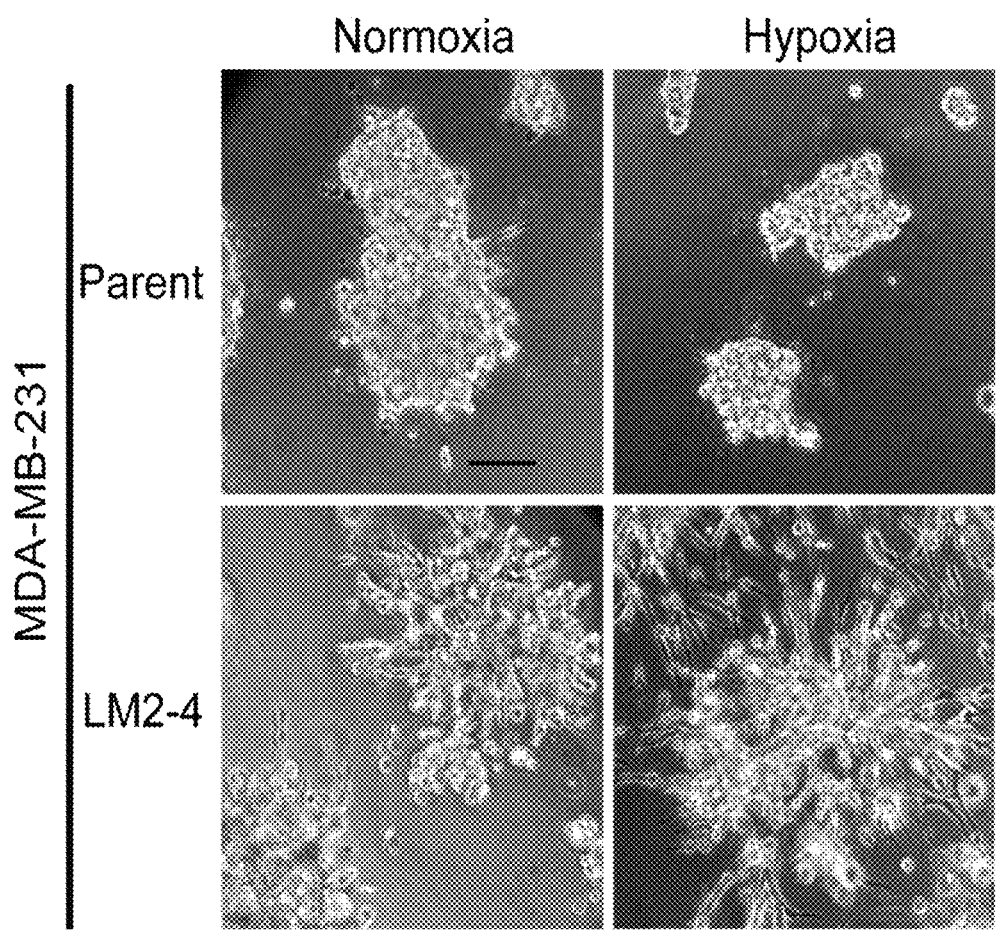
FIG. 15 shows that in contrast to the parental MDA-MB-231 human breast cancer cells, the highly lung-metastatic MDA-231 LM2-4 cells are invasive when cultured in 3D Matrigel™ cultures in hypoxia.

Inhibition of Hypdxia-Induced Invasion and Survival of Human Breast Cancer Cells Grown in 3D Matrigel™ Cultures by Novel Sulfonamides MDA-MB-231 LM2-4$^{Luc+}$ cells grown in 3D Matrigel™ cultures are invasive in hypoxia (FIG. 15). Cells were cultured in a 3D "on-top" Matrigel™ assay for 4 days in normoxia and hypoxia as described in the methods. Representative phase-contrast images of 3D cultures are shown. Hypoxia induced invasion by the LM2-4 variant, but not by the parental MDA-231 cells.

Figure 16:
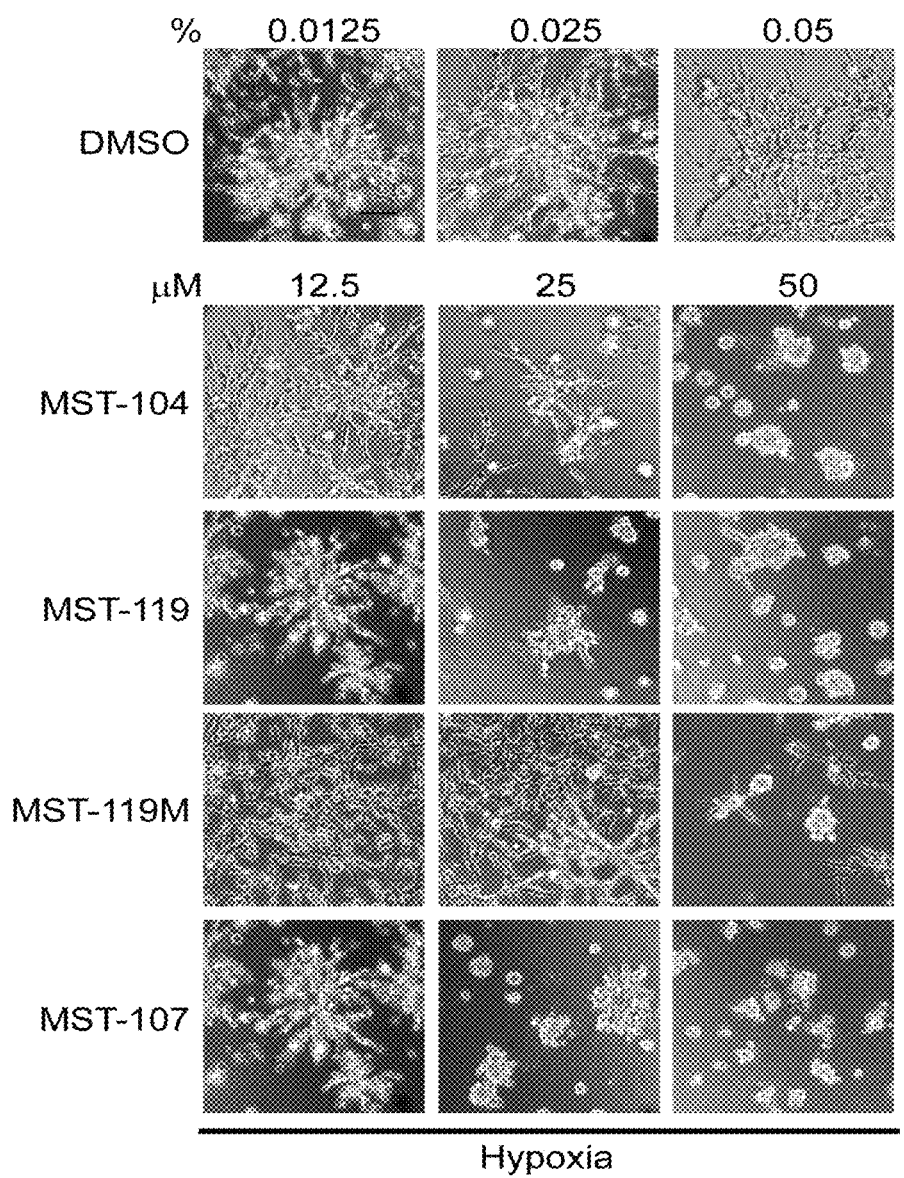
FIG. 16 shows that ureido-sulfonamide inhibitors of CAIX (MST-104, MST-119, MST-107, MST-130) inhibit invasion of highly metastatic human breast cancer cells in 3D Matrigel™ cultures in hypoxia.

Treatment with novel sulfonamide inhibitors of CAIX attenuates hypoxia-induced invasion of human breast cancer cells grown in 3D Matrigel™ cultures (FIG. 16). Cells were cultured in 3D "on-top" Matrigel™ assays for 4 days in hypoxia in the presence of inhibitors. DMSO-treated cell cultures served as controls. The percentage concentration of DMSO and molar concentration of inhibitors are indicated. Representative phase contrast images are shown. These data show that sulfonamides inhibit invasion of metastatic human breast cancer cells in hypoxia.

Figure 17:
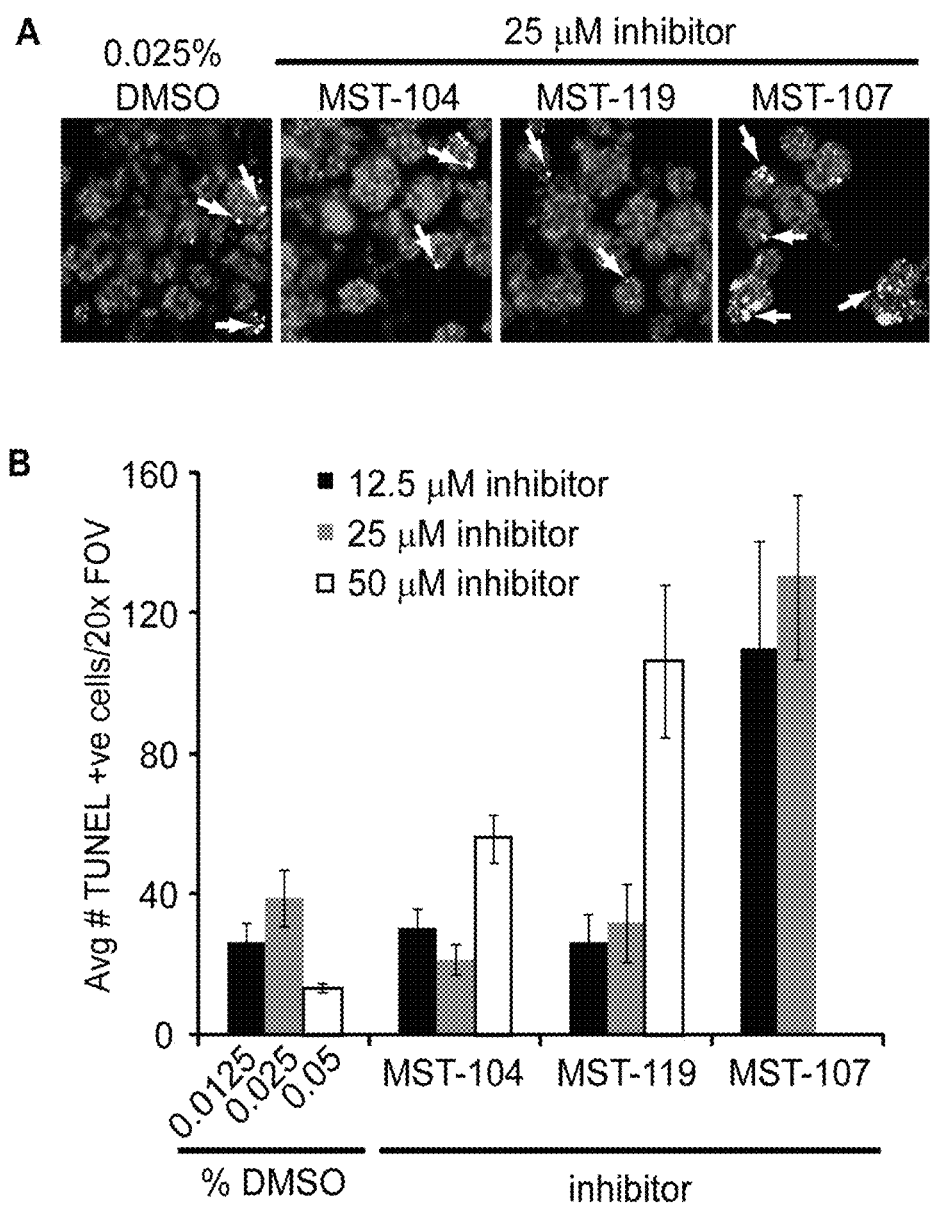
FIG. 17 shows differential effects ureido-sulfonamides on cell death in 3D Matrigel™ cultures in hypoxia. (A) Representative images of the number of TUNEL-positive cells. Frame (B) illustrates the results of quantification of TUNEL-positive cells.

Ureido sulfonamide inhibitors of CAIX show differential effects on cell death of human breast cancer cells in hypoxia (FIG. 17). Cells were cultured in 3D "on-top" Matrigel™ assays. Cells were growth in the presence of inhibitors for 4 days in hypoxia. DMSO-treated cell cultures served as controls. (A) Representative images of TUNEL-positive cells (arrows). (B) Graph showing quantification of TUNEL +ve cells by counting 5 random fields per condition. Data are expressed as the average number of TUNEL-positive cells/20× field of view (FOV). These data show that sulfonamide inhibitors of CAIX can induce death of human breast cancer cells in hypoxia.

Example 13

Figure 18:
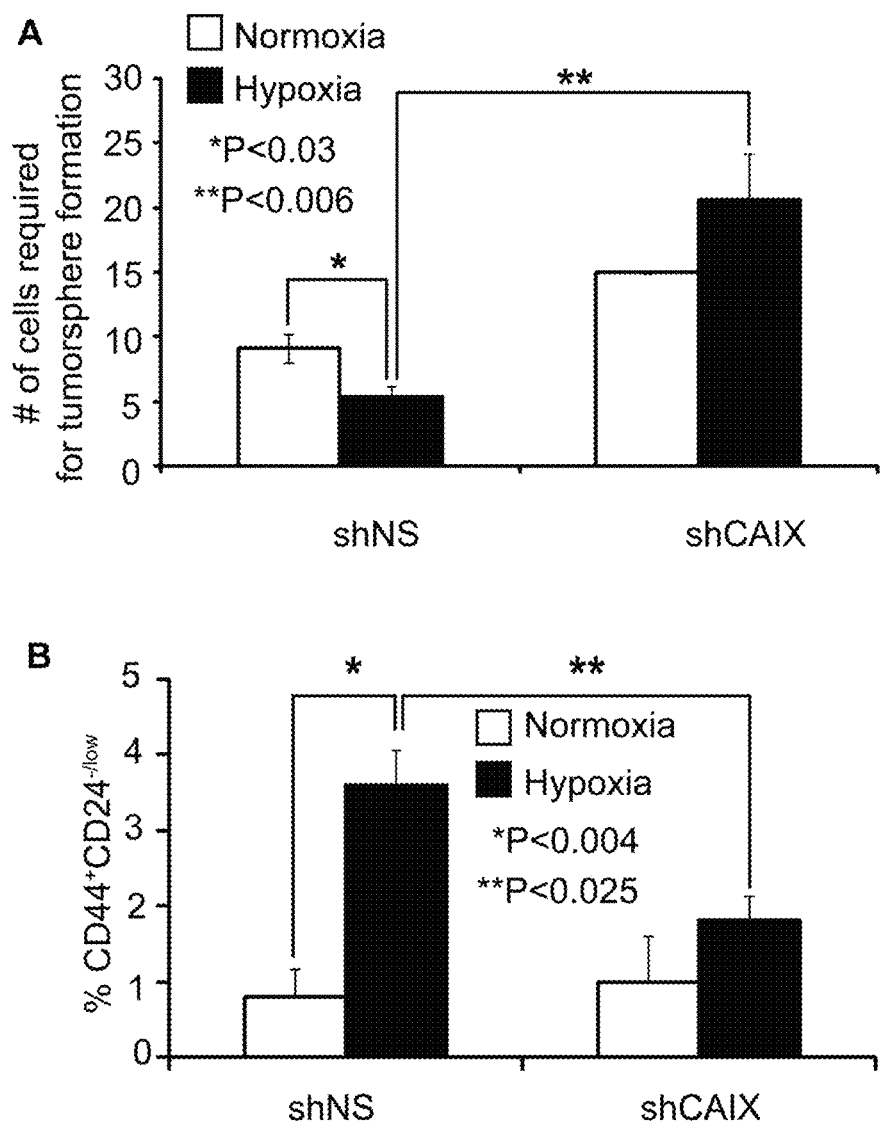
FIG. 18 shows that genetic depletion of CAIX expression in 4T1 breast cancer cells (A) increases the number of cells required to initiate tumorsphere growth in hypoxia and (B) reduces the hypoxia-induced increase in CD44$^+$/CD24$^{-/low}$ cancer stem cells.

Genetic Depletion of CAIX Expression in Breast Cancer Cells Reduces the Cancer Stem Cell Population in Hypdxia In vitro proliferation in suspension under serum free conditions as non-adherent tumorspheres is a characteristic of breast cancer stem cells. The breast cancer stem cell population has previously been characterized as displaying the CD44$^+$CD24$^{-/low}$ signature (Al-Hajj et al, (2003) Proc Natl Acad Sci USA 100:3983-3988); Ponti et al, (2005) Cancer Res 65:5506-5511). FIG. 18 shows that CAIX expression is required for growth of the "tumorsphere initiating" population and tumorsphere-forming efficiency in hypoxia. (A) 4T1 shNS and shCAIX cells were seeded at doubling dilutions and cultured under tumorsphere-forming conditions in normoxia or hypoxia. The number of cells required to initiate tumorsphere growth was assessed. Mean±SEM of three independent experiments is shown. *P<0.03, **P<0.006. (B) 4T1 shNS and shCAIX cells were cultured as tumorspheres in normoxia or hypoxia, disaggregated and the CD44+CD24−/low population assessed by FACS analysis. Data shown are the mean changes in % CD44+CD24−/low cells ±SEM, from 3 independent experiments. *P<0.004, **P<0.025.

No significant difference in the number of cells required to form tumorspheres was observed between 4T1 shNS and shCAIX in normoxia, since CIAX is not induced in either cell line at normal oxygen levels (FIG. 18A). The number of 4T1-shNS cells required to form tumorspheres was significantly reduced in hypoxia, compared to normoxia controls, suggesting that the percentage of cancer stem cells (CSC) is significantly higher in hypoxic cultures (FIG. 18A). Importantly, RNAi-mediated knock down of CIAX expression significantly increased the number of seeding cells required to form a tumorsphere in hypoxia, showing that CAIX expression is required for the observed CSC-like expansion in hypoxia with shNS-4T1 controls cells.

In FIG. 18B, 4T1 shNS and shCAIX cells were cultured under tumorsphere forming conditions, in normoxia or hypoxia, and analyzed by FACS to quantify the putative CSC-like population labeled as CD44$^+$CD24$^{-/low}$. In shNS controls, the CD44$^+$CD24$^{-/low}$ population is significantly increased in hypoxic culture conditions, compared to normoxic controls (FIG. 18B). However, RNAi-mediated knockdown of CAIX significantly depletes this population in hypoxia, showing that CAIX is required for CD44$^+$ CD24$^{-/low}$ CSC-like expansion in hypoxia (FIG. 18B).

Example 14

Figure 19:
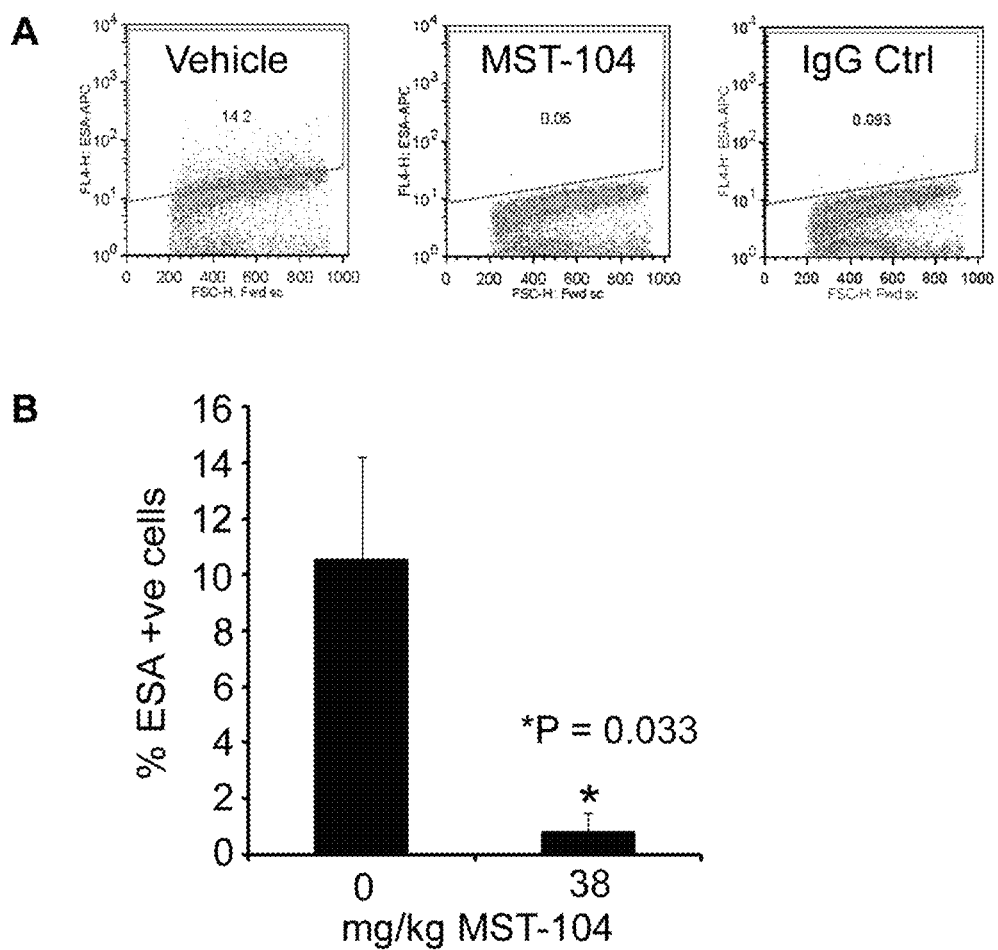
FIG. 19 shows that treatment of human breast cancer orthotopic tumors with ureido-sulfonamide MST-104 depletes the cancer stem cell population within the tumor. Frame (A) shows representative FACS plots sorting for ESA+ cancer stem cells. Frame (B) illustrates the results of quantification on the number of ESA+ human breast cancer stem cells present in the tumors.

MST-104 can Deplete the Cancer Stem Cell Population in Human Breast Orthotopic Tumors In Vivo FIG. 19 shows that treatment of human primary breast cancer xenografts with CAIX inhibitor MST-104 targets the cancer stem cell population in vivo. MDA-MB-231 LM2-4$^{luc+}$ were implanted orthotopically into NOD/SCID mice. When tumors reached an average of 200 mm$^2$, animals received either vehicle or 38 mg/kg MST-104 daily by i.p. administration. (A) Primary tumors were removed, dissociated and ESA+ cell population assessed by FACS analysis. Representative FACS plots demonstrating the percentage of ESA+ cells are shown. (B) Data shown are the mean changes in ESA+ cells ±SEM, from 3 mice. **P<0.0224.

Vehicle treated tumors contained a mean 10% ESA+ cell population. In comparison, tumors treated with sulfonamide CAIX inhibitor MST-104 also displayed a significantly reduced ESA+ cell population, compared to vehicle-treated control tumors. These data show that sulfonamides can deplete the human breast cancer stem cell population in vivo.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

While specific embodiments have been described and illustrated, such embodiments should be considered illustrative only and not as limiting the invention as construed in accordance with the accompanying claims.

The invention claimed is:

1. A method of suppressing tumor metastases in a mammal with a tumor and is in need of suppressing metastases of the tumor, the method comprising administering to said mammal a therapeutically effective amount of a pharmaceutical composition comprising a compound selected from the group consisting of:
4-{[4'-fluorophenyl)carbamoyl]
amino}benzenesulfonamide (MST-104) and
4-{[3'-nitrophenyl)carbamoyl]
amino}benzenesulfonamide (MST-119);
and a pharmaceutically acceptable excipient,
wherein the tumor overexpresses carbonic anhydrase IX (CAIX) and/or carbonic anhydrase XII (CAXII).

2. The method of claim 1, wherein the mammal is further treated by administering one or more anticancer agents.

3. The method of claim 1, wherein said tumor is a breast carcinoma.

4. A method of treating cancer in a mammal in need of such treatment comprising administering to the mammal a therapeutically effective amount of a pharmaceutical composition comprising a compound selected from the group consisting of:
4-{[4'-fluorophenyl)carbamoyl]
amino}benzenesulfonamide (MST-104) and
4-{[3'-nitrophenyl)carbamoyl]
amino}benzenesulfonamide (MST-119);
and a pharmaceutically acceptable excipient;
wherein said cancer is breast cancer, lung cancer, pancreatic cancer, renal cancer, ovarian cancer, prostate cancer, cervical cancer, glioblastoma or colorectal cancer,
and further wherein the cancer overexpresses CAIX and/or CAXII.

5. The method of claim 4, wherein the mammal is a human.

* * * * *